United States Patent [19]

Heisner et al.

[11] 4,207,470
[45] Jun. 10, 1980

[54] TIRE INSPECTION SYSTEM

[75] Inventors: Donald N. Heisner, Euclid; Charles R. Bentivegna, Mayfield Heights, both of Ohio

[73] Assignee: Monsanto Company, St. Louis, Mo.

[21] Appl. No.: 884,541

[22] Filed: Mar. 8, 1978

Related U.S. Application Data

[62] Division of Ser. No. 495,377, Aug. 7, 1974, Pat. No. 4,088,936.

[51] Int. Cl.$^2$ ............................................. G01N 23/00
[52] U.S. Cl. .................................................... 250/358 T
[58] Field of Search ................................... 250/358 T

[56] References Cited

U.S. PATENT DOCUMENTS

| | | | |
|---|---|---|---|
| 2,220,246 | 11/1940 | Kizaur | 250/358 T |
| 2,272,893 | 2/1942 | Bosonworth | 250/358 T |
| 2,339,550 | 1/1944 | Bosonworth | 250/358 T |
| 3,621,246 | 11/1971 | Horsey | 250/358 T |
| 3,621,247 | 11/1971 | Lide | 250/358 T |
| 3,789,226 | 1/1974 | Green et al. | 250/358 T |
| 3,795,853 | 3/1974 | Whitehouse | 250/358 T |
| 3,809,900 | 5/1974 | Steffel | 250/358 T |
| 3,843,888 | 10/1974 | Fox | 250/358 T |

*Primary Examiner*—Davis L. Willis
*Attorney, Agent, or Firm*—Gordon B. Seward

[57] ABSTRACT

An automated tire inspection system employs penetrative emanation such as X-radiation to inspect the integrity of portions of tires fed sequentially along a feed path through a centering station and into a shielded enclosure where an inspection station is defined. An inspection apparatus within the shielded enclosure includes an X-ray emitting tube and an imaging system for producing signals representing the pattern of X-rays directed through the tire by the X-ray tube. A control apparatus for the system includes:

(1) A protection apparatus for preventing overtravel of movable components of the system, including apparatus for sensing the positions of the movable components and controlling elements for moving the movable components and responding to the sensing apparatus to limit movement of the movable components to within a first predetermined range of positions. Additional apparatus senses when a movable component reaches the boundary of another range of positions encompassing the first range and deactuates the system in response thereto;

(2) A system for detecting and identifying malfunctions in the tire inspection system;

(3) A positioning system for maintaining a constant relative position between the X-ray tube and the imaging system;

(4) An interrupt system for manually terminating the automatic operation of the tire inspection system and enabling manual control thereof;

(5) A speed control system for automatically slowing the motion of each movable component as it approaches a predetermined end point of its path of motion, and (6) A scheduled interrupt system which suspends automatic operation upon the tire inspection system executing a predetermined stop in its automatic operation, to give the operator temporary manual control of a limited number of system operations.

Throughout the operation of the tire inspection system, manual or automatic, the system prevents the execution of potentially dangerous or mechanically destructive operations.

8 Claims, 38 Drawing Figures

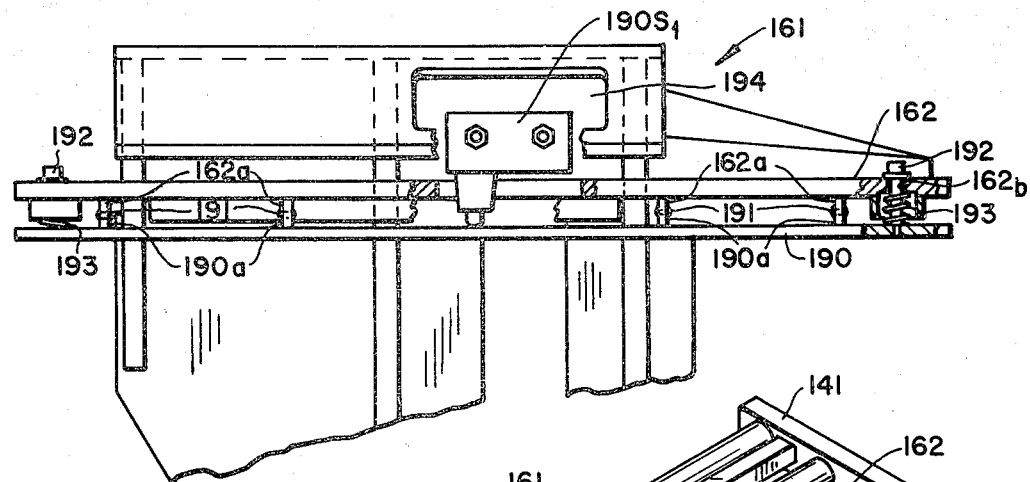
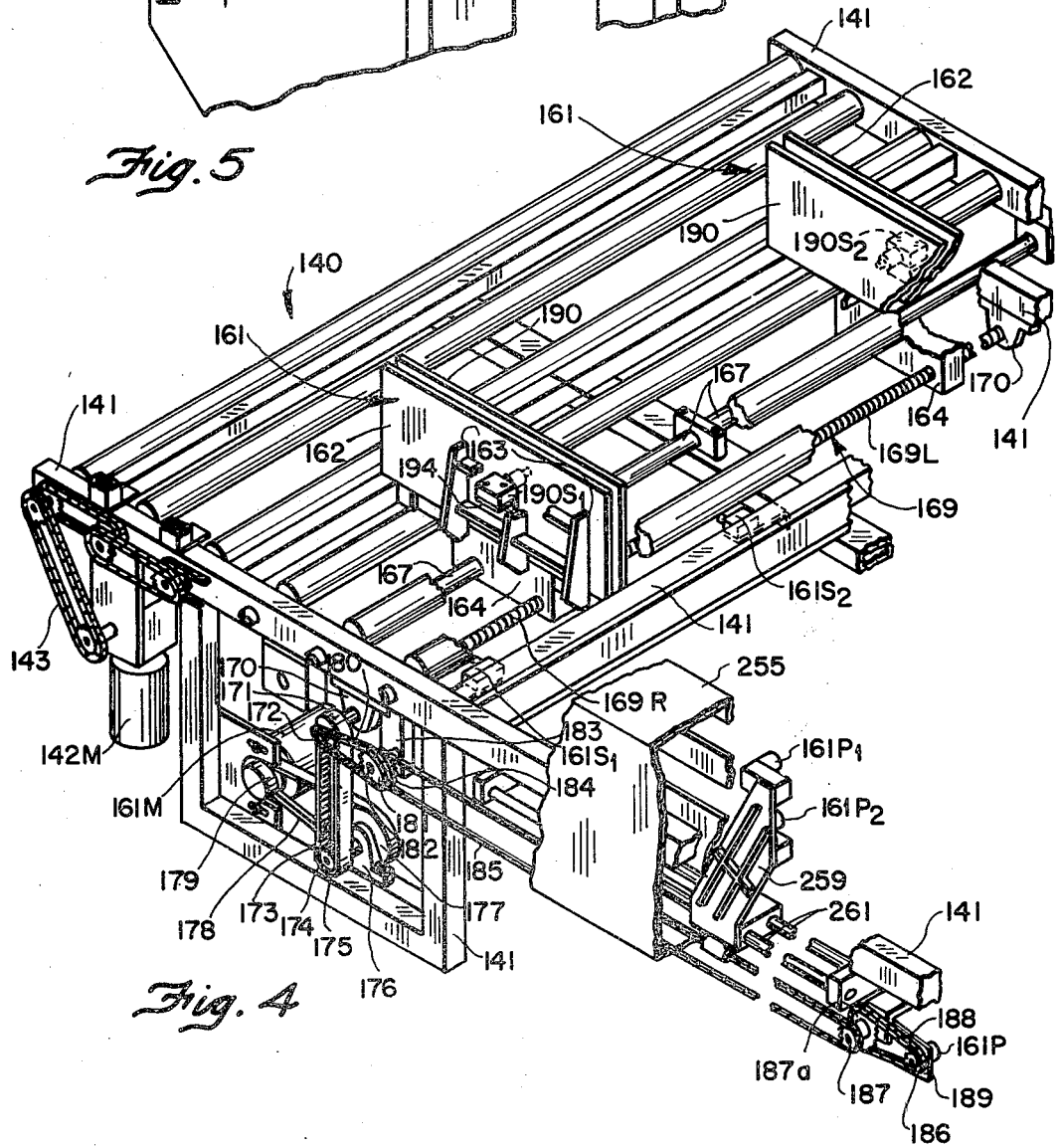

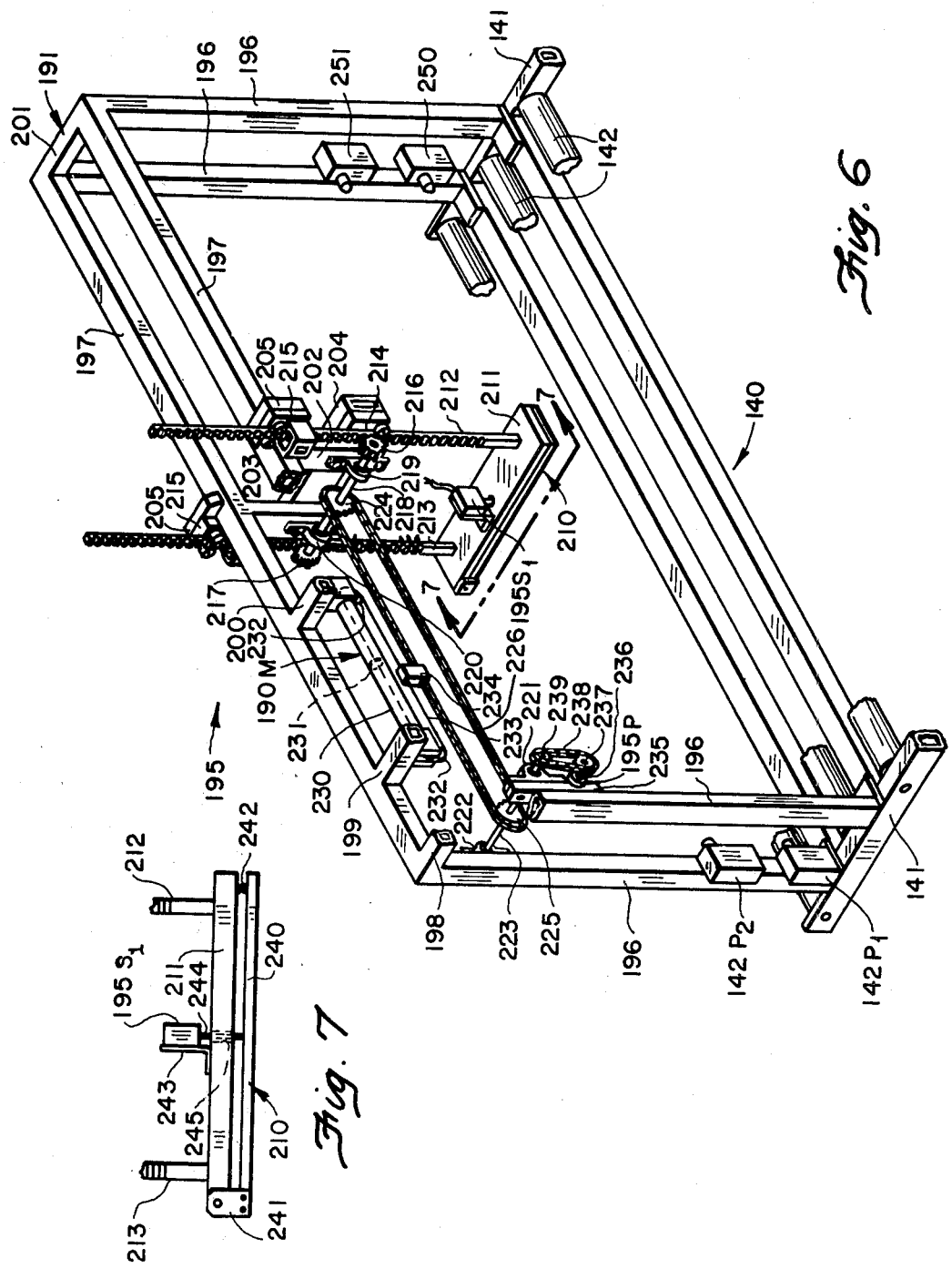

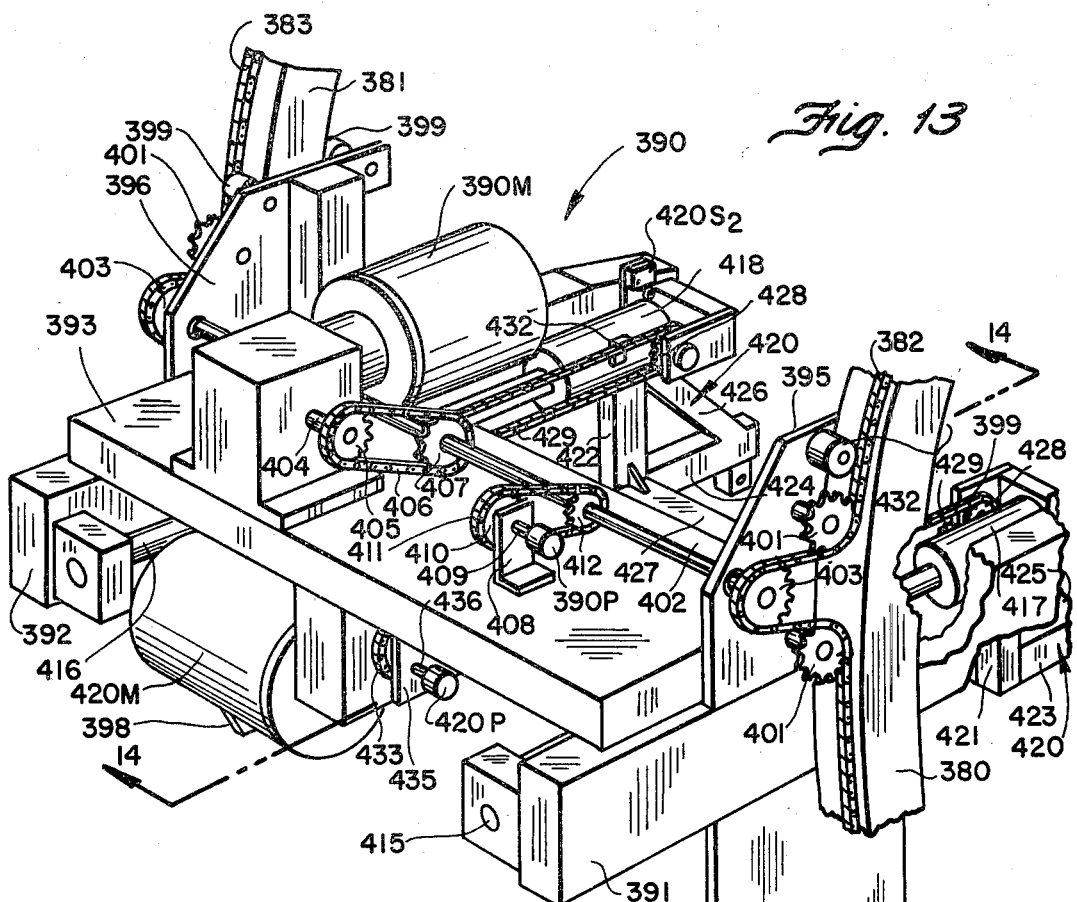
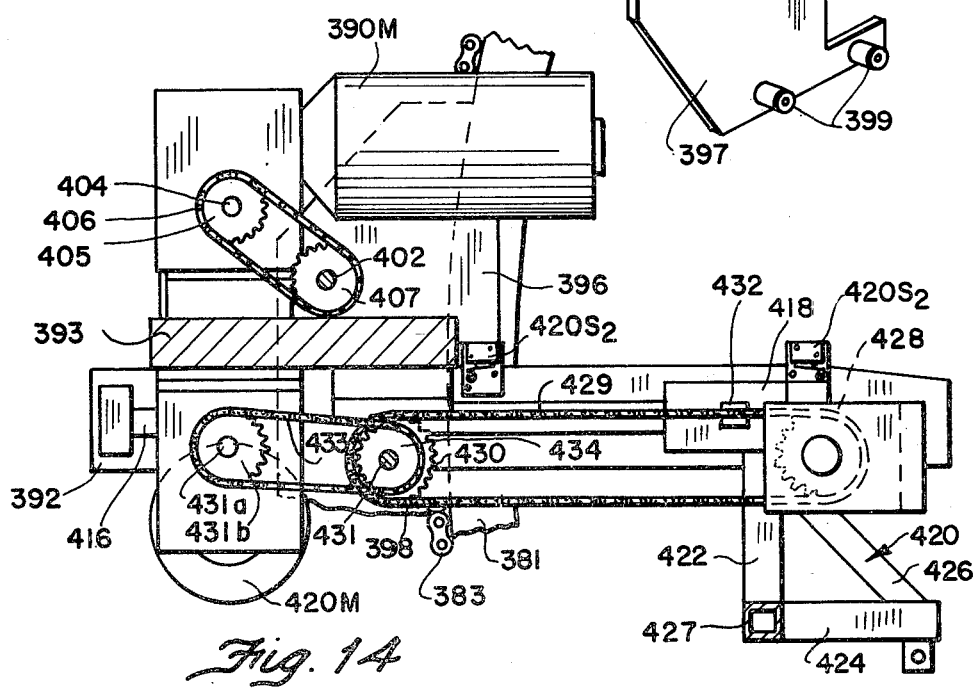

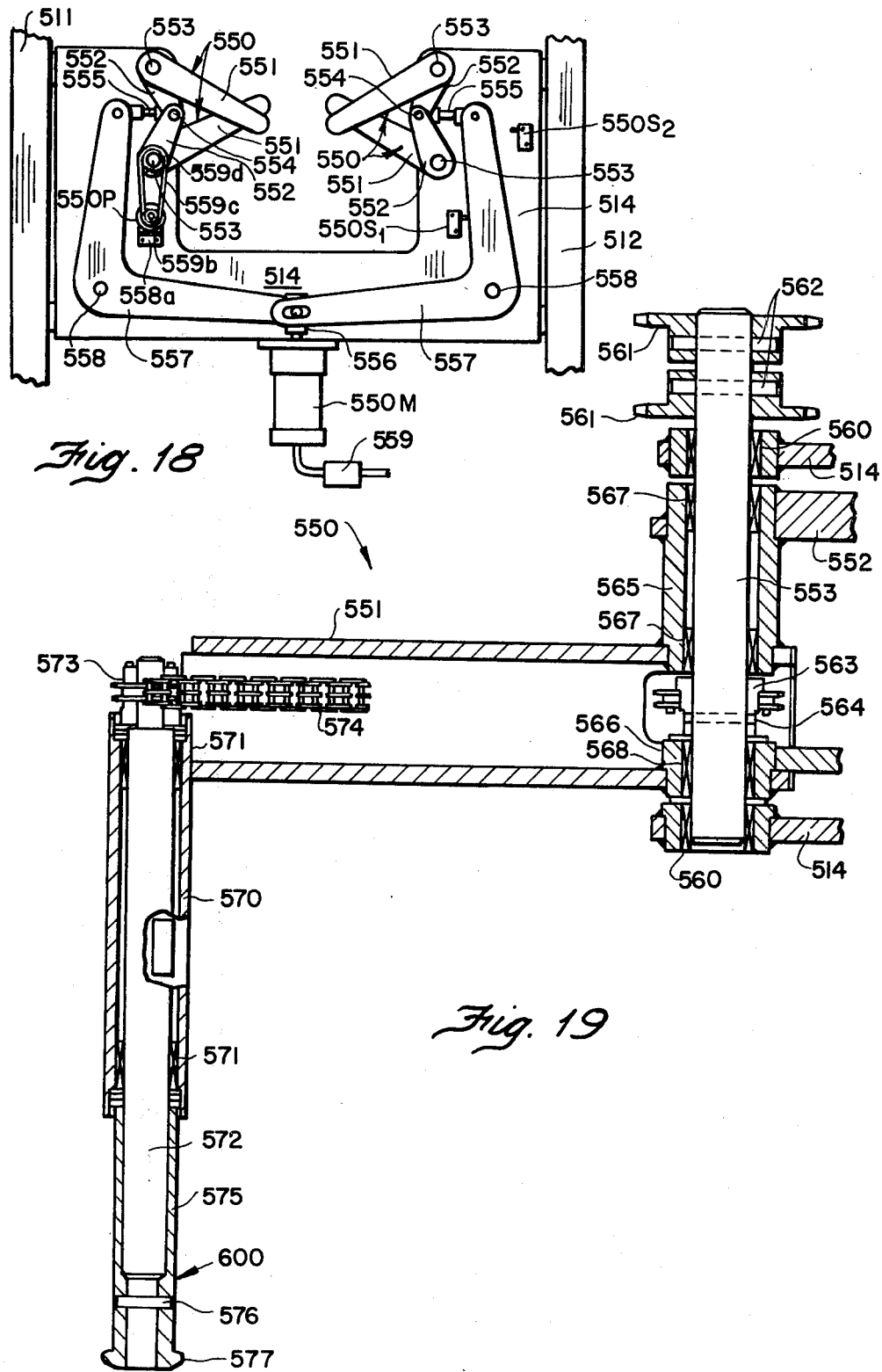

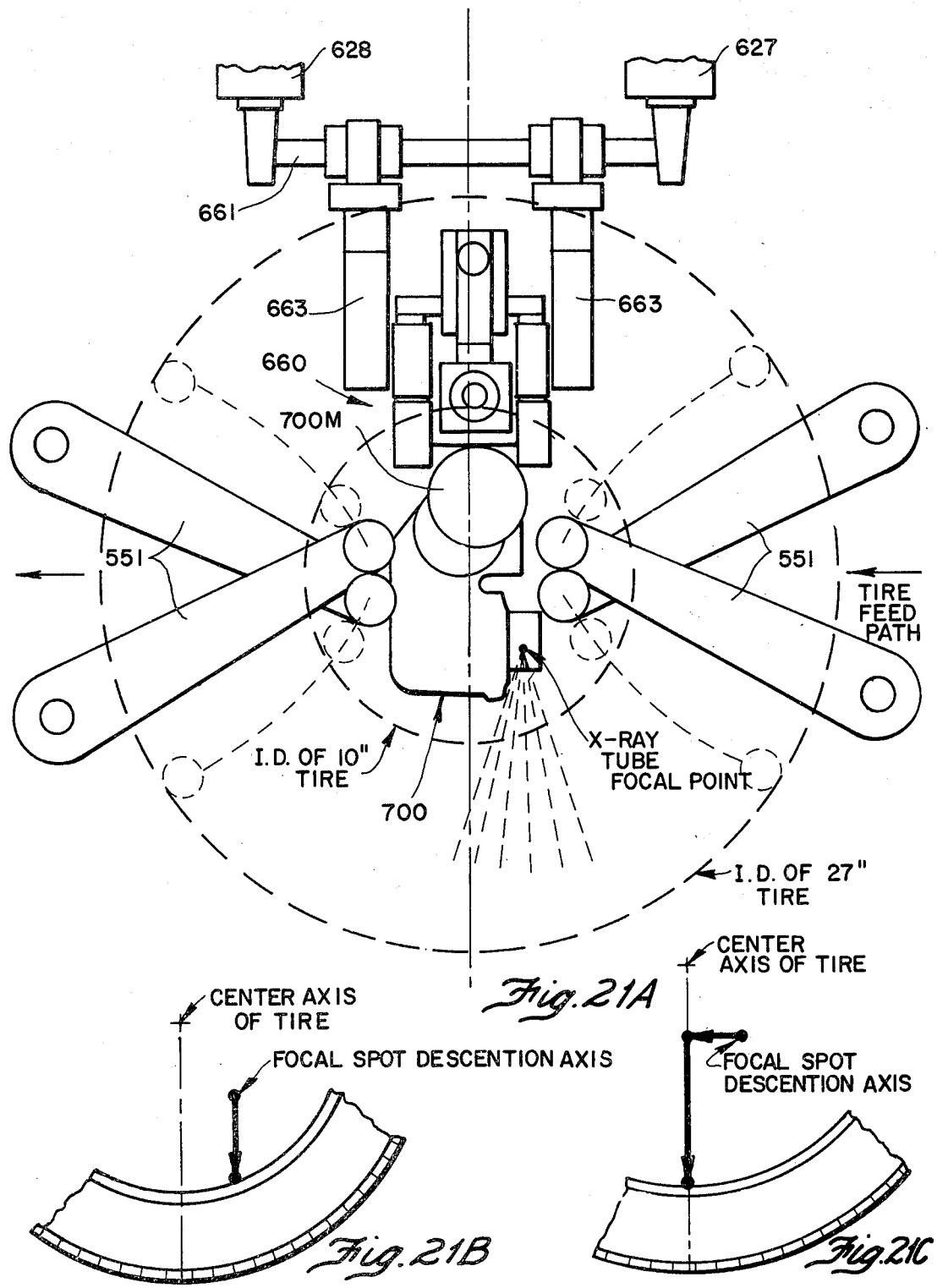

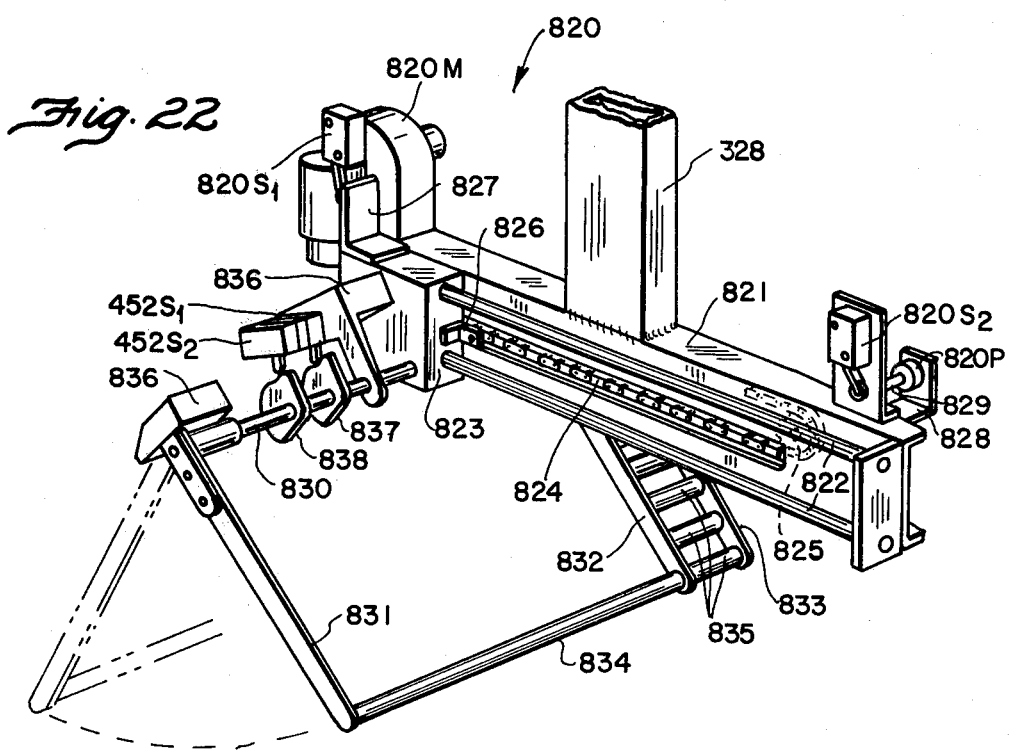

INPUTS FROM LIMIT SWITCHES AND PHOTOCELLS

| Signals | No. | Description |
|---|---|---|
| 1000 101P₁ — 1001 | 1001 | SENSED PRESENCE OF A TIRE ON BELT CONVEYOR-101 |
| 140S₁ — 1002 | 1002 | EXTREME POSITIONS OF CENTERING TABLE CONVEYOR-140 |
| 140S₂ — 1003 | 1003 | |
| 142P₁ / 142P₂ — 1004 | 1004 | SENSED PRESENCE OF A TIRE ON CENTERING CONVEYOR ROLLS-142 |
| 160S₁ — 1005 | 1005 | EXTREME POSITIONS OF CENTERING TABLE ARMS-161 |
| 160S₂ — 1006 | 1006 | |
| 161P₁ / 161P₂ — 1007 | 1007 | SENSED PRESENCE OF AN OBJECT BEHIND TIRE ON CENTERING TABLE |
| 190S₁ 190S₂ — 1008 | 1008 | SENSED ENGAGEMENT OF A TIRE WITH CENTERING TABLE PLATES 190 |
| 195S₁ — 1009 | 1009 | SENSED ENGAGEMENT OF A TIRE WITH HEIGHT SENSOR-195 |
| 278P₁ 278P₁ 278P₂ 278P₂ — 1010 (NC NC NC NC) | 1010 | SENSED PRESENCE OF AN OBJECT IN DOOR OPENINGS-276 |
| 278S₁ 278S₁ 278S₁ 278S₁ — 1011 | 1011 | EXTREME POSITIONS OF DOORS-278 |
| 278S₂ 278S₂ 278S₂ 278S₂ — 1012 (NC NC NC NC) | 1012 | |
| 340S₁ — 1013 | 1013 | EXTREME POSITIONS OF IMAGING SYSTEM CARRIAGE-340 |
| 340S₂ — 1014 | 1014 | |
| 390S₁ — 1015 | 1015 | EXTREME POSITIONS OF IMAGING SUB-CARRIAGE-390 |
| 390S₂ — 1016 | 1016 | |
| 420S₁ — 1017 | 1017 | EXTREME POSITIONS OF IMAGING SUB-SUB-CARRIAGE 420 |
| 420S₂ — 1018 | 1018 | |
| 440S₁ 440S₂ 440S₃ 440P₁ — 1019 (NC NC NC NC) | 1019 | SENSED PROXIMITY OF AN OBJECT TO SCREEN OF IMAGING UNIT-440 |
| 451S₁ — 1020 | 1020 | EXTREME POSITIONS OF MAIN CONVEYOR FRAME-451 |
| 451S₂ — 1021 | 1021 | |
| 452S₁ — 1022 | 1022 | SENSED ARRIVAL OF A TIRE AT INSPECTION STATION |
| 452S₂ — 1023 | 1023 | |
| 456S₁ — 1024 | 1024 | EXTREME POSITIONS OF DROP-AWAY CONVEYOR FRAMES 456 |
| 456S₂ — 1025 | 1025 | |
| 460S₁ — 1026 | 1026 | EXTREME POSITIONS OF MAIN CONVEYOR GEAR RACKS-460 |
| 460S₂ — 1027 | 1027 | |
| 550S₁ — 1028 | 1028 | EXTREME POSITIONS OF SPINDLE ARMS 550 |
| 550S₂ — 1029 | 1029 | |

(INPUTS TO CONTROL CONSOLE-1300)

*Fig. 23A*

ACTUATE BELT CONVEYOR SECTION 101 IF
CENTERING TABLE 120 IS CLEAR.

ACTUATE CENTERING TABLE CONVEYOR 140
TO FEED TIRE ONTO CENTERING TABLE 120

ACTUATE CENTERING ARMS 161 AND TIRE
WIDTH SENSOR 195 TO MEASURE TIRE O.D.
AND WIDTH AND TO CENTER TIRE LATERALLY
ON CENTERING TABLE 120.

MOVE IMAGING SYSTEM CARRIAGE 340 AND
IMAGING SYSTEM SUB-SUB-CARRIAGE 420
TO CLEAR TIRE O.D. AND MAIN CONVEYOR 450

SET SPINDLE PRESSURE REGULATOR 559 FOR
TIRE SIZE ; MOVE POSITIONING SWITCH
ASSEMBLY 820 INTO POSITION ABOVE MAIN
CONVEYOR 450; MOVE X-RAY CARRIAGE 620
TO LOCATE X-RAY TUBE AT A POSITION
ABOVE THE EXPECTED MINIMUM TIRE I.D.;
OPEN DOORS 278.

MOVE IMAGE SYSTEM SUB-CARRIAGE 390 TO
PLACE IMAGE UNIT 440 AT 0° POSITION ;
MOVE X-RAY TUBE EMISSION APERTURE
703 TO 0° POSITION.

WHEN IMAGE UNIT 440 AT 0° POSITION THEN
ELEVATE OR LOWER THE MAIN CONVEYOR
450 AND THE CENTERING TABLE CONVEYOR
140 IN ACCORDANCE WITH TIRE WIDTH TO
POSITION CENTER PLANE OF TIRE IN PRE-
DETERMINED INSPECTION PLANE ; ACTUATE
SPINDLE CARRIAGES 510 TO RETRACT
SPINDLES 600.

*Fig. 27A*

ACTUATE CENTERING TABLE CONVEYOR 140 AND MAIN CONVEYOR 450 TO MOVE TIRE FROM CENTERING TABLE 120 ONTO MAIN CONVEYOR 450 AFTER: DOORS 278 ARE OPEN; LIMIT SWITCH 820 IS POSITIONED; X-RAY TUBE ASSEMBLY 700 AND IMAGING CARRIAGE 340 AT 0° POSITION; MAIN CONVEYOR 450 AND CENTERING TABLE 120 ARE POSITIONED; AND AFTER SPINDLES 600 ARE RETRACTED.

(K) ──────▶

POSITIONING SWITCH ASSEMBLY 820 SENSES ARRIVAL OF TIRE AT INSPECTION STATION AND MAIN CONVEYOR 450 IS SLOWED THEN STOPPED.

CLOSE DOORS 278

(L) ──────▶

MOVE SPINDLE CARRIAGES 510 TO VERTICALLY INSERT SPINDLES 600.

MOVE X-RAY SHIELD 750 TO UNCOVER X-RAY TUBE ASSEMBLY 700.

MOVE SPINDLE ARMS 550 TO EXPAND SPINDLES 600 AND INDICATE TIRE I.D.

DROP MAIN CONVEYOR 450 AND FRAMES 456; MOVE SPINDLE CARRIAGES TO SPREAD TIRE BEAD AS FUNCTION OF TIRE SIZE; ADJUST IMAGING UNIT 440 FOR FOCUS AS FUNCTION OF TIRE SIZE IF TIRE O.D. ABOVE A MAXIMUM O.D.

MOVE IMAGE SYSTEM CARRIAGE 340 TO POSITION CENTER OF ROTATION OF C-ARMS 380, 381 AT FOCAL POINT OF X-RAY TUBE.

Fig. 27B

IF X-RAY TUBE UNCOVERED, MOVE X-RAY SUB-SUB-CARRIAGE 680 TO LOWER TUBE

↓

IF TIRE I.D. IS GREATER THAN 13 INCHES, LOWER TUBE INTO TIRE ANNULUS BETWEEN TIRE BEADS. IF TIRE I.D. IS LESS THAN 13 INCHES, ACTUATE X-RAY SUB-CARRIAGE 660 FOR GEOMETRIC OFFSET.

↓

IF ALL THE ABOVE DONE, ACTUATE LIMITED SCHEDULED INTERRUPT, GIVING OPERATOR MANUAL CONTROL OF THE FOLLOWING TO EFFECT SCANNING.:

1. CONTROL OF SPEED AND DIRECTION OF ROTATION OF SPINDLES 600 TO ROTATE TIRE; ALSO CAN MOVE SPINDLE CARRIAGES 510 TO ADJUST BEADSPREAD.

2. MOVE X-RAY CARRIAGE 620, SUB-CARRIAGE 660 AND SUB-SUB-CARRIAGE 680 TO MOVE TUBE ASSEMBLY 700 TO DIRECT X-RAYS THROUGH PARTS OF TIRE TO BE SCANNED.

3. MOVE IMAGING SYSTEM CARRIAGE 340, SUB-CARRIAGE 390, AND SUB-SUB-CARRIAGE 420, TO TRACK X-RAYS FROM TUBE ASSEMBLY 700 AND CONTROL MAGNIFICATION.

↓

WHEN SCANNING COMPLETE, OPERATOR MANUALLY INITIATES AUTOMATIC RESUMPTION SIGNAL, WHICH STOPS ALL MOTION AND ALLOWS AUTOMATIC MODE TO BE RESUMED.

MOVE IMAGE SYSTEM CARRIAGE 340 AND IMAGE SYSTEM ASSEMBLY 440 TO CLEAR INSPECTED TIRE O.D. AND MAIN CONVEYOR; MOVE POSITIONING SWITCH ASSEMBLY AS FUNCTION OF SUBSEQUENT TIRE O.D. IF NEEDED; MOVE X-RAY SUB-CARRIAGE 660 TO STRAIGHTEN GEOMETRIC OFFSET; MOVE X-RAY CARRIAGE IN SO TUBE WILL CLEAR INSPECTED TIRE ACTUAL I.D. AND SUBSEQUENT TIRE MAXIMUM EXPECTED I.D.

↓

MOVE X-RAY PIVOT AND IMAGE SYSTEM SUB-CARRIAGE TO 0° AND MOVE SPINDLE CARRIAGE 510 TO INSERT SPINDLES TO 3.5" BEADSPREAD.

↓

WHEN X-RAY TUBE IS INSIDE INSPECTED TIRE I.D. AND IS PIVOTED TO 0°, AND WHEN IMAGE ASSEMBLY MOVED TO 0°, MOVE SPINDLE CARRIAGES TO FULLY INSERT SPINDLES AND ACTUATE X-RAY SUB-SUB-CARRIAGE TO RAISE X-RAY TUBE.

↓

MOVE IMAGE SYSTEM CARRIAGE AND ASSEMBLY TO CLEAR SUBSEQUENT TIRE O.D. AND MAIN CONVEYOR; RAISE FRAMES 456; POSITION MAIN CONVEYOR AND CENTERING TABLE FOR INSPECTED TIRE; COVER X-RAY TUBE.

↓

OPEN DOORS 278

↓

IF TUBE CLEARS INSPECTED TIRE I.D. RETRACT SPINDLES ENTIRELY BY MOVING SPINDLE ARMS 550.

↓

IF: SPINDLES FULLY RETRACTED; X-RAY TUBE IS UP; FRAMES 456 ARE UP; AND MAIN CONVEYOR IS POSITIONED FOR TIRE EXIT; THEN MOVE SPINDLE CARRIAGES 510 TO REMOVE SPINDLES.

SET SPINDLE PRESSURE FOR NEW
TIRE AND RETRACT SPINDLES.

↙ ↘

IF NO SUBSEQUENT TIRE IS TO BE ENTERED CONCURRENTLY WITH THE EXITING OF THE INSPECTED TIRE

↓

IF SPINDLES HAVE MOVED AND DOORS HAVE OPENED, MOVE INSPECTED TIRE OUT.

↓

REPOSITION MAIN CONVEYOR, CENTERING TABLE AND SPINDLES FOR SUBSEQUENT TIRE; POSITION LIMIT SWITCH AND IMAGE SYSTEM CARRIAGE AND ASSEMBLY TO CLEAR SUBSEQUENT TIRE O.D. AND MAIN CONVEYOR.

↓

MOVE SUBSEQUENT TIRE IN.

↓

TO "K" ON SHEET 2

---

IF A SUBSEQUENT TIRE IS TO BE ENTERED CONCURRENTLY WITH THE EXITING OF THE INSPECTED TIRE.

↓

REPOSITION MAIN CONVEYOR AND CENTERING TABLE IF REQUIRED AND IF POSSIBLE TO EXIT THE INSPECTED TIRE AND ENTER A SUBSEQUENT TIRE (EVEN IF SUBSEQUENT TIRE ENTERS BELOW CENTERLINE)

↓

IF: DOORS OPEN; POSITIONING SWITCH POSITIONED FOR SUBSEQUENT TIRE; SPINDLES RETRACTED; MAIN CONVEYOR AND CENTERING TABLE POSITIONED TO ENTER SUBSEQUENT TIRE AND EXIT INSPECTED TIRE; THEN MOVE INSPECTED TIRE OUT BY MAIN CONVEYOR, AND MOVE SUBSEQUENT TIRE IN SO LONG AS IMAGE SYSTEM CARRIAGE AND ASSEMBLY ARE POSITIONED FOR SUBSEQUENT TIRE; DELAY MOVEMENT OF SUBSEQUENT TIRE FOR 1 SEC. IF INSPECTED TIRE O.D. IS EQUAL TO OR GREATER THAN 40".

↓

REPOSITION MAIN CONVEYOR AND CENTERING TABLE TO CENTER SUBSEQUENT TIRE

↓

TO "L" ON SHEET 2

Fig 27E

TIRE INSPECTION SYSTEM

This is a division, of application Ser. No. 495,377, filed Aug. 7, 1974, now U.S. Pat. No. 4,088,936.

REFERENCE TO RELEVANT AND RELATED PATENTS OF APPLICATION

TIRE INSPECTION APPARATUS, Ser. No. 95,859 filed Dec. 7, 1970 by Anthony Palermo, Jr., issued Mar. 25, 1975 as Patent No. 3,873,837, here the "Tire Inspector Patent", the disclosure of which is incorporated by reference.

METHOD AND APPARATUS FOR INSPECTING TIRES, Ser. No. 254,939 filed May 19, 1972 by Richard L. T. Fox, issued Oct. 22, 1974 as Patent No. 3,843,888, here the "Tire Handling Patent".

TIRE INSPECTION SYSTEM, Ser. No. 495,379 filed Aug. 7, 1974 by Donald N. Heisner, here the "Systems Patent".

TIRE INSPECTION SYSTEM, Ser. No. 495,448 filed Aug. 7, 1974 by Donald N. Heisner and Phillip K. Loyer, here the "Operations Patent".

TIRE INSPECTION SYSTEM, Ser. No. 495,493 filed Aug. 7, 1974 by Phillip K. Loyer, here the "Mechanisms Patent".

TIRE INSPECTION SYSTEM, Ser. No. 495,447 filed Aug. 7, 1974 by Donald N. Heisner, Anthony J. Palermo and Phillip K. Loyer, here the "Shielded Structures Patent".

BACKGROUND OF THE INVENTION

1. Field of the Invention

The present invention relates to a tire inspection system including apparatus and methods for inspecting the integrity of tires through the use of penetrative emanation, such as X-radiation.

2. Background Terminology

Several terms of art are commonly used in conjunction with tires. The outer diameter or "O.D" of a tire is measured to an outer wear surface known as the tire "tread", even though it may be a smooth surface. The annular sides of a tire are called "sidewalls". The inner diameter or "I.D." of a tire is measured to sidewall portions called "beads". The axis about which a tire is intended to rotate, i.e., the axis common to both tire beads, is called the "central axis". A plane which extends perpendicular to the central axis and intersects the center of the tire tread is called the "central plane". The open space inside a tire and radially outwardly of the beads is called the "tire torus". The open space inside a tire which includes the torus and the space radially inwardly of the beads is called the "tire annulus". The distance from the outer surface of one sidewall to the outer surface of the other sidewall is called the "width" of the tire.

3. Prior Art

A number of proposals have been made for inspecting tires with X-rays and other penetrative emanation. Inspection with X-radiation has advantages over other known tire inspection methods, in that it provides information about the internal structure or integrity of a tire including a clear indication of whether internal components such as steel belts and the like are properly positioned and intact.

In the past, X-ray tire inspectors were used primarily as laboratory tools. Little use was made of X-ray inspection equipment on high rate production lines for a number of reasons including:

1. The inspection system was a relatively expensive piece of apparatus;
2. The apparatus could only inspect a limited number of tires from a production run due to its relatively slow operation;
3. A significant amount of tire handling and manipulation was typically required to position a tire in the apparatus for inspection; and,
4. After a tire was positioned for inspection, the apparatus was not capable of inspecting the total tire from bead to bead, without requiring that the tire be repositioned one or more times for successive inspection runs.

In view of these disadvantages, X-ray inspection of production tires was typically used either to inspect only selected portions of tires randomly sampled from a production run, or to inspect special duty tires such as are used on aircraft and on heavy duty, off-highway road equipment.

With the recent increased emphasis on vehicle safety, and the advent of steel belted tires, the need for X-ray inspection of all tires from a production run has become apparent. A number of proposals have been made to improve X-ray inspection apparatus, providing a capability to handle a large volume of tires of the same size from a production run.

A significant advance was made in tire inspection capability with the introduction of a rotatable X-ray tube, as described in the referenced Tire Inspector Patent. The rotatable tube permitted the complete inspection of a tire from bead to bead without requiring any reorientation of the tire or tube. With the tube located at a single position within or near the tire beads and with the tire rotating about its central axis, the tube is positioned to inspect one tire bead and is then scanned through a full arc inspecting tread, sidewalls and the other tire bead.

Still another advance was made with the introduction of a tire inspector having multiple-function tire supporting spindles, as described in the reference Tire Handling Patent. Two sets of spindles carried on separate carriages are inserted into the annulus of a tire to be inspected. The sets of spindles enter the tire axially from opposite sides. Once the spindles have entered the annulus, they move in directions parallel to the central plane to engage the tire beads. While the spindles continue to engage the tire beads, they are operable to support beads of the tire axially away from each other as may be required to facilitate inspection. The use of multi-function spindles has greatly simplified the manipulation of tires for inspection.

Despite the fact that several advances have been made in X-ray tire inspection, little has been done to satisfy the need for an X-ray tire inspector which is capable of efficiently, automatically and safely inspecting tires of a wide range of admixed sizes. Prior art inspection apparatus has not been well adapted to sequentially inspect tires of mixed sizes, and accordingly has not met the needs of a number of tire manufacturers whose production includes an admixture of tire sizes.

A recent proposal has suggested the use of a tire size sensing system for measuring tire O.D. and width before a tire is admitted to an enclosure for X-ray inspection. Once the measured tire has entered the enclosure which surrounds the X-ray inspection system, the tire tread is engaged by rotatable spools and is elevated to position its central plane in alignment with the center of the screen of an X-ray imaging system. An X-ray tube is then swung upwardly into the tire annulus and turned on to initiate the inspection. Inspection continues as the tire is rotated by the spools. The X-ray tube and the imaging system are mechanically coupled together so that both can be pivoted upwardly and downwardly to inspect the tire sidewalls.

This recent proposal has a number of disadvantages. Positioning of the tire for inspection continues to require a substantial amount of step-by-step tire manipulation. The tire is first engaged by spools. The tire is then elevated by the spools to an inspection level. Bead-spreaders are then inserted into one side of the tire torus and extended to spread the tire bead. Each of these steps must be performed in sequence, it being necessary for the tire to be raised into position before the beads can be spread. When these steps are completed, the X-ray tube is then swung into position from below.

Another disadvantage with this recent proposal is that X-ray tube operation must be terminated between tire inspections. Repeatedly energizing and de-energizing the tube and its associated generator equipment may add to the required inspection time and may also diminish the operating life of the X-ray tube.

Another disadvantage of previously proposed X-ray tire inspection apparatuses is their inflexibility of operation. While computers have been used to some extent to facilitate and speed up the operation of the apparatus, no use has been made of a programmable computer system to permit inspection cycles to be widely varied by altering the program, without the need for mechanical changes in the apparatus.

Still another disadvantage of prior proposed inspection apparatuses is that their several movable components are not independently operable and do not utilize servo-system technology to permit their operation to be controlled and monitored from a central control console. No thorough system of malfunction analysis has been provided on known tire inspectors.

The use which is made of computer systems in prior proposals includes the storage of sensed tire size data, and the subsequent control of the apparatus to inspect a tire of the sensed size. The computer is operated in an "open loop" fashion. Command signals are issued by the computer to components of the apparatus. If the components respond as intended, a proper inspection sequence is carried out.

The "open loop" mode of operation has several disadvantages. While the computer issues commands, it has no knowledge of whether the commands are properly executed. The computer cannot sense the conditions and positions of the components it commands and this makes it difficult to prevent the occurrence of potentially destructive or dangerous conditions. If the computer issues a defective command or if the apparatus improperly executed a command, potentially destructive or dangerous conditions can easily arise.

Still another disadvantage of "open loop" operation is that no use can be made of the computer to assist in analyzing a malfunction. When a defect arises, it is often difficult to diagnose, and substantial machine "down time" may result before the malfunction is analyzed and corrected.

Still another drawback of the proposed use of "open loop" computer control systems in tire inspectors is the failure of such systems to provide for human intervention in the inspection procedure. The operator cannot interrupt the procedure to change its sequence, or to skip certain steps, or to add certain steps, or to lengthen or shorten certain steps. The versatility of these proposed systems leaves much to be desired.

Summary of the Invention

The present invention overcomes certain of the foregoing and other drawbacks of the prior art and provides a novel and improved tire inspection system. The invention includes both method and apparatus features.

A significant advantage of apparatus constructed in accordance with the invention is its ability to adjust rapidly and automatically to the size of each tire fed to the machine for inspection. This capability enables the apparatus to inspect tires of a wide variety of sizes as they emerge from their respective production lines. Tires having an inner diameter as small as 10 inches can be accommodated at one end of the range. Tires having an outer diameter of 56 inches and weighing as much as about 750 pounds can be accommodated at the other end of the range. Moreover, the apparatus can accommodate tires one after the other which are at opposite extremes of this size range.

No manual adjustments to the apparatus or manual control of the inspection process are required unless the operator so desires. All the operator need do is to attend a control console to watch for tire flaws to appear on his TV monitor, and to monitor the operation of the apparatus in case some malfunction should be indicated on his control console. If the operator desires to interrupt the programmed sequence of operation, he may do so at any time to eliminate, add, shorten or lengthen steps.

The tire inspector is designed to be positioned between two conventional driven conveyor sections. Tires are fed one at a time from one of the conveyor sections onto a centering table. The centering table retains the tire for admission to a shielded enclosure which houses an inspection system. While the tire is on the centering table it is centered laterally by a pair of arms which move inwardly to engage opposite sides of the tire tread. The centering arms also serve as sensors to measure the outer diameter of the tire. Once the tire has been centered, a width sensor bar descends to measure the width of the tire.

The tire diameter and width information is transmitted to a control console where it is used in pre-positioning several movable components of the tire inspector to effect the most efficient handling of the tire. When a tire inspection already underway within the enclosure is completed, doors on opposite sides of the enclosure open to simultaneously discharge the inspected tire and admit the tire from the centering table.

As the tire to be inspected enters the enclosure, the conveyor system on which it travels is elevated or lowered as need be to position the tire with its center plane in a predetermined inspection plane. Before the tire reaches the inspection station, first and second sets of spindles on opposite sides of the tire are positioned to just clear the tire width for ready insertion into the tire. Similarly, the X-ray source and an X-ray sensitive receiving unit are moved to optimum positions which will clear the inner and outer tire diameters. A traveling positioning switch assembly moves to a position where it will stop the conveyor with the axis of the tire along a predetermined line. In short, by the time the tire reaches the inspection station, all is in readiness to receive the tire and to initiate its inspection.

As the tire reaches the inspection station, the doors to the shielded enclosure close. The sets of spindles carried on arms arranged in a cross-crossed, scissors fashion move axially into the tire and pivot laterally to engage the tire bead. Since the center plane of the tire is already aligned with the inspection plane, the tire need not be further moved to initiate inspection.

As soon as the spindles have engaged the tire beads, the output window of the X-ray tube is uncovered and the tube begins to move into the tire annulus. The main conveyor which carried the tire to the inspection station moves away from the tire, and sections of the main conveyor fold out of the way to provide space for full range movement of the receiving unit. The sets of spindles move away from each other a short distance to spread the tire beads. The movements of all these components are independently controlled and a number of the movements take place simultaneously to minimize set-up time.

In the preferred embodiment, the inspection system employs an X-ray source and an X-ray imaging unit. One feature of the apparatus is its use of a retractable X-ray tube which operates continuously to emit X-radiation. The tube does not shut down when retracted or when moving between its retracted and extended positions. A movable shield assembly covers the tube when it is retracted so the doors to the enclosure can be opened without leaking radiation. The tube is prevented from being uncovered when the doors are open, and the doors cannot be opened when the tube is uncovered.

The use of a continuously operating tube permits the use of a much less complicated generator system. If the tube were to turn off and on between inspection operations, the generator would have to be provided with a more complicated automatic system permitting its start-up in minimal time without drawing excessively high current. By running the tube continuously, a less complex, manual generator start-up system can be used and no time is lost between inspections waiting for warm-up of the X-ray system. Continuous tube filament operation may extend tube operating life in that it avoids the thermal shock of cooling down when turned off and heating up when turned on. Keeping the filament hot may make it less subject to breakage due to vibration since the filament is more ductile when hot.

Since the X-ray tube is operating at the time of its insertion into the tire, X-ray inspection is begun immediately. The spindles are rotated to revolve the tire. The imaging unit forms an image of tire portions being inspected on a control console screen.

When inspection is completed the imaging unit and the X-ray tube retract, the main conveyor repositions, the spindles retract, and the doors open to discharge the inspected tire and receive a subsequent tire.

The inspection cycle itself can be manually controlled from the console or can be carried through to completion by a programmed computer in the control console. Since all of the movements of the apparatus components are independently controllable from the control console, the operator can manually effect any operable program of inspection and the computer can likewise effect any operable program.

Several advantages are obtained by utilizing a closed loop computer control apparatus in combination with independently operable, servo-system controlled mechanism movements. First, the computer can be programmed to prevent operation of the apparatus in any manner that is potentially destructive to the apparatus or dangerous. In effect, the computer tells the operator what things he is allowed to do, and prevents the operator from doing destructive or dangerous things.

Another advantage is that the computer can be programmed to continuously monitor all machine functions. If any element moves or tries to move further than it should, or requires a longer period of time to move than it should, the computer shuts down the machine and provides a coded readout analyzing the malfunction for the operator. This system has been shown in tests to be very successful in preventing machine damage, facilitating repair of malfunctioning components, and in general substantially reducing machine down time.

The several referenced cases filed concurrently with this case relate to various aspects of the tire inspector and its operation. The lines of demarcation between these several cases exist principally due to the fact that different people and groups of people contributed inventive concepts during the overall development.

Certain basic concepts of the system were conceived initially by one inventor, and these concepts form the subject of the Systems Patent. Certain additional concepts together with ways of implementing the basic concepts were conceived jointly by two inventors, and these form the subject of the Operations Patent. Certain mechanisms and methods of operating these mechanisms were conceived by one inventor, and these form the subject of the Mechanisms Patent. The concept of using a shielded X-ray tube operating continuously within a shielded enclosure was developed jointly through the efforts of three inventors, and this forms the subject of the Shielded Structures Patent. The control system and its operation represents the work of two inventors, and forms the subject of the present case.

The computer control apparatus slows down the motion of movable components when the components are within a predetermined distance of a commanded position, or at one of the ends of its travel path. The control system also detects malfunctions in the tire inspection system and indicates on a display panel what the malfunctions are. The control apparatus maintains a constant positioned relation between the X-ray generator and the imaging system. The control apparatus also establishes a limited scheduled interrupt of the automatic mode, whereby the system suspends automatic operation at a predetermined point in the program, and turns over manual control to the operator several scanning functions. Upon completion of scanning, the automatic mode is resumed.

As will be apparent from the foregoing summary, it is a general object of the present invention to provide a novel and improved X-ray tire inspection system.

Other objects and a fuller understanding of the invention may be had by referring to the following description and claims taken in conjunction with the accompanying drawings.

BRIEF DESCRIPTION OF THE DRAWINGS

FIG. 4 is a perspective view of still another portion of the centering table, showing the centering arm assembly;

FIG. 5 is an enlarged top plan view of a portion of the centering arm assembly with portions broken away to illustrate details of construction;

FIG. 6 is a perspective view of still another portion of the centering table showing the height sensor mechanism;

FIG. 7 is an elevational view of a portion of the height sensor as seen from the plane indicated by the line 7—7 in FIG. 6;

FIG. 13 is a perspective view of the imaging system sub-carriage;

FIG. 14 is a cross-sectional view as seen from the plane indicated by the line 14—14 in FIG. 13;

FIG. 18 is a cross-sectional view as seen from the plane indicated by the line 18—18 in FIG. 17;

FIG. 19 is an enlarged cross-sectional view of one of the spindles as seen from the plane indicated by the line 19—19 in FIG. 17;

FIG. 21A is an enlarged top plan view of portions of the X-ray sub-carriage, X-ray sub-sub-carriage, and the spindles showing in solid lines the position of these components for insertion into a tire, and showing in phantom the internal diameters of the largest and smallest tires inspected by the system;

FIGS. 21B and 21C are schematic top plan views of tires positioned in the inspection station illustrating the path of movement of the X-ray tube focal spot after the X-ray tube has been inserted into such tire;

FIG. 22 is a perspective view of the traveling limit switch assembly;

FIG. 23A, 23B are schematic diagrams tabulating the several electrical inputs to the control console from limit switches and photocells;

Description of the Preferred Embodiment

Figure 1:
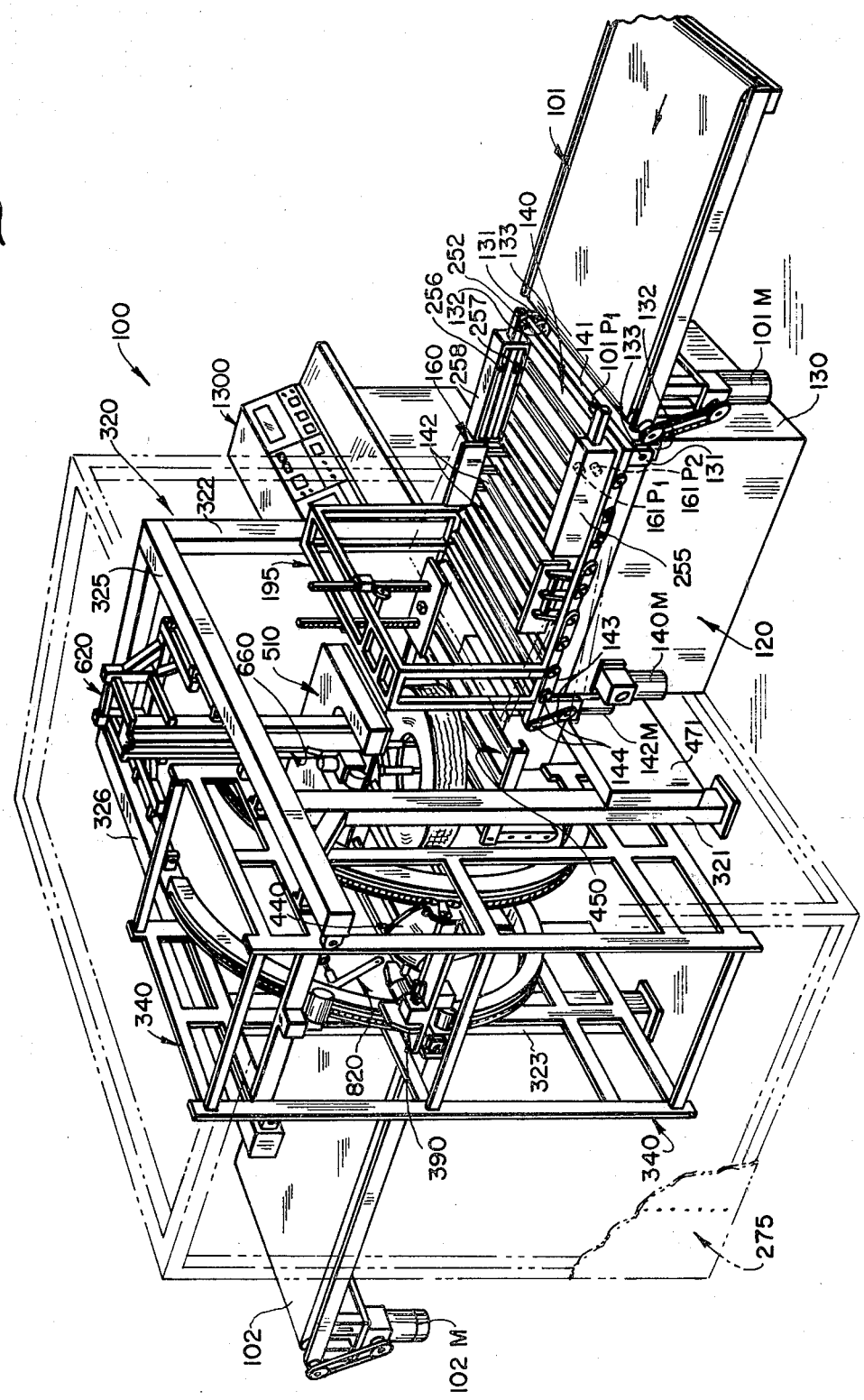
FIG. 1 is a perspective view of a tire inspector apparatus constructed in accordance with the present invention and showing the relative arrangement of the major components of the apparatus.

Referring to FIG. 1, a tire inspector apparatus is shown generally by the numeral 100. The apparatus 100 includes a shielded enclosure 275 which houses several automated components, as will be explained. A centering table 120 and a control console 1300 are positioned outside the enclosure 275.

The apparatus 100 is installed between two conventional belt conveyor sections 101, 102 driven, respectively, by motors 101M, 102M. The conveyor 101 is operated intermittently to deliver tires one at a time onto the centering table 120. Once a tire has been received on the centering table 120, its size is sensed and it is centered for admission to the enclosure 275. Once a tire has been admitted to the enclosure 275, it is spindled for rotation and X-ray inspected during rotation, as will be explained. Inspected tires are discharged from the enclosure 275 onto the conveyor section 102 which runs continuously. The operation of the apparatus 100 and the conveyor 101 is controlled from the control console 1300.

The description which follows is divided into several sections, each treating a specific portion of the apparatus 100. The latter sections describe the operation of the apparatus 100.

The Centering Table 120

The centering table 120 includes an upstanding frame 130 which underlies and supports a driven roller conveyor 140. The conveyor 140 includes a welded, generally rectangular frame 141 which journals opposite end regions of a plurality of cylindrical rolls 142. A motor 142M is drivingly connected to the rolls 142 by a series of roller chains 43 reeved around sprockets 144 to concurrently drive the rolls 142.

The right end of the roller conveyor 140, as viewed in FIG. 1, is pivotally connected to the upstanding frame 130. Depending flanges 131 carried on opposite sides of the conveyor frame 141 extend alongside upstanding flanges 132 carried on the right end region of the centering table frame 130. Pins 133 extend through aligned holes in the flanges 131, 132 to form a pivotal connection between the roller conveyor 140 and centering table frame 130.

Figure 3:
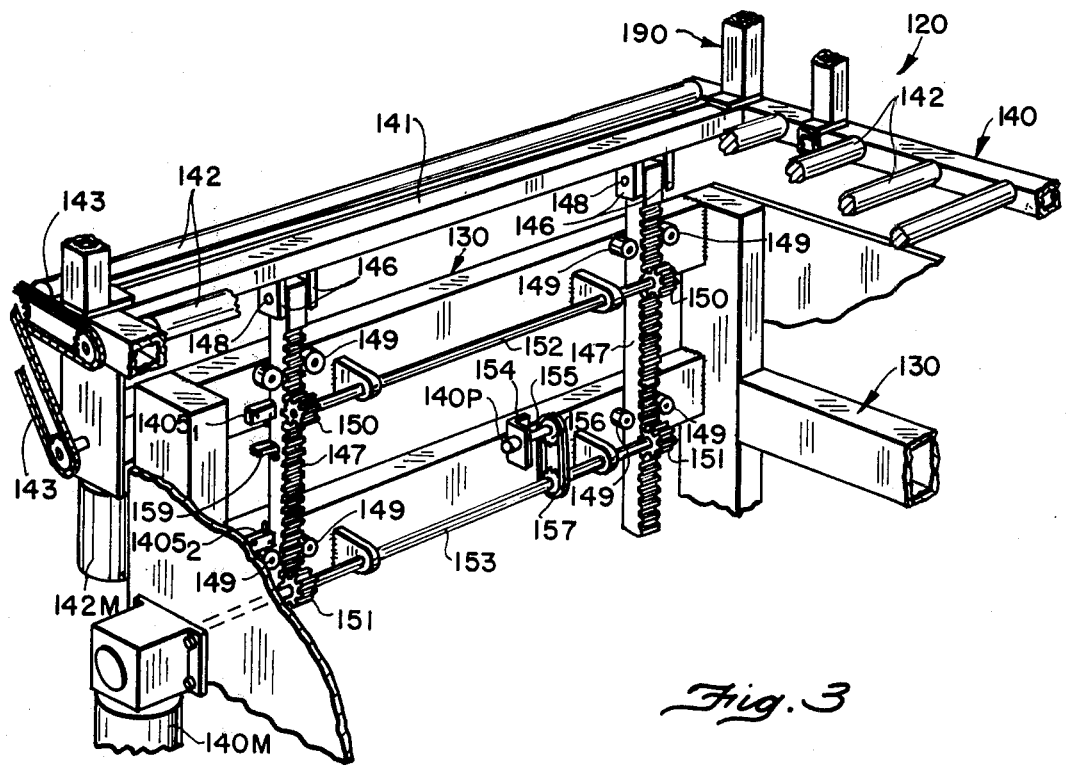
FIG. 3 is an enlarged perspective view of a portion of the centering table, showing the centering table elevation drive system.

The left end of the roller conveyor 140 can be raised and lowered relative to the centering table frame 130. Referring to FIG. 3, a rack and pinion drive system, indicated generally by the numeral 145, is interposed between the centering table frame 130 and the left end of the roller conveyor 140. Two pairs of spaced, depending flanges 146 are carried by the conveyor frame 141. A pair of vertically oriented gear racks 147 have upper end regions which extend between the spaced flanges 146. Pins 148 extend through aligned holes in the flanges 146 and the gear racks 147 to pivotally connect the gear racks 147 to the conveyor frame 141.

Guide rollers 149 rotatably mounted on the centering table frame 130 engage the gear racks 147 and confine their movement to vertical directions.

Two pairs of gears 150, 151 mesh with the gear racks 147. An idler shaft 152 rotatably carried by the frame 130 mounts the upper pair of gears 150 for concurrent rotation. A drive shaft 153 rotatably carried by the frame 130 mounts the lower pair of gears 151 for concurrent rotation. A motor 140M drivingly connects with the shaft 153.

Lowering and raising of the left end of the roller conveyor 140 is effected by the motor 140M. When the motor 140M rotates the drive shaft 153 in one direction, the meshing engagement between the gears 151 and the gear racks 147 will cause the left end of the conveyor 142 to raise. When the motor 140M drives the shaft 153 in the opposite direction, the left end of the conveyor 140 will lower.

The height of the left end of the conveyor 140 is monitored by a potentiometer 140P. The potentiometer 140P is carried by a bracket 154 secured to the centering table frame 130. The potentiometer 140P has a rotatable stem 155 which carries a sprocket 156. A roller chain 157 is reeved around the sprocket 156 and around a drive sprocket 157 carried on the drive shaft 153. Rotation of the drive shaft 153 by the motor 140M effects concurrent rotation of the potentiometer stem 155. A suitable electrical cable (not shown) connects the potentiometer 140P with the control console 1300. The potentiometer 140P provides a resistance which varies to provide a variation in a signal voltage indicating the height of the conveyor 140.

A pair of limit switches $140S_1$, $140S_2$ are provided to sense when the left end of the conveyor 140 is at the lowermost and uppermost ends of its range of travel. The switches $140S_1$, $140S_2$ are supported on the frame 130. An arm 159 secured to one of the gear racks 147 selectively engages one of the switches $140S_1$, $140S_2$ when the conveyor 140 is at the upper or lower ends of its range of travel. The switches $140S_1$, $140S_2$ are each electrically connected by suitable conductors (not shown) to the console 1300 to provide a step variation in a signal voltage.

The Centering Table Centering Mechanism 160

A centering mechanism, indicated generally by the numeral 160 in FIGS. 1 and 4, is provided to laterally center tires on the conveyor 140 for admission to the shielded enclosure 275. The centering mechanism 160 is carried on the conveyor frame 141 for movement with the conveyor frame 141 as the conveyor 140 pivots about the pins 133 connecting its right end with the centering table frame 130.

Referring to FIG. 4, a pair of spaced upstanding arm assemblies 161 are carried on opposite sides of the roller conveyor 140. The arm assemblies 161 are movable toward and away from each other to engage and disengage opposite sides of a tire received on the centering table 120. The arm assemblies 161 include support plates 162 carried on brackets 163. The brackets 163 depend between some of the rolls 142. Lower end regions of the brackets 163 connect with a pair of supports 164.

A guide rod 167 is supported at opposite ends by the conveyor frame 141. The supports 164 are slidably carried on the guide rod 167. A threaded rod 169 is journaled for rotation near opposite ends by bearing blocks 170 secured to the conveyor frame 141. The threaded rod 169 has right hand threads 169R which drivingly connect with one of the arm assemblies 161, and left hand threads 169L which drivingly connect with the other arm assembly 161. When the rod 169 is rotated in one direction, the arm assemblies 161 move toward each other. When the rod 169 is rotated in the other direction, the arm assemblies 161 move away from each other.

A timing belt pulley 171 and a sprocket 172 are secured to one end region of the threaded rod 169. A toothed timing belt 173 is reeved around the pulley 171 and around a pulley 174 carried on one end of a stub shaft 175. A bearing block 176 journals the stub shaft 175. A V-belt pulley 177 is carried on the other end region of the stub shaft 175.

A reversible centering arm drive motor 161M is provided to rotate the threaded rod 169. A V-belt 178 is reeved around a pulley 179 carried on the drive shaft of the motor 161M, and around the pulley 177. The belts 173, 178 drivingly connect the motor 161M to the threaded rod 169 to move the centering arms 161 toward and away from each other.

A roller chain 180 is reeved around the sprocket 172 and around a sprocket 181 carried on one end region of a shaft 182. The shaft 182 extends across the width of the frame 141. A pair of bearing blocks 183 (only one is shown in FIG. 4) are secured to opposite sides of the frame 141 to journal the shaft 182.

The shaft 182 provides a drive on opposite sides of the conveyor 140 for a movable photocell sensing system, as will be described. Identical chain drives connect with the shaft 182 on opposite sides of the conveyor 140 to drive this photocell system. Only one of these drives is shown in FIG. 4 as including a sprocket 184 carried on the shaft 182, a sprocket 187 rotatably carried on the conveyor frame 141, and a roller chain 185 reeved around the sprockets 184, 187. Identical sprockets 184, 187 and an identical roller chain 185 (not shown) are provided on the opposite side of the conveyor 140.

The inward and outward positioning of the centering arms 161 is monitored by a potentiometer 161P. The potentiometer 161P is carried by a bracket 189 secured to the frame 141. The potentiometer 161P has a rotatable stem which carries a sprocket 186. A roller chain 188 is reeved around the sprocket 186 and around a drive sprocket 187a connected to one of the sprockets 187. Rotation of the sprocket 187a by the motor 161M effects concurrent rotation of the stem of the potentiometer 161P. A suitable electrical cable (not shown) connects the potentiometer 161P with the control console 1300. The potentiometer 161P provides a resistance which varies to provide a variation in a signal voltage indicating the position of the centering arms 161.

A pair of limit switches $161S_1$, $161S_2$ are provided to sense when the centering arms 161 are at the inward and outward ends of their range of travel. The switches $161S_1$, $161S_2$ are supported on the frame 141, and are selectively engaged by one of the supports 164 when the centering arms 161 are at the inward or outward ends of their range of travel. The switches $161S_1$, $161S_2$ are electrically connected by suitable conductors (not shown) to the control console 1300 to provide a step variation in a signal voltage.

Referring to FIG. 5, each of the centering arm assemblies 161 carries a movable sensing plate 190. Projections 162a, 190a formed on the plates 162, 190 extend toward each other and are connected by pins 191 to form a pivotal connection between lower regions of the plates 162, 190. Cap screws 192 extend through slots 162b formed in the plates 162 and are threaded into the plates 190 to limit the relative pivotal movement of the plates 162, 190 in directions away from each other. Compression coil springs 193 carried on the cap screws 192 bias the plates 162, 190 away from each other.

The centering arm assemblies 161 carry limit switches $190S_1$, $190S_2$. The switches $190S_1$, $190S_2$ are carried on brackets 194 secured to the plates 162. The switches $190S_1$, $190S_2$ have actuating plungers which project through apertures in the plates 162 and into engagement with the plates 190. When the plates 190 engage a tire positioned on the conveyor 140, the plates 190 pivot toward the plates 162 actuating the switches $190S_1$, $190S_2$. The switches $190S_1$, $190S_2$ are electrically connected in series and are connected by suitable conductors (not shown) to the control console 1300 to provide a step variation in a signal voltage.

The Centering Table Tire Width Sensor Mechanism

The width of a tire received on the centering table 120 is sensed by a tire width sensor assembly 195. Referring to FIGS. 1 and 6, the width sensor assembly 195 has an upstanding frame including four legs 196 welded to the conveyor frame 141 for movement with the conveyor frame 141 as the conveyor 140 pivots about the pins 133 connecting its right end with the centering table frame 130.

Two laterally extending members 197 are welded between the legs 196. Four cross bars 198, 199, 200, 201 are welded between the members 197. Two depending bars 202, 203 have their upper ends welded to the members 197. A cross bar 204 is welded to the depending bars 202, 203 and has opposite end regions which project beyond the sides of the depending bars 202, 203. Mounting blocks 205 are welded to the members 196, 197 at positions above the cross bar 204.

A sensor bar 210 is movably carried at a laterally centered position overlying the roller conveyor 140. The sensor bar 210 includes a rigid plate 211 supported on two spaced, upstanding gear racks 212, 213. A pair of roller bearing assemblies 214, 215 are secured to the cross bar 204 and to the mounting blocks 205, respectively. The roller bearing assemblies 214, 215 engage the gear racks 212, 213 and act as guides limiting the movement of the gear racks to travel in vertical directions.

A pair of gears 216, 217 mate with the gear racks 212, 213. The gears 216, 217 are secured to opposite end regions of a shaft 218. A pair of bearing blocks 219, 220 carried on the depending bars 202, 203 journal the shaft 218 for rotation. Another pair of bearing blocks 221, 222 carried on two the legs 196 journal an idler shaft 223. A pair of sprockets 224, 225 are carried on the shafts 128, 223 respectively. A roller chain 226 is reeved around the sprockets 224, 225. Movement of the roller chain 226 rotates the shafts 218, 223 together with the gears 216, 217, causing the gear racks 212, 213 to raise and lower the plate 211.

Raising and lowering of the plate 211 is effected by a pneumatic motor 190M. The motor 190M includes a cylindrical tube 230 supported near opposite ends on the cross bars 199, 200. A piston 231 is movably mounted in the tube 230. A pair of pulleys 232 are positioned on opposite ends of the tube 230. A flexible cable 223 is reeved around the pulleys 232 and connects with the piston 231. When pressurized air is admitted to the tube 230 on one side or the other of the piston 231, the piston 231 will move through the tube 230, causing the cable 233 to rotate the pulleys 232. A connector block 234 connects the cable 233 to the roller chain 226. When the piston 231 moves the cable 233, the chain 226 will move causing the gear racks 212, 213 to move vertically.

The vertical positioning of the sensor bar 210 is monitored by a potentiometer 195P. A bracket 235 mounts the potentiometer 195P on one of the legs 196 below the bearing block 221. The potentiometer 195P has a rotatable stem 236 which carries a sprocket 237. A roller chain 238 is reeved around the sprocket 237 and around a sprocket 239 carried on the idler shaft 223. As the idler shaft 223 rotates in response to movement of the chain 226, the potentiometer stem 236 is concurrently rotated to vary the resistance of the potentiometer 195P. A suitable electrical cable (not shown) connects the potentiometer 195P to the control console 1300 to provide a variation in a signal voltage indicating the position of the sensor bar 210. When the sensor bar 210 has been lowered into engagement with a tire positioned on the centering table 120, the potentiometer 195P provides an indication to the computerized control console 1300 of the width of the tire.

The sensor bar 210 carries a limit switch $195S_1$ which senses when the sensor bar has engaged a tire positioned on the centering table. Referring to FIG. 7 a plate 240 has its left end pivotally connected to the plate 211. A bracket 241 is secured to one end region of the plate 240 and is pivotally connected to one end region of the plate 211. The bracket 241 carries a stop (not shown) which prevents the plates 211, 240 from pivoting away from each other to a greater extent than is shown in FIG. 7. A compression coil spring 242 is interposed between the opposite end regions of the plates 211, 240 to bias the plates 211, 240 away from each other. A bracket 243 mounts the limit switch 195S1 atop the plate 211. The limit switch 195S1 has an actuating lunger 244 which depends through a hole 245 in the plate 211. The bottom end of the plunger 244 engages the top surface of the plate 240.

When the sensor bar 120 is lowered into engagement with a tire positioned on the centering table, the plate 240 pivots upwardly moving the plunger 244 and actuating the limit switch 195S1 to provide a step variation in a signal voltage. A suitable electrical cable (not shown) connects the switch 195S1 to the control console 1300.

Centering Table Conveyor Controls

Referring to FIG. 6, two photocells 142P1, 142P2 are carried on one of the legs 196 opposite two light sources 250, 251 carried another of the legs 196. Suitable electrical cables (not shown) connect the photocells 142P1, 142P2 to the control console 1300 to provide step variations in a signal voltage to indicate the presence or absence of an object between one or both of the light sources 250, 251 and their associated photocells 141P1, 141P2. As will be explained in greater detail, when a tire is received on the centering table conveyor 140, the conveyor rolls 142 continue to drive until the tire interrupts one or both of the light beams received by the photocells 142P1, 142P2. When either or both of the photocells 142P1, 142P2 sense the presence of a tire, the conveyor drive motor 142M is de-energized.

Referring to FIG. 1, a stationary photocell $101P_1$ is supported on the frame 141 near the right end of the roller conveyor 140. A light source 252 is supported on the frame 141 opposite the photocell $101P_1$. The photocell 101P₁ is connected through suitable electrical cables (not shown) to the control console 1300 to provide a step variation in a signal voltage indicating of the presence or absence of a tire on the conveyor section 101. The conveyor drive motor 101M is controlled at the control console 1300 in response to signals from the photocell 101P₁ to stop and start the conveyor 101 at appropriate times to effect feeding of the tires one at a time onto the centering table conveyor 140.

Referring to FIGS. 1 and 4, two movable photocells 161P₁, 161P₂ are carried in a housing 255 on one side of the conveyor 140. A corresponding pair of movable light sources 256, 257 carried in a housing 258 on the opposite side of the conveyor 140. A pair of brackets 259, 260 support the photocells 161P₁, 161P₂, and the light sources 256, 257 respectively.

A similar pair of brackets 259 (only one is shown in FIG. 4) are provided on opposite sides of the conveyor 140 to movably mount the photocells 161P₁, 161P₂ and the light source 256, 257 for concurrent movement. The brackets 259 are each slidably carried on a pair of guide rods 261 which extend longitudinally of the conveyor 140. The brackets 259 are secured to the roller chains 185 for movement in response to operation of the centering arm drive motor 161M. Suitable electrical cables, not shown, connect the photocells 161P1, 161P2 to the control console 1300 to provide step variations in a signal voltage indicating the presence or absence of an object between one or both of the light sources 256, 257 and their associated photocells 161P1, 161P2.

In operation, the photocells 161P1, 161P2 and the light sources 256, 257 move toward the shielded enclosure 275 when the centering arms 161 move toward each other, and vice versa. The light beams which extend from the sources 256, 257 toward the photocells 161P1, 161P2 will not be interrupted if a tire is properly positioned between the centering arms 161. If the light beams are interrupted, certain indicator lights are illuminated on a fault detection display on the control console 1300, as will be explained, to indicate that a malfunction has occurred.

The Shielded Enclosure 275

Figure 8:
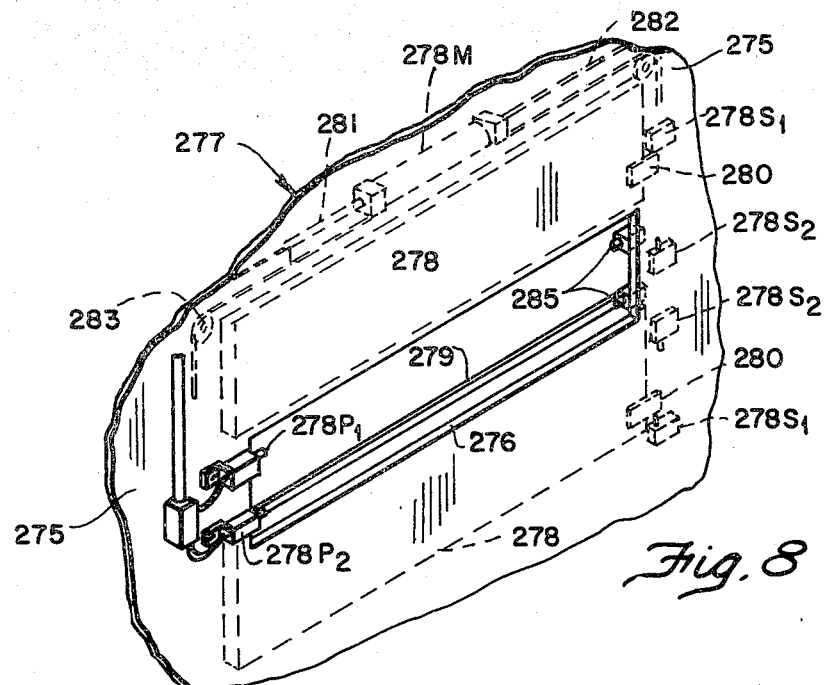
FIG. 8 is a perspective view of a portion of the shielded enclosure showing the opening through which tires are admitted to the enclosure, as seen from outside the shielded enclosure.
Figure 9:
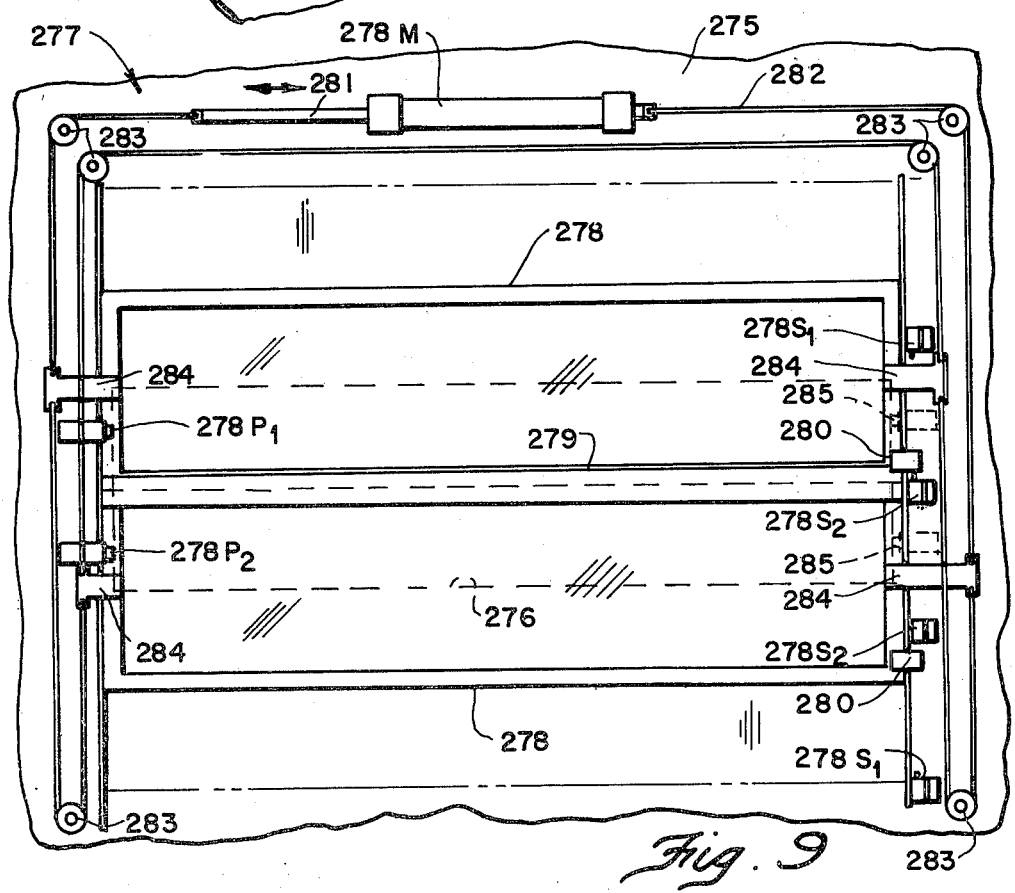
FIG. 9 is an enlarged plan view of the outlet door assembly as viewed from inside the shielded enclosure.

The shielded enclosure 275 has walls formed from lead-lined steel to prevent the escape of X-radiation from inside the enclosure. Identical inlet and outlet openings 276 are formed on opposite sides of the enclosure. FIG. 8 shows the inlet opening 276 as viewed from outside the enclosure 275. FIG. 9 shows the outlet opening 276 as viewed from inside the enclosure 275.

Identical door assemblies 277 including pairs of doors 278 are provided inside the enclosure 275 to concurrently open and close the openings 276. The doors 278 are vertically movable and include an upper door and a lower door associated with each of the openings 276. The lower doors each carry an upstanding lip 279 which overlaps the line of juncture between the upper and lower doors when the doors 278 are closed to prevent radiation leakage.

Each of the doors 278 carries an arm 280. Two limit switches 278S₁, 278S₂ are associated with each arm 280. The limit switches 278S₁, 278S₂ are selectively engaged by the arms 280 when the doors 278 are open or closed.

A pneumatic motor 278M is associated with each door assembly 277 to open and close the doors 278. The motor 278M has a piston 281 which moves axially depending on which end region of the motor 278M is supplied with pressurized air. Each door assembly 277 has a cable 282 with opposite ends connected to opposite ends of the piston 281. Intermediate portions of the cables 282 are reeved around pulleys 283 carried on the inner wall of the enclosure 275. Each of the doors 278 carries two brackets 284 which connect with the cables 282 to open and close the doors 278 in response to axial movement of the pistons 281 in the motors 278M.

A pair of photocells 278P₁, 278P₂ is associated with each of the door assemblies 277. The photocells 278P₁, 278P₂ associated with the inlet opening 276 are mounted outside the enclosure 275, as shown in FIG. 8. The photocells 278P₁, 278P₂ associated with the outlet opening 276 are mounted inside the enclosure, as shown in FIG. 9. A light source 285 is provided for each of the photocells 278P₁, 278P₂ on the opposite side of the opening 276 from its associated photocell. The light sources 285 associated with the inlet opening 276 are inside the enclosure 275. The light sources 285 associated with the outlet opening 276 are outside the enclosure 275.

When the doors 278 are open, the photocells 278P₁, 278P₂ receive light from the sources 285. Suitable electrical cables (not shown) connect the photocells 278P₁, 278P₂ to the control console 1300 to provide step variations in a signal voltage indicating the presence or absence of an object between one or more of the light sources 285 and their associated photocells 278P₁, 278P₂. If the photocells 278P₁, 278P₂ do not receive light from the sources 285 at a time when the doors 278 are to be moved from an open to a closed position, the doors 278 are prevented from closing, as will be explained.

The Main Frame 320

Figure 10:
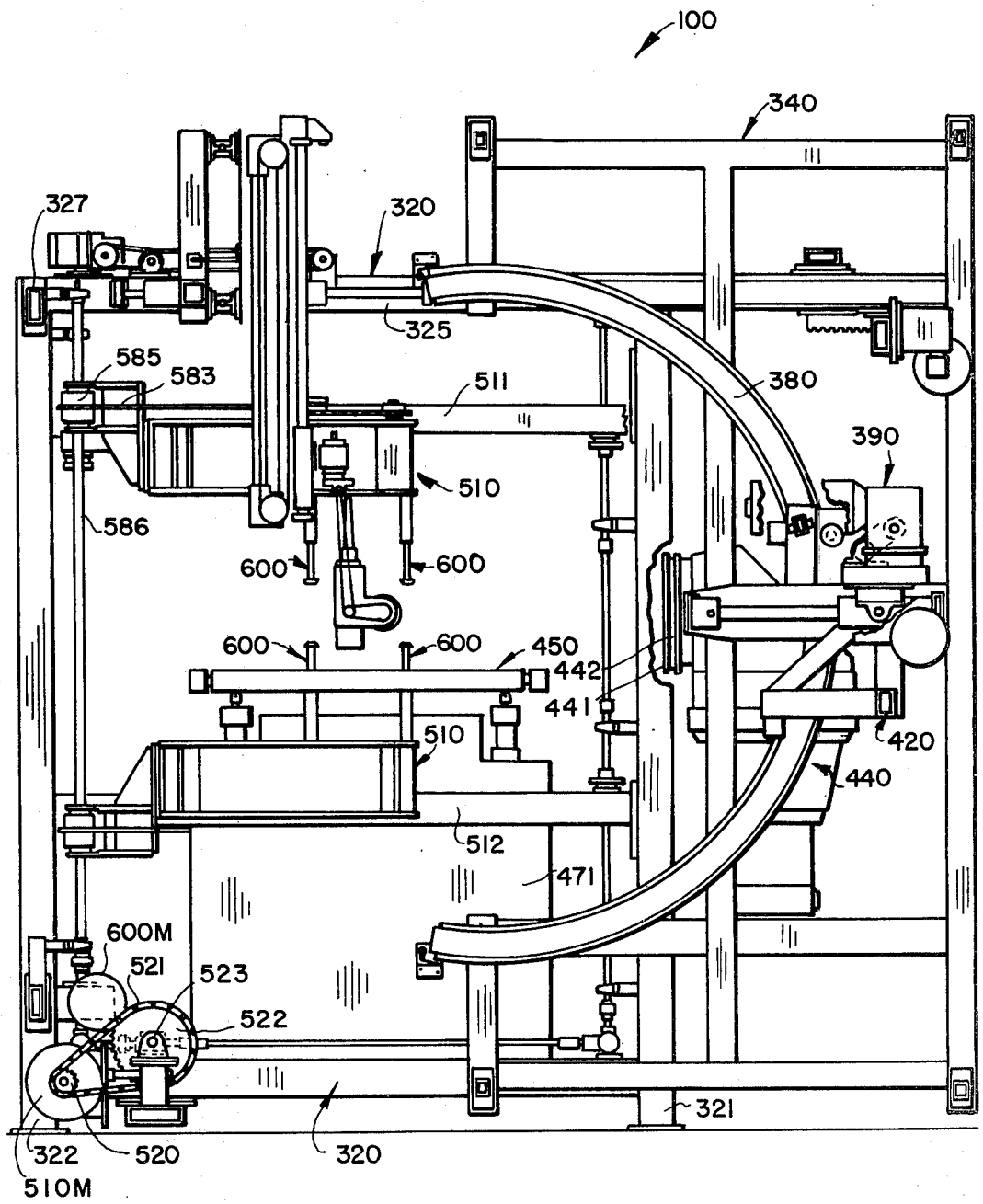
FIG. 10 is an elevational view of portions of the tire inspector apparatus showing the relative arrangement of several of its components.
Figure 11:
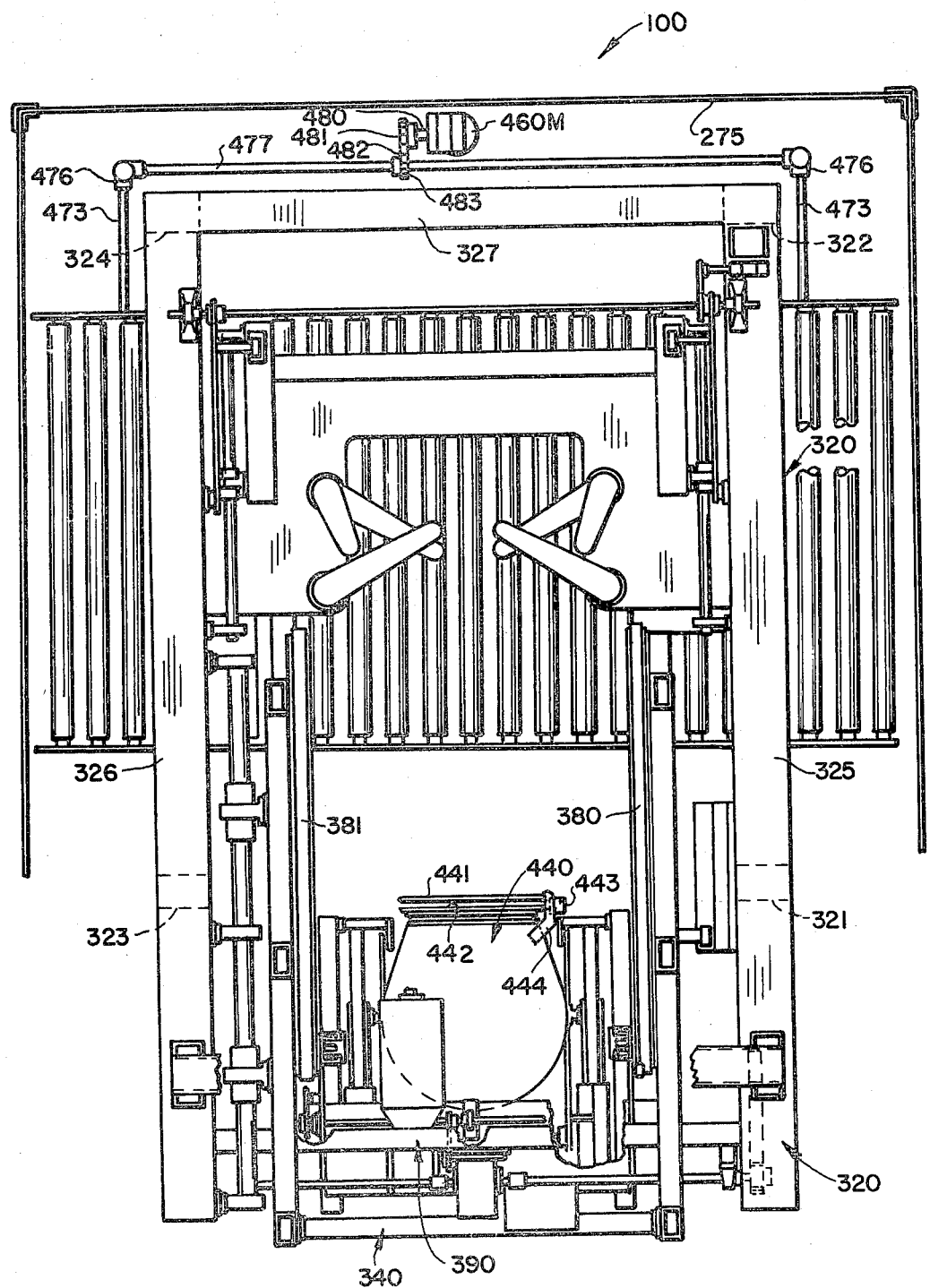
FIG. 11 is a top plan view of portions of the tire inspector apparatus showing the relative arrangement of several of its components.

Referring to FIGS. 1, 10 and 11, a main frame 320 includes four upstanding columns 321, 322, 323, 324. A pair of beams 325, 326 are mounted atop the columns 321, 322 and 323, 324.

The side of the main frame 320 defined by the columns 321, 322 and the beam 325 will be referred to as the "first side." The side defined by the columns 323, 324 and the beam 326 will be called the "second side." The side defined by the columns 322, 324 will be referred to as the "back side" or "rear" of the main frame 320. The side defined by the columns 321, 323 is considered to be the "front."

The first and second sides of the main frame are of substantially identical construction, one being the mirror image of the other. Several cross members, one of which is indicated by the numeral 327, interconnect the first and second sides to form a rigid frame.

The Imaging System Carriage 340

Figure 12:
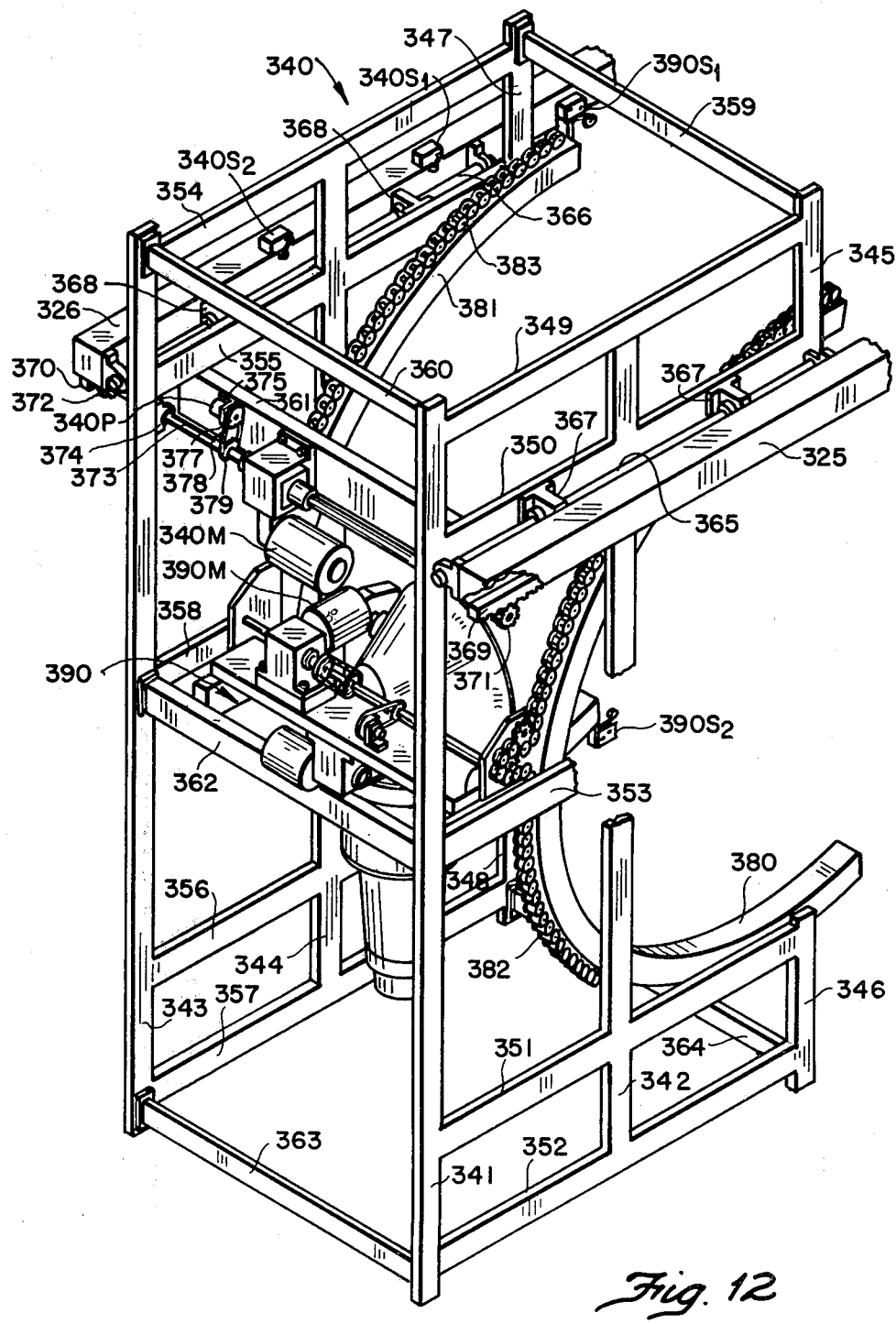
FIG. 12 is a perspective view of the imaging system carriage.

Referring to FIG. 12 in conjunction with FIGS. 1, 10, and 11, an imaging system carriage 340 is movably supported on the main frame 320. The carriage 340 is a welded structure including four full length uprights 341, 342, 343, 344 and four shorter uprights 345, 346, 347, 348. The uprights 341, 342, 345, 346 are interconnected by four full length members 349, 350, 351, 352 and by a shorter member 353, to define a first side of the carriage 340. The uprights 343, 344, 347, 348 are interconnected by four full length members 354, 355, 356, 357 and by a shorter member 358, to define a second side of the carriage 340. Six cross members 359, 360, 361, 362, 363, 364 extend between the first and second sides of the carriage 340 to form a rigid carriage structure.

The carriage 340 is positioned between the main frame beams 325, 326 with the side members 350, 355 paralleling the beams 325, 326. A pair of guide rods 365, 366 are carried by the beams 325, 326. Two pairs of bearing blocks 367, 368 are carried on the side members 350, 355. The bearing blocks 367, 368 slidably receive the guide rods 365, 366 to movably mount the imaging system carriage 340 on the main frame beams 325, 326.

A pair of gear racks 369, 370 are carried on the main frame beams 325, 326. A pair of gears 371, 372 carried on a shaft 373 mesh with the toothed gear racks 369, 370. The shaft 373 is journaled by a pair of bearing blocks 374 carried on the carriage uprights 341, 343. A reversible drive motor assembly 340M carried on the cross member 361 drivingly connects with the shaft 373 to move the imaging system carriage 340 inwardly and outwardly along the main frame beams 325, 326.

The inward and outward position of the imaging system carriage 340 is monitored by a potentiometer 340P. The potentiometer 340P is carried by a bracket 375 secured to the cross member 361. The potentiometer 340P has a rotatable stem 376 which carries a sprocket 377. A roller chain 378 is reeved around the sprocket 377 and around a drive sprocket 379 carried on the shaft 373. Rotation of the shaft 373 by the motor 340M effects concurrent rotation of the potentiometer stem 376. A suitable electrical cable (not shown) connects the potentiometer 340P with the control console 1300. The potentiometer 340P provides a resistance which varies to provide a variation in a signal voltage indicating the position of the imaging system carriage 340.

A pair of limit switches $340S_1$, $340S_2$ are provided to sense when the imaging system carriage 340 is at the inner and outer ends of its range of travel. The switches $340S_1$, $340S_2$ are supported on the main frame beam 326. One of the bearing blocks 368 selectively engages one of the switches $340S_1$, $340S_2$ when the imaging system carriage 340 is at the inner or outer ends of its range of travel. The switches $340S_1$, $340S_2$ are electrically connected by suitable conductors (not shown) to the control console 1300 to provide a step variation in a signal voltage.

Two C-shaped arms 380, 381 are carried by the imaging system carriage 340. The C-shaped arms define a pair of curved trackways which, as will be explained, support and guide the movement of an imaging system sub-carriage 390. A pair of roller chains 382, 383 extend along the outer surfaces of the C-arms 380, 381. Opposite ends of the roller chains 382, 383 are secured by brackets (not shown) to the end regions of the C-arms 380, 381.

The Imaging System Sub-Carriage 390

Referring to FIGS. 12 and 13, an imaging system sub-carriage 390 is carried on the C-arms 380, 381. The sub-carriage 390 includes a welded base formed from two spaced, parallel arms 391, 392 connected by a plate 393. A pair of upstanding brackets 395, 396 and a pair of depending brackets 397, 398 are welded to the arms 391, 392. The brackets 395, 396, 397, 398 carry rollers 399 which engage the C-arms 380, 381 to movably mount the sub-carriage 390 on the C-arms 380, 381.

The upstanding brackets 395, 396 each rotatably mount a pair of idler sprockets 401. A drive shaft 402 is journaled by the brackets 395, 396. A pair of drive sprockets 403 are carried on opposite end regions of the drive shaft 402. The roller chains 382, 383 are reeved around the idler sprockets 401 and around the drive sprockets 403, as best seen in FIG. 13.

A reversible drive motor assembly 390M is mounted on the plate 393. The motor assembly 390M has an output shaft 404 which carries a sprocket 405. A roller chain 406 is reeved around the sprocket 405 and around a sprocket 407 carried on the shaft 402. When the motor 390M drives the shaft 402 in one direction, the sub-carriage 390 moves up the C-arms 380, 381. When the shaft 402 is driven in the opposite direction, the sub-carriage 390 moves down the C-arms 380, 381.

The position of the sub-carriage 390 along the C-arms 380, 381 is monitored by a potentiometer 390P. The potentiometer 390P is carried by a bracket 408 secured to the plate 393. The potentiometer 390P has a rotatable stem 409 which carries a sprocket 410. A roller chain 411 is reeved around the sprocket 410 and around a drive sprocket 412 carried on the drive shaft 402. Rotation of the drive shaft 402 by the motor 390M effects concurrent rotation of the potentiometer stem 409. A suitable electrical cable (not shown) connects the potentiometer 390P with the control console 1300. The potentiometer 390P provides a resistance which varies to provide variation in a signal voltage indicating the position of imaging system sub-carriage 390 along the C-arms 380, 381.

Referring to FIG. 12, a pair of limit switches $390S_1$, $390S_2$ are provided on opposite ends of the C-arms 381 to sense when the imaging system sub-carriage 390 is at the upper and lower ends of its range of travel. The switches $390S_1$, $390S_2$ are selectively engaged by the brackets 396, 398 when the sub-carriage 390 is at the upper or lower ends of its range of travel. The switches $390S_1$, $390S_2$ are electrically connected by suitable conductors (not shown) to the control console 1300 to provide a step variation in a signal voltage.

A pair of guide rods 415, 416 are supported by the sub-carriage arms 391, 392. The guide rods 415, 416 extend parallel to the arms 391, 392 and serve to movably support an imaging system sub-sub-carriage 420.

The Imaging System Sub-Sub-Carriage 420

Referring to FIGS. 13 and 14, the sub-sub-carriage 420 includes a welded framework formed by a pair of uprights 421, 422, a pair of arms 423, 424, a pair of brace members 425, 426 and a cross member 427. A pair of lineal bearings 417, 418 slidably receive the guide rods 415, 416 to movably mount the sub-sub-carriage 420 on the arms 391, 392 of the sub-carriage 390.

A pair of idler sprockets 428 are rotatably mounted on the sub-carriage arms 391, 392. A pair of roller chains 429 are reeved around the sprockets 428 and around a pair of sprockets 430 (only one is shown in FIG. 14) carried on opposite end regions of a shaft 431. A pair of brackets 432 carried on the bearings 429, 430 connect with the roller chains 429.

A reversible drive motor assembly 420M is secured to the underside of the plate 393. The motor 420M has an output shaft 431a which carries a sprocket 431b. A roller chain 433 is reeved around the sprocket 431b and around a sprocket 434 carried on the shaft 431. When the motor 420M drives the shaft 431 in one direction, the sub-sub-carriage 420 moves inwardly along the guide rods 415, 416. When the shaft 431 is driven in the other direction, the sub-sub-carriage 420 moves outwardly along the guide rods 415, 416.

The position of the sub-sub-carriage 420 is monitored by a potentiometer 420P. The potentiometer 420P is carried by a bracket 435 secured to the underside of the plate 393, as best seen in FIG. 13. The potentiometer 420P has a rotatable stem 436 which is connected to the motor output shaft 431a. A suitable electrical cable (not shown) connects the potentiometer 420P with the control console 1300. The potentiometer 420P provides a resistance which varies to provide a variation in a signal voltage indicating the position of the sub-sub-carriage 420 along the guide rods 415, 416.

A pair of limit switches 420S1, 420S2, are provided to sense when the sub-sub-carriage 420 is at the inner and outer ends of its range of travel. The switches 420S1, 420S2 are supported on the sub-carriage arm 392. The switches 420S1, 420S2 are selectively engaged by the bearing 430 carried on the guide rod 415 when the sub-sub-carriage 420 is at the inner or outer ends of its range of travel. The switches 420S1, 420S2 are electrically connected by suitable conductors (not shown) to the control console 1300 to provide a step variation in a signal voltage.

The Imaging Unit 440

An imaging unit 440 is carried on the sub-sub-carriage 420. The imaging unit 440 is a conventional imaging system of the type which is capable of producing an output signal representative of an image formed by X-radiation which has passed through a tire being inspected and is received on imaging screen 442.

In the preferred embodiment, the imaging unit 440 is an imaging system of the type sold by Old Delft Corporation of America, Fairfax, Va. 22030, under the trademark DELCALIX with 12½ inch screen and ISOCON type S video tube. Suitable electrical conductors (not shown) connect the imaging unit 440 with the control console 1300.

Figure 14A:
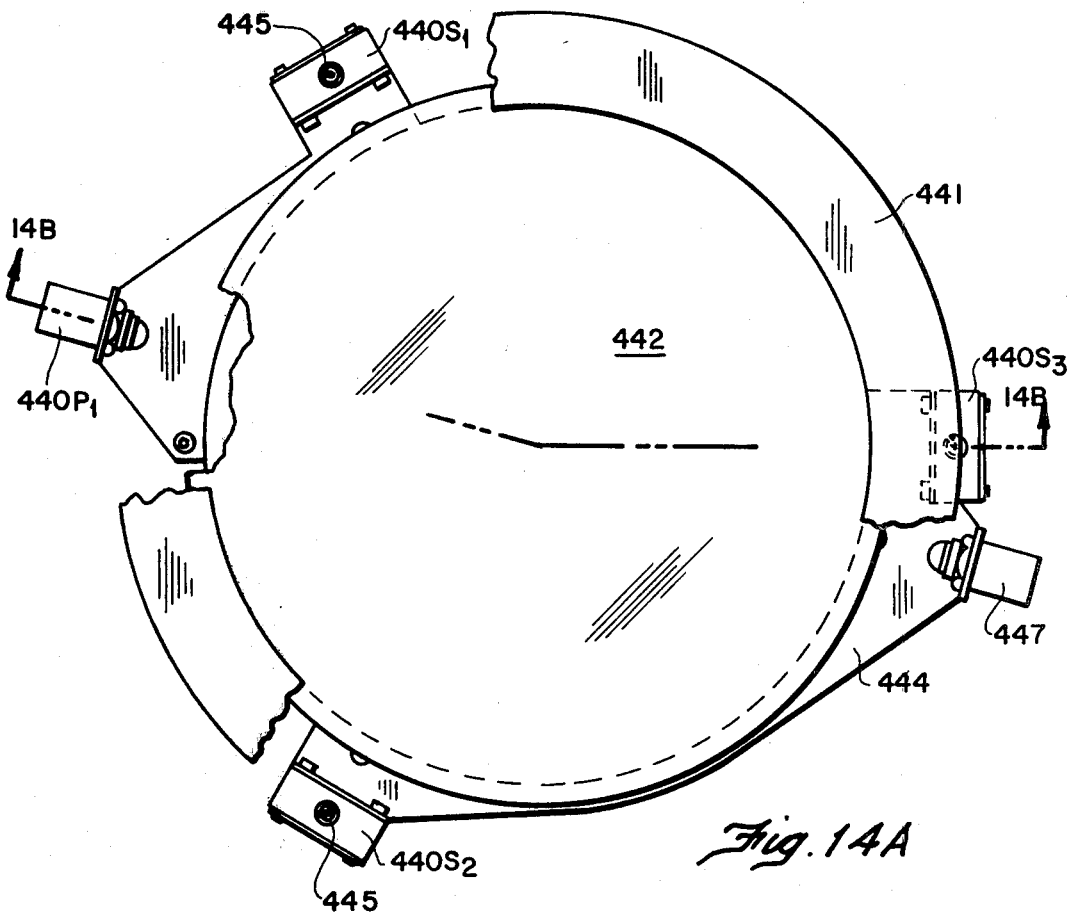
FIG. 14A is an elevational view on an enlarged scale of a sensor system for protecting the screen of the imaging unit, portions of the system being broken away to illustrate details.
Figure 14B:
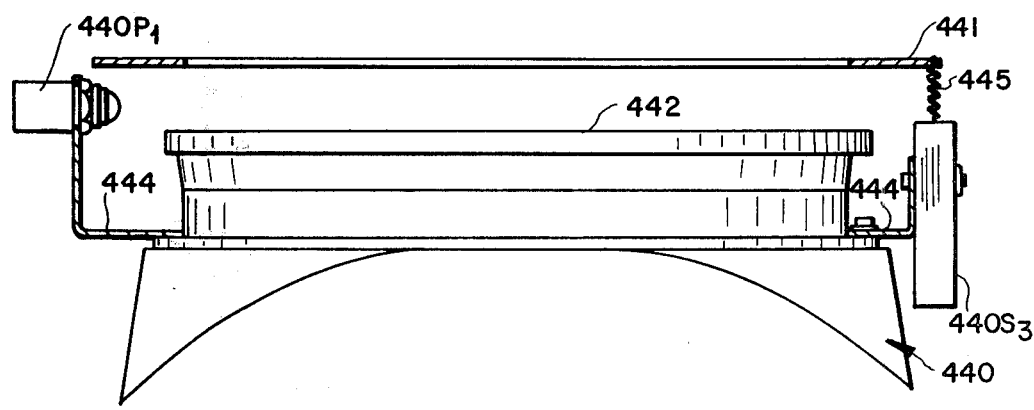
FIG. 14B is a cross-sectional view as seen from planes indicated by the broken line 14B—14B in FIG. 14A.

Referring to FIGS. 14A and 14B, a "halo" safety switch assembly is provided around the input screen of the imaging unit 440 to sense the presence of an object which could do damage to the imaging unit 440. The safety switch assembly includes a metal ring 441 movably supported at a position in front of the imaging screen 442. Three limit switches 440S1, 440S2, 440S3 are carried on a bracket 444 second to the imaging unit 440. The switches 440S1, 440S2, 440S3 have spring actuators 445 which are actuated if moved in any direction. The ring 441 is carried on the actuators 445. The limit switches 440S1, 440S2, 440S3 are electrically connected by a suitable cable (not shown) to the control console 1300 to illuminate certain malfunction indicator lights on the console if the ring 441 is moved by an object in close proximity to the imaging unit 440.

A photocell 440P1 is carried on the bracket 444. A light source 447 aimed at the photocell 440P1 is carried on the opposite side of the bracket 444 to provide a beam of light which extends across the screen 442. The photocell 440P1 is connected by a suitable cable (not shown) to the control console 1300 to operate in series with the switches 440S1, 440S2, 440S3 to illuminate certain malfunction indicator lights if the beam of light from the light source 447 to the photocell 440P1 is interrupted.

The Main Conveyor 450

Figure 15:
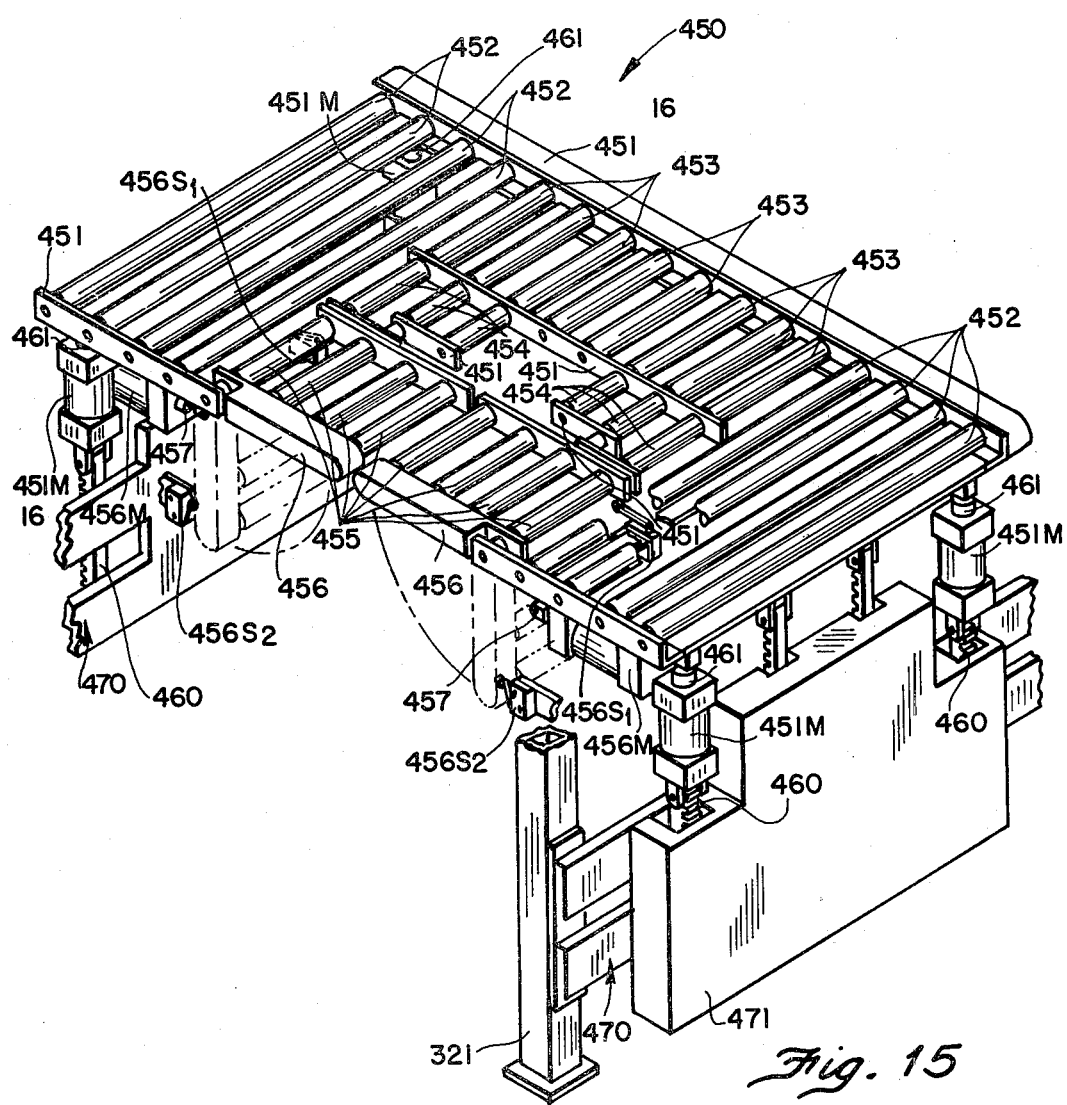
FIG. 15 is a perspective view of the main conveyor.
Figure 16:
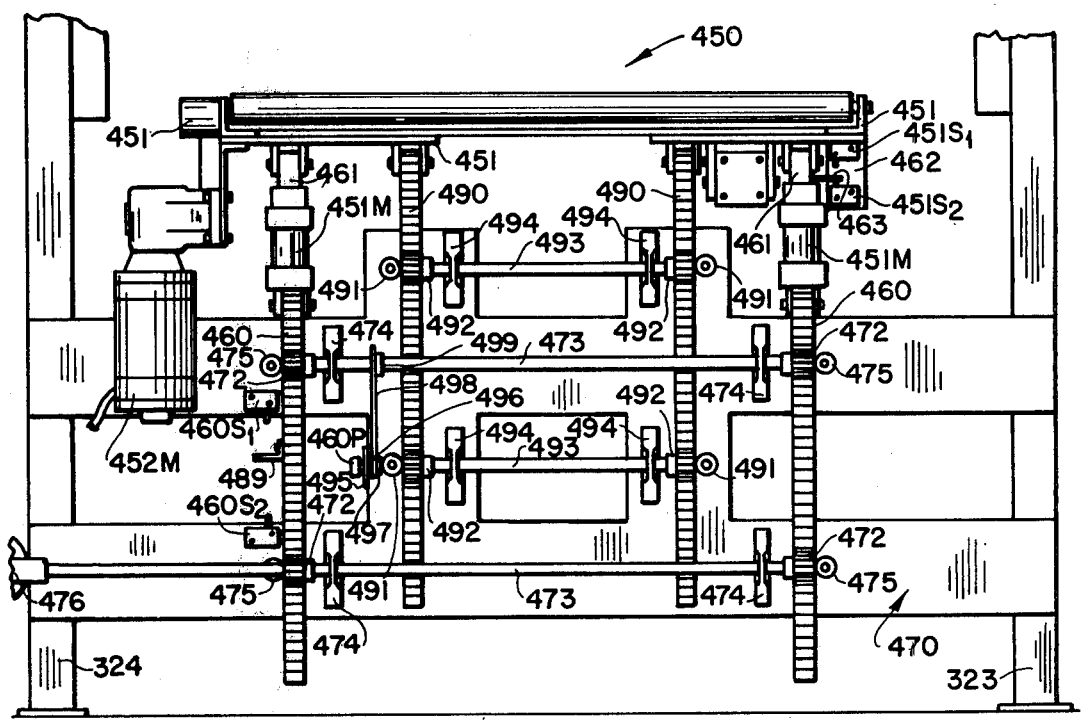
FIG. 16 is an end elevational view of portions of the main conveyor with the gear rack guard assembly removed.

Referring to FIGS. 15 and 16 in conjunction with FIGS. 1, 10 and 11, a main conveyor assembly 450 is carried by the main frame 320. The conveyor 450 includes a horizontally disposed frame 451 which rotatably supports a series of rolls 452, 453, 454, 455. A drive motor 452M carried beneath the frame 451 in the vicinity of the column 324 is drivingly connected to all the rolls 452, 453, 454, 455 to rotate the rolls and feed tires along the conveyor 450.

The rolls 452 extend the full width of the conveyor 450 and have opposite end regions journaled by the frame 451. The rolls 453, 454 are shorter than the rolls 452 and have opposite ends journaled by the frame 451. The rolls 455 are shorter than the rolls 452 and have ends journalled in two movable drop-down frame structures 456.

The frame structures 456 are pivotally mounted on the frame 451 for movement about the axis of the two farthest spaced rolls 455. The frame structures 456 are movable from an elevated position shown in solid lines in FIG. 15 to a lowered position shown in phantom in FIG. 15.

A pair of pneumatic motors 456M are provided for raising and lowering the movable frame structures 456. The motors 456M are pneumatic cylinders carried by the frame 451 and have extensible pistons 457 connected to the frame structures 456. When the pistons 457 are extended, the frame structures 456 assume their elevated position. When the pistons 457 are retracted, the frame structures 456 assume their lowered position.

Two pairs of limit switches 456S1, 456S2 are provided to sense when the conveyor frame structures 456 are elevated or lowered. The switches 456S1, 456S2 are supported on the frame 451, and have actuators which are selectively engaged by the frame structures 456 when the frame structures are elevated or lowered. The switches 456S1, 456S2 are each electrically connected by suitable conductors (not shown) to the control console 1300 to provide a step variation in a signal voltage.

The conveyor frame 451 together with the movable frame sections 456 are movably mounted on the main frame 320 for movement in vertical directions. Four pneumatic motors 451M are supported on gear racks 460. The motors 451M are pneumatic cylinders having extensible pistons 461 connected to corner regions of the rectangular frame 451. When the pistons 461 extend, the conveyor frame 451 is raised relative to the gear racks 460. When the pistons 461 retract, the conveyor frame 451 is lowered relative to the gear racks 460.

Referring to FIG. 16 a pair of limit switches 451S1, 415S2 are provided to sense when the main conveyor frame 451 is at the upper and lower ends of its range of travel. The switches 451S1, 451S2 are supported on a bracket 462 carried by the frame 451. An arm 463 is secured to one of the motor housings 451M and selectively engages one of the switches 451S1, 451S2 when the conveyor frame 451 is at the upper or lower ends of its range of travel relative to the gear racks 460. The switches 451S1, 451S2 are electrically connected by suitable conductors (not shown) to the control console 1300 to provide a step variation in a signal voltage indicating the position of the conveyor frame 451.

A pair of welded cross-member structures 470 have opposite end regions connected to the main frame columns 321, 322, 323, 324. A pair of shields 471 are secured to the cross-member structures 470 to shroud lower portions of the gear racks 460.

Referring to FIG. 16, one of the cross-member structures 470 is shown with the shield 471 removed. Each of the gear racks 460 is engaged by a pair of gears 472. The gears 472 are carried on opposite end regions of shafts 473. The shafts 473 are journaled by bearing blocks 474 carried on the cross-member structure 470. A plurality of rollers 475 carried on the cross-member structure 470 engage the gear racks 460 mounting the gear racks 460 for vertical movement relative to the main frame 320.

Referring to FIG. 11, one of the shafts 473 on each side of the main frame 320 is drivingly connected through right angle gear boxes 476 to a drive shaft 477. A drive motor assembly 460M is provided for rotating the shafts 473, 477. The drive motor 460M has an output shaft 480 which carries a sprocket 481. A drive chain 482 is reeved around the sprocket 481 and around a sprocket 483 carried on the drive shaft 477. When the drive motor 460M rotates the shafts 473 in one direction, the gear racks 460 are elevated relative to the main frame 320. When the drive motor 460M rotates the shafts 473 in the opposite direction, the gear racks 460 are lowered relative to the main frame 320.

Referring to FIG. 16, four auxiliary gear racks 490 have their upper end regions connected to the conveyor frame 451. A plurality of rollers 491 carried on the cross-member assemblies 470 engage the auxiliary gear racks 490 and mount them for vertical movement relative to the cross members 470. Each of the auxiliary gear racks 490 is engaged by a pair of gears 492. The gears 492 are carried on opposite end regions of shafts 493. The shafts 493 are journaled by bearing blocks 494 carried on the cross-member structures 470. The auxiliary gear racks 490 serve to keep the conveyor frame 451 level when it moves up and down relative to the gear racks 460 under the influence of the pneumatic cylinders 451M.

The vertical position of the gear racks 460 is monitored by a potentiometer 460P. The potentiometer 460P is carried by a bracket 495 secured to one of the cross-members 470, as best seen in FIG. 16. The potentiometer 460P has a rotatable stem 496 which carries a sprocket 497. A roller chain 498 is reeved around the sprocket 497 and around a sprocket 499 on one of the shafts 473. Rotation of the shafts 473 by the motor 460M effects concurrent rotation of the potentiometer stem 496. A suitable electrical cable (not shown) connects the potentiometer 460P with the control console 1300. The potentiometer 460P provides a resistance which varies to provide a variation in a signal voltage indicating the height of the gear racks 460.

A pair of limit switches 460S1, 460S2 are provided to sense when the gear racks 460 are at the upper or lower ends of their range of travel. The switches 460S1, 460S2 are supported on one of the cross-member structures 470 as best seen in FIG. 16. An arm 489 carried on one of the gear racks 460 selectively engages one of the switches 460S1, 460S2 when the gear racks 460 are at their upper or lower ends of their range of travel. The switches 460S1, 460S2 are electrically connected by suitable conductors (not shown) to the control console 1300 to provide a step variation in a signal voltage.

As will be explained in greater detail, the main conveyor 450 is initially pre-positioned such that the rolls 452-455 are at a height commensurate with the rolls 142 on the left end of the centering table conveyor 140. At the time the conveyor 450 is pre-positioned, the pistons 461 are extended from the pneumatic motors 451M. Once a tire has been positioned for inspection on the conveyor 450, the pistons 461 are retracted to the lower rolls of the conveyor 450 a short distance, typically about 1½ inches, permitting the tire to be supported on spindles for rotation.

The Spindle Carriages 510

Figure 17:
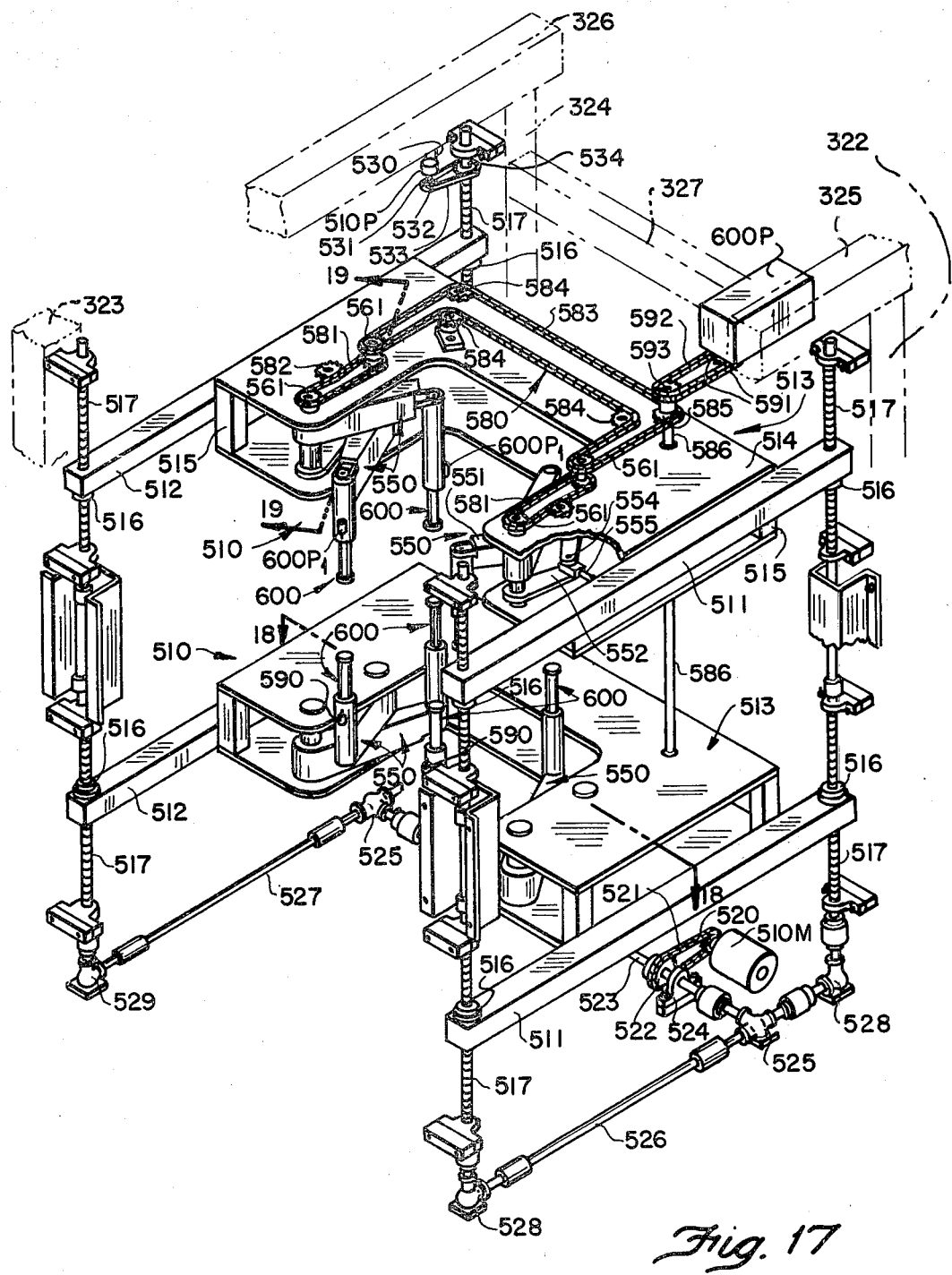
FIG. 17 is a perspective view of the spindle carriages and their respective drive systems.

Referring to FIGS. 10 and 17, a pair of spindle carriages 510 are movably carried by the main frame 320. One of the spindle carriages 510 is positioned above the main conveyor 450, and will be called the upper spindle carriage. The other carriage 510 underlies the rollers of the main conveyor 450 and will be called the lower spindle carriage. The upper and lower carriages 510 are substantially identical, one being the mirror image of the other.

Each of the carriages 510 includes a pair of support beams 511, 512. The beams 511 extend between the main frame columns 321, 322. The beams 512 extend between the main frame columns 323, 324. The beams 511, 512 support a pair of welded frame structures 513. The frame structures 513 each include a pair of spaced, horizontal plates 514 interconnected by uprights 515.

The carriages 510 are supported for concurrent vertical movement toward and away from each other. Threaded bushings 516 are carried near opposite ends of the beams 511, 512. Threaded rods 517 are received in the bushings. The upper carriage bushings 516 are threaded with L. H. threads to accommodate L. H. threads formed on the upper end regions of the rods 517. The lower carriage bushings 516 are threaded with R. H. threads to accommodate R. H. threads formed on the lower end regions of the rods 517. When the rods 517 are rotated concurrently in one direction, the carriages 510 move toward each other. When the rods 517 are rotated concurrently in the opposite drive direction, the carriages 510 move away from each other.

A reversible carriage drive motor 510M is carried by the main frame 320. The motor 510M has an output shaft which carries a sprocket 520. A roller chain 521 is reeved around the sprocket 520 and around a sprocket 522 carried on a shaft 523. The shaft 523 is journaled by bearing blocks 524 secured to the main frame 320. A pair of right angle gear boxes 525 drivingly connect opposite ends of the shaft 523 to a pair of transversely extending shafts 526, 527. Two pairs of right angle gear boxes 528, 529 drivingly connect opposite ends of the shafts 526, 527 to the threaded support rods 517.

The vertical position of the spindle carriages 510 is monitored by a potentiometer 510P. Referring to FIG. 17, the potentiometer 510P is carried by a bracket 530 secured to the main frame beam 326. The potentiometer 510P has a rotatable stem 531 which carries a sprocket 532. A roller chain 533 is reeved around the sprocket 532 and around a drive sprocket 534 carried on one of the rods 517. Rotation of the rods 517 by the motor 510M effects concurrent rotation of the potentiometer stem 531. A suitable electrical cable (not shown) connects the potentiometer 510P with the control console 1300. The potentiometer 510P provides a resistance which varies to provide a variation in a signal voltage indicating the position of spindle carriages 510 along the rods 517.

The Spindle Support Arms 550

Four spindle support arms 550 are pivotally mounted on each of the spindle carriages 550. As is best seen in FIG. 18, the arms 550 each have a long leg 551 and a short leg 552. Each of the arms 550 is pivotally mounted on a separate shaft 553. The shafts 553 are journaled by bearings carried in the plates 514, as will be explained.

The arms 550 are arranged in pairs with the long legs 551 of each pair criss-crossed, and with the short legs 552 connected together by a pin 554. A separate link 555 connects with each of the pins 554.

A pneumatic motor 550M is provided on each of the carriages 510 for pivoting the arms 550 about the shafts 553. Each of the motors 550M is a pneumatic cylinder having an extensible piston 556. A pair of L-shaped actuating levers 557 are mounted for pivotal movement on each of the carriages 510. Vertically extending pins 558 journaled in the plates 514 carry the levers 557. One end region of each of the levers 557 connects with one of the pistons 556. The other end region of the levers 557 is connected to one of the links 555.

Each of the long legs 551 of the arms 550 carries a separate spindle 600. The spindles 600 move with the arms 550 between the fully retracted position shown in FIG. 18 and the fully extended position shown in FIG. 17. When the pistons 556 of the motors 550M are fully extended, the spindles 600 assume their fully extended position. When the pistons 556 of the motors 550M are fully retracted, the spindles 600 assume their fully retracted position.

The pressure of the compressed air supplied to the motors 550M is regulated to control the amount of force applied by the spindles to a tire being inspected. A conventional pressure regulator shown at 559 in FIG. 18, is used to vary the pressure supplied to the motors 550M. The regulator 559 is electrically controlled through a suitable cable (not shown) which connects with the control console 1300. The regulator 559 is preferably operable to adjust the pressure supplied to the motors 550M from a low pressure of about 18 psi to a high pressure of about 60 psi. A lesser spindle extension pressure is used with relatively small tires than is used with relatively large tires.

The position of the spindle arms 550 is monitored by a potentiometer 550P. The potentiometer 550P is carried by a bracket 558a secured to one of the plates 514. The potentiometer 550P has a rotatable stem which carries a sprocket 559b. A roller chain 559c is reeved around the sprocket 559b and around a drive sprocket 559d secured to one of the spindle arms 550. Rotation of the spindle arms 550 by the motor 550M effects concurrent rotation of the stem of the potentiometer 550P. A suitable electrical cable (not shown) connects the potentiometer 550P with the control console 1300. The potentiometer 550P provides a resistance which varies to provide a variation in a signal voltage indicating the position of spindle arms 550.

A pair of limit switches 550S$_1$, 550S$_2$ are provided on each of the carriages 510 to sense when the spindles 600 are at the fully retracted or extended ends of their range of travel. The switches 550S$_1$, 550S$_2$ are supported on one of the plates 514. One of the levers 557 selectively engages one of the switches 550S$_1$, 550S$_2$ when the spindles are fully retracted or extended. The switches 550S$_1$, 550S$_2$ are electrically connected by suitable conductors (not shown) to the control console 1300 to provide a step variation in a signal voltage.

Referring to FIG. 19, a typical one of the spindle arms 550 is shown in cross-section. A pair of bearings 560 carried by the plates 514 journal the shaft 553. A pair of sprockets 561 are secured by pins 562 to the upper end region of the shaft 553. A double toothed drive sprocket 563 is secured by a pin 564 to an intermediate portion of the shaft 553.

The arm 550 includes two aligned bushings 565, 566 carried on the shafts 553 on opposite sides of the double drive gear 563. A pair of bearings 567 journal the upper bushings 565 on the shaft 563. A bearing 568 journals the lower bushing 566 on the shaft 563. The short leg 552 of the arm 550 is welded to the upper bushing 565. The long leg 551 of the arm 550 is a tubular structure welded to both of the bushings 565, 566.

A spindle support sleeve 570 is welded to the outer end region of the long leg 551. A pair of bearings 571 carried in the sleeve 570 journal a spindle shaft 572 for rotation. The upper end of the spindle shaft 572 carries a double toothed drive sprocket 573. A double roller chain 574 is reeved around the sprockets 563, 573 to rotate the spindle shaft 572 in response to rotation of the shaft 553.

A tubular spindle member 575 is secured by a pin 576 to the lower end region of the spindle shaft 572. The spindle member 575 has an annular lip 577 formed near its lower end to receive the bead of a tire during inspection.

Referring to FIG. 17, a chain drive system indicated generally by the numeral 580 is provided for rotating the spindles 600. The drive system 580 includes a pair of roller chains 581 on each of the carriages 510 which are reeved around and drivingly connect pairs of the spindles drive sprockets 561. Idler sprockets 582 carried on one of the plates 514 tension the chain 581. Another roller chain 583 carried on each of the carriages 510 and is reeved around the remaining two spindle drive sprockets 561 and around a series of idler sprockets 584, and around a drive sprocket 585. The drive sprocket 585 is carried on a splined shaft 586 which is journaled by bearing blocks on the main frame 320. As the spindle carriages 510 move upwardly and downwardly relative to the main frame, the drive sprockets 585 move along the splined drive shaft 586.

Referring to FIG. 10, a spindle drive motor 600M is supported on the main frame 320. The spindle drive motor 600M drivingly connects with the splined drive shaft 586 to rotate the shaft 586 and thereby drive the spindles 600.

The rotation of the spindles 600 is monitored by a tachometer 600P, carried atop the cross-member 327 as shown in FIG. 17. The tachometer 600P has a drive shaft which carries a sprocket 591. A roller chain 592 is reeved around the sprocket 591 and around a sprocker 593 carried on the drive shaft 586. The tachometer 600P provides an output signal which is representative of the velocity of rotation of the drive shaft 586. A suitable electrical cable (not shown) connects the tachometer 600P with the control console 1300.

The upper spindles 600 each carry a photocell 600P1. The lower spindles 600 each carry a light source 590. The photocells 600P1 are connected by suitable electrical conductors (not shown) to the control console 1300 to provide a step variation in a signal voltage. The photocells 600P1 serve in one capacity to assure that a tire is centered for spindle insertion. Once the spindles 600 have engaged a tire for inspection, the light beams from the sources 590 should be blocked by the tire from being received by the photocells 600P1.

The X-ray Carriage

Figure 20:
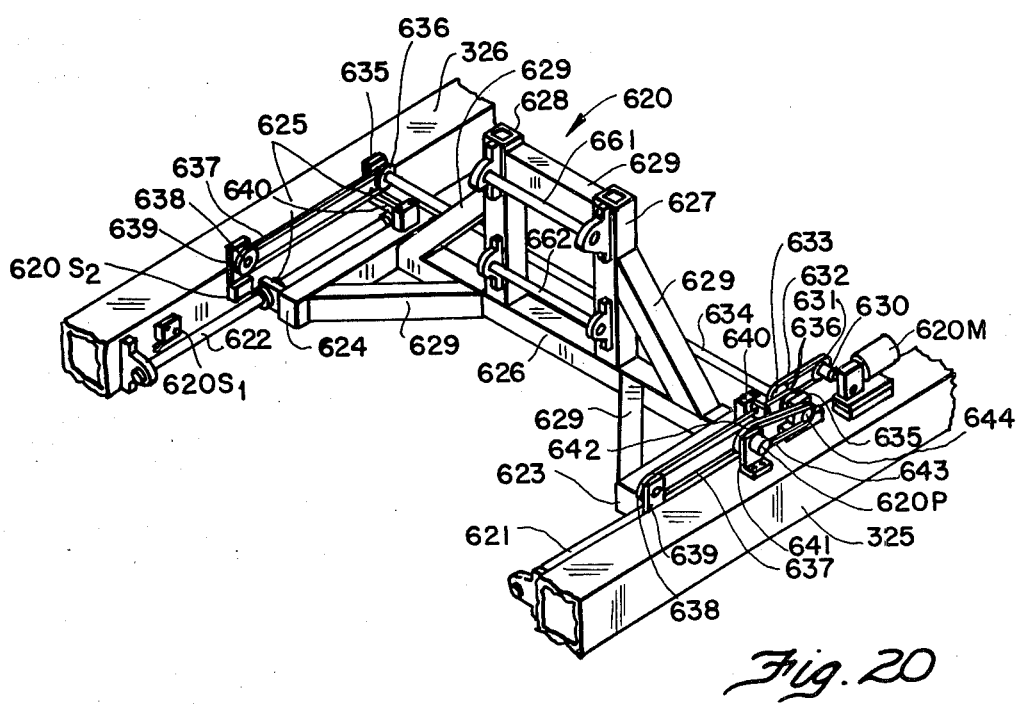
FIG. 20 is an enlarged perspective view of the X-ray carriage.

Referring to FIG. 20, an X-ray carriage 620 is movably carried by the main frame beams 325, 326. A pair of guide rods 621, 622 are carried by the beams 325, 326. The carriage 620 has a pair of side members 623, 624 which extend alongside the guide rods 621, 622. Bearing blocks 625 carried by the side members 623, 624 slidably receive the guide rods 621, 622 to movably mount the X-ray carriage 620 on the main frames beams 325, 326.

The X-ray carriage 620 includes a cross-member 626 which extends between the side members 623, 624 a pair of upstanding members 627, 628 are secured to the cross-member 626. A short cross-member 629 extends between the upstanding members 627, 628. Four brace members 629 are welded to the members 623, 624, 626, 627, 628 to form a rigid frame structure.

A drive motor 620M is carried by the main frame beam 325 for moving the carriage 620 along the guide rods 621, 622. The drive motor 620 has an output shaft 630 which carries a sprocket 631. A roller chain 632 is reeved around the sprocket 631 and around a sprocket 633. The sprocket 633 is carried on a shaft 634. A pair of bearing blocks 635 carried on the main frame beams 325, 326 journal the shaft 634. A pair of sprockets 636 are carried on the shaft 634 near opposite end regions. A pair of roller chains 637 are reeved around the sprockets 636 and around a pair of idler sprockets 638. The idler sprockets 638 are mounted on brackets 639 secured to the main frame beams 325, 326.

A pair of brackets 640 secured to the side members 623, 624 of the X-ray carriage 620 connect with the roller chains 637. When the drive motor 620M rotates the shaft 634 in one direction, the carriage 620 moves inwardly along the guide rods 621, 622. When the drive motor 620M rotates the shaft 634 in the opposite direction, the carriage 620 moves outwardly along the guide rods 621, 622.

The position of the X-ray carriage 620 along the guide rods 621, 622 is monitored by a potentiometer 620P. The potentiometer 620P is carried on a bracket 641 secured to the beam 325. The potentiometer 620P has a stem which carries a sprocket 642. A roller chain 643 is reeved around the sprocket 642 and around a sprocket 644 carried on the drive shaft 634. Rotation of the drive shaft 634 by the motor 620M effects concurrent rotation of the stem of the potentiometer 620P. A suitable electrical cable (not shown) connects the potentiometer 620P with the control console 1300. The potentiometer 620P provides a resistance which varies to provide a variation in a signal voltage indicating the position of the carriage 620 along the guide rods 621, 622.

A pair of limit switches $620S_1$, $620S_2$ are carried on the main frame beam 326 to sense when the carriage 620 is at the inward and outward ends of its range of travel. The switches $620S_1$, $620S_2$ are selectively engaged by one of the bearing blocks 625 when the carriage 620 is in its fully inward or outward position. The switches $620S_1$, $620S_2$ are electrically connected by suitable conductors (not shown) to the control console 1300 to provide a step variation in a signal voltage.

The X-ray Sub-carriage 600

Figure 21:
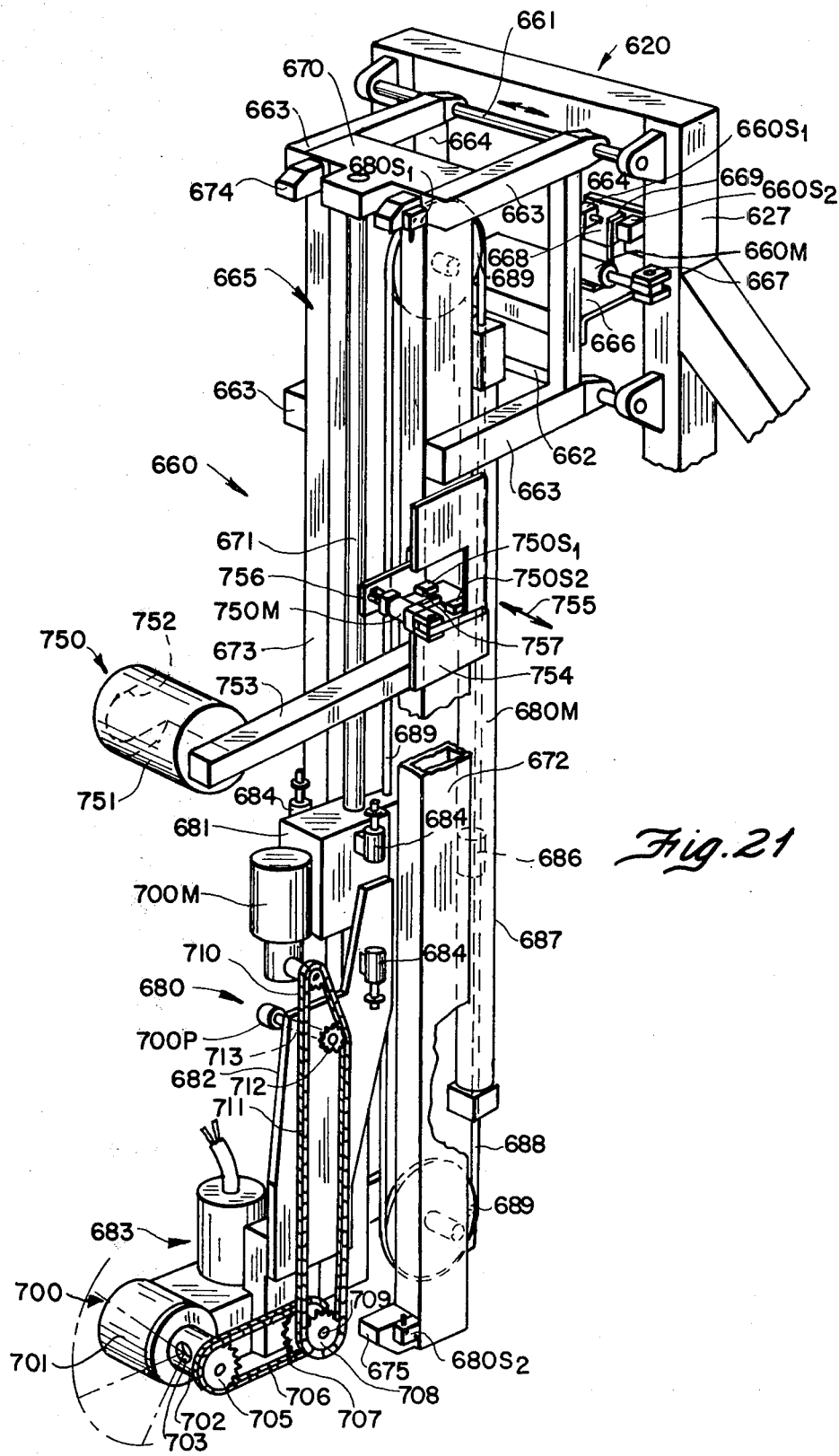
FIG. 21 is an enlarged perspective view of the X-ray sub-carriage and X-ray sub-sub-carriage together with the X-ray tube assembly.

Referring to FIG. 21, an X-ray sub-carriage 660 is supported on the X-ray carriage 620. A pair of guide rods 661, 662 are carried by the upright members 627, 628 of the X-ray carriage 620. The X-ray sub-carriage 660 includes four horizontally extending members 663 interconnected by a pair of upright members 664. The horizontal members 663 are apertured near one end to slidably receive the guide rods 661, 662. The other end regions of the horizontal members 663 are secured to a depending mast assembly 665.

A pneumatic motor 660M is provided for moving the X-ray sub-carriage 660 along the guide rods 661, 662.

The motor 660M is secured to a bracket 666 carried on the upright members 664. The motor 660M is a pneumatic cylinder having an extensible piston 667 secured to the X-ray carriage upright member 627. Extension and retraction of the piston 667 is operative to move the X-ray sub-carriage 620 along the guide rods 661, 662.

The movement of the X-ray sub-carriage 660 along the guide rods 661, 662 is referred to as the X-ray sub-carriage offset movement. As will be explained in greater detail, the offset movement is used in conjunction with the inspection of small tires having a relatively small inner diameter which requires that the oblong X-ray tube assembly 700 be moved off center in order to be admitted to the tire torus.

A pair of limit switches $660S_1$, $660S_2$ is provided to sense when the X-ray sub-carriage 660 is at opposite ends of its range of travel along the guide rods 661, 662. The switches $660S_1$, $660S_2$ are supported on a bracket 668 secured to the X-ray carriage upright member 627. An arm 669 secured to the bracket 666 selectively engages one of the switches $660S_1$, $660S_2$ when the X-ray sub-carriage 660 is at opposite ends of its range of travel. The switches $660S_1$, $660S_2$ are electrically connected by suitable conductors (not shown) to the control console 1300 to provide a step variation in a signal voltage.

The mast assembly 665 includes an upper plate 670 secured between two of the horizontally extending members 663. A guide rod 671 depends from the plate 670 in parallel spaced relationship with a pair of column members 672, 673. A pair of stops 674 are carried on the top plate 670. A pair of stops 675 are carried near the lower ends of the column member 672, 673.

The X-ray Sub-Sub-Carriage

Referring to FIG. 21, and X-ray sub-sub-carriage 680 is movably mounted on the X-ray sub-carriage 660. The sub-sub-carriage 680 includes a mounting block 681 which is apertured to slidably receive the guide rod 671. A bracket 682 depends from the mounting blocks 681 and carries an X-ray tube housing assembly 700. Four shock absorber units 684 are carried on the X-ray sub-sub-carriage 680 to engage the stops 674, 675 when the X-ray sub-sub-carriage 681 is at opposite ends of its travel along the guide rods 671.

A pneumatic motor 680M is provided on the mast 655 to move the X-ray sub-sub-carriage 680 up and down along the guide rods 671. The motor 680M is a pneumatic cylinder having a piston 686 movable along the length of a tubular housing 687. A cable 688 has opposite ends connected to the piston 686. A pair of pulleys 689 are rotatably carried at opposite ends of the motor 680M. The cable 688 is reeved around the pulleys 689. The cable 688 connects with the block 681 to drivingly connect the X-ray sub-sub-carriage 680 wwith the motor 680M. When the piston 686 is driven downwardly by compressed air supplied to the motor 680M, the X-ray sub-sub-carriage 680 travels to its up or retracted position where the upper shock absorbers 684 engage the stops 674. When the piston 686 is driven upwardly by compressed air supplied to the motor 686, the x-ray sub-sub-carriage 680 descends to its extended position where the lower shock absorbers 684 engage the stops 675.

A pair of limit switches $680S1$, $680S2$ are provided to sense when the X-ray sub-sub-carriage 680 is at the upper and lower ends of its range of travel. The switches $680S1$, $680S2$ are supported on the stops 674, 675, and are selectively engaged by one of the shock absorbers 684 when the X-ray sub-sub-carriage 680 is at the upper or lower ends of its range of travel. The switches 680S1, 680S2 are electrically connected by suitable conductors (not shown) to the control console 1300 to provide a step variation in a DC signal voltage.

The X-ray Tube Assembly 700

The X-ray tube assembly 700 is of the type described in the referenced Tire Inspector Patent. In brief, the tube assembly has a housing 701 and an X-ray tube (not shown) which is rotatably carried in the housing 701. The housing 701 is apertured at 703 to emit X-radiation. The housing 701 and the tube are rotatable to direct a beam of emitted X-radiation upwardly and downwardly through an arc of about 80 degrees above and below a zero degree or horizontal orientation.

A sprocket 705 is connected to the sleeve 701. A drive chain 706 is reeved around the sprocket 705 and around a sprocket 707. The sprocket 707 and an additional sprocket 708 are carried on a stub shaft 709. The stub shaft 709 is carried by the bracket 682.

A reversible drive motor 700M is provided to rotate the housing 701. The motor 700M has an output shaft which carries a sprocket 710. A drive chain 711 is reeved around the sprockets 708 and 710, and around an idler sprocket 712. When the motor 700M rotates the sprocket 710 in one direction, the housing 701 and the X-ray tube rotate upwardly. When the motor 700M rotates the sprocket 710 in the opposite drive direction, the housing 701 and the X-ray tube rotate downwardly.

The orientation of the housing 701 and the X-ray tube is monitored by a potentiometer 700P. The potentiometer 700P is carried on the bracket 682 and has a rotatable stem 713 which carries the sprocket 712. Rotation of the sprocket 712 by the motor 700M effects concurrent rotation of the potentiometer stem 713. A suitable electrical cable (not shown) connects the potentiometer 700P with the control console 1300. The potentiometer 700P provides a resistance which varies to provide a variation in a signal voltage indicating the direction of X-ray beam emission from the X-ray tube assembly 700.

The X-ray Tube Shield 750

Referring to FIG. 21, an X-ray tube shield 750 is carried on the X-ray sub-carriage 660. The shield 750 includes a cylindrical lead-lined steel member 751 provided with a U-shaped recess 752 to receive the X-ray housing 701. An arm 753 secured to a bracket 754 supports the member 751. The bracket 754 is supported for movement relative to the column member 672 in directions indicated by the arrow 755. A pair of guide rods (not shown) are carried on the column member 672. The bracket 754 journals these guide rods to movably mount the shield 750 on the X-ray sub-carriage 660.

A pneumatic motor 750M is provided for moving the X-ray shield 750 in the directions of the arrow 755. The motor 750M is an extensible pneumatic cylinder having one end connected to the bracket 754. The other end of the cylinder 750M is connected to a bracket 756 secured to the column member 672. When the cylinder 750M extends, the shield 750M is moved rightwardly as viewed in FIG. 21 to uncover the X-ray beam emission aperture 703 and permit the X-ray sub-sub-carriage 680 to descend to the extended position shown in FIG. 21. When the cylinder 750M retracts with the X-ray sub-sub-carriage 680 in its up or retracted position, the shield 750 moves leftwardly to cover the X-ray emission aperture 703.

A pair of limit switches 750S$_1$, 750S$_2$ are provided to sense when the X-ray shield 750 is at the opposite ends of its range of travel. The switches 750S$_1$, 750S$_2$ are supported on the bracket 756 secured to the column member 672. An arm 757 secured to the housing of the cylinder 750M selectively engages one of the switches 750S$_1$, 750S$_2$ when the X-ray shield 750 is at the left or right ends of its range of travel. The switches 750S$_1$, 750S$_2$ are electrically connected by suitable conductors (not shown) to the control console 1300 to provide a step variation in a signal voltage.

The Traveling Positioning Switch 820

Referring to FIG. 22 in connection with FIG. 1, a traveling positioning switch assembly 820 is carried on the main frame 320 at a position leftwardly of the X-ray sub-carriage 660. The main frame assembly 320 has a bracket 328 which depends from the beam 326. A channel member 821 is welded to the bottom end of the bracket 328. A pair of guide rods 822 are carried on the channel 821 along the forward side of the channel 821. A mounting block 823 is apertured to slidably receive the rods 822 for sliding movement along the rods 822.

A drive motor 820M is carried on the channel 821 for moving the block 823 along the guide rods 822. The motor 820M carries a drive sprocket (not shown) which drives a roller chain 824. The roller chain 824 is reeved around a sprocket 825 carried near one end of the channel 821. A bracket 826 secures the block 823 to the roller chain 824. When the motor 820M rotates the roller chain 824 in one direction, the block 823 moves rightwardly along the guide rods 822. When the motor 820M rotates the chain 824 in the opposite direction, the block 823 moves leftwardly along the guide rods 822.

The position of the block 823 along the guide rods 822 is monitored by a potentiometer 820P. The potentiometer 820P is carried on a bracket 828 secured to the channel 821. The potentiometer 820P has a stem 829 which is secured to the sprocket 825. Rotation of the sprocket 825 by the motor 820M effects concurrent rotation of the potentiometer stem 829. A suitable electrical cable (not shown) connects the potentiometer 820P with the console 1300. The potentiometer 820P provides a resistance which varies to provide a variation in a signal voltage indicating the position of the block 823 along the guide rods 822.

A pair of limit switches 820S$_1$, 820S$_2$ are carried near opposite ends of the channel 821. An arm 827 secured to the block 823 selectively engages one of the limit switches 820S$_1$, 820S$_2$ when the block 823 is at opposite ends of its range of travel along the guide rods 822. The switches 820S$_1$, 820S$_2$ are electrically connected by suitable conductors (not shown) to the control console 1300 to provide a step variation in a signal voltage.

A shaft 830 is journaled by the block 823. Three depending arms 831, 832, 833 have their upper end regions connected to the shaft 830. A long roller 834 extends between the arms 831, 832. A plurality of shorter rollers 835 extend between the arms 832, 833. A pair of counterweights 836 connect with the shaft 830 to bias the arms 831, 832, 833 rightwardly to the position shown in solid lines in FIG. 22.

A pair of limit switches 452S$_1$, 452S$_2$ are carried on the block 823. A pair of cams 837, 838 are secured to the shaft 830 for actuating the limit switches 452S$_1$, 452S$_2$. The limit switch 452S$_1$ is a "slow-down switch". When a tire moving along the main conveyor rolls 452 engages the roller 834 and pivots the arms 831, 832, 833 leftwardly as viewed in FIG. 22, the cam 837 actuates the plunger of the slow-down switch 452S$_1$, to slow the speed at which the main conveyor 450 is being driven by the motor 452M. The limit switch 452S$_2$ is a "stop switch". When the arms 831, 832, 833 are pivoted leftwardly to a greater extent than is required to trip the switch 452S1, the cam 838 actuates the plunger of the limit switch 452S2 to stop the driving action of the main conveyor motor 452M.

As will be explained, the position of the block 823 along the guide rods 822 is pre-set in accordance with the size of a tire to be inspected. By pre-setting the block 823 along the guide rods 822, the limit switch rollers 834, 835 are positioned to slow down and stop the conveyor 450 and thereby position a tire to be inspected directly beneath the X-ray tube sub-carriage 660. After a tire wire has been inspected, the conveyor 450 moves the tire leftwardly, pivoting the arms 831, 832, 833 leftwardly out of the way of the tire as it is discharged from the shielded enclosure 275.

The Inputs to and the Outputs from the Control Console 1300

Figure 23B:
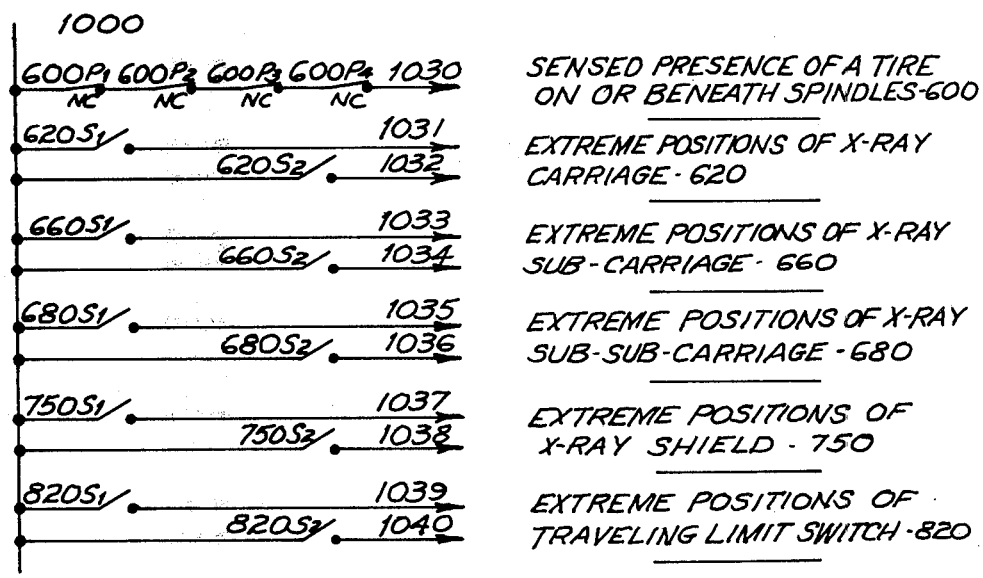

Referring to FIGS. 23A, 23B the outputs from the several described photocells and limit switches are shown schematically as forming inputs to the control console 1300. Each of the inputs is shown as selectively forming a connection with a line conductor 1000. There are a total of 40 of these inputs, numbered 1001–1040.

The output signal from the photocell 101P1 forms the input 1001. The outputs from the limit switches 140S1, 140S2 form the inputs 1002, 1003. The outputs from the photocells 142P1, 142P2 connected in parallel forms the input 1004.

The outputs from the limit switches 160S1, 160S2 form the inputs 1005, 1006. The outputs from the photocells 161P1, 161P2 connected in parallel forms the input 1007. The outputs from the limit switches 190S1, 190S2 connected in series forms the input 1008.

The output signal from the limit switch 195S1 forms the input 1009. The output from the normally closed contacts of the photocells 278P1, 278P2 connected in series forms the input 1010. The output from the normally closed contacts of the limit switches 278S1 connected in series forms the input 1011. The output from the normally closed contacts of the limit switches 278S2 connected in series forms the input 1012.

The outputs from the switches 340S1, 340S2, 390S1, 390S2, 420S1, 420S2 form the inputs 1013, 1014, 1015, 1016, 1017, 1018. The output from the normally closed contacts of the switches 440S1, 440S2, 440S3 connected in series with the normally closed contacts of the photocell 440P1 forms the input 1019.

The outputs from the switches 451S1, 451S2, 452S1, 452S2, 456S1, 456S2, 460S1, 460S2, 550S1, 550S2 form the inputs 1020, 1021, 1022, 1023, 1024, 1025, 1026, 1027, 1028, 1029. The outputs from the normally closed contacts of the photocells 600P1, 600P2, 600P3, 600P4 connected in series forms the input 1030.

The outputs from the switches 620S1, 620S2, 660S1, 660S2, 680S1, 680S2, 750S1, 750S2, 820S1, 820S2 form the inputs 1031, 1032, 1033, 1034, 1035, 1036, 1037, 1038, 1039, 1040.

Figure 24:
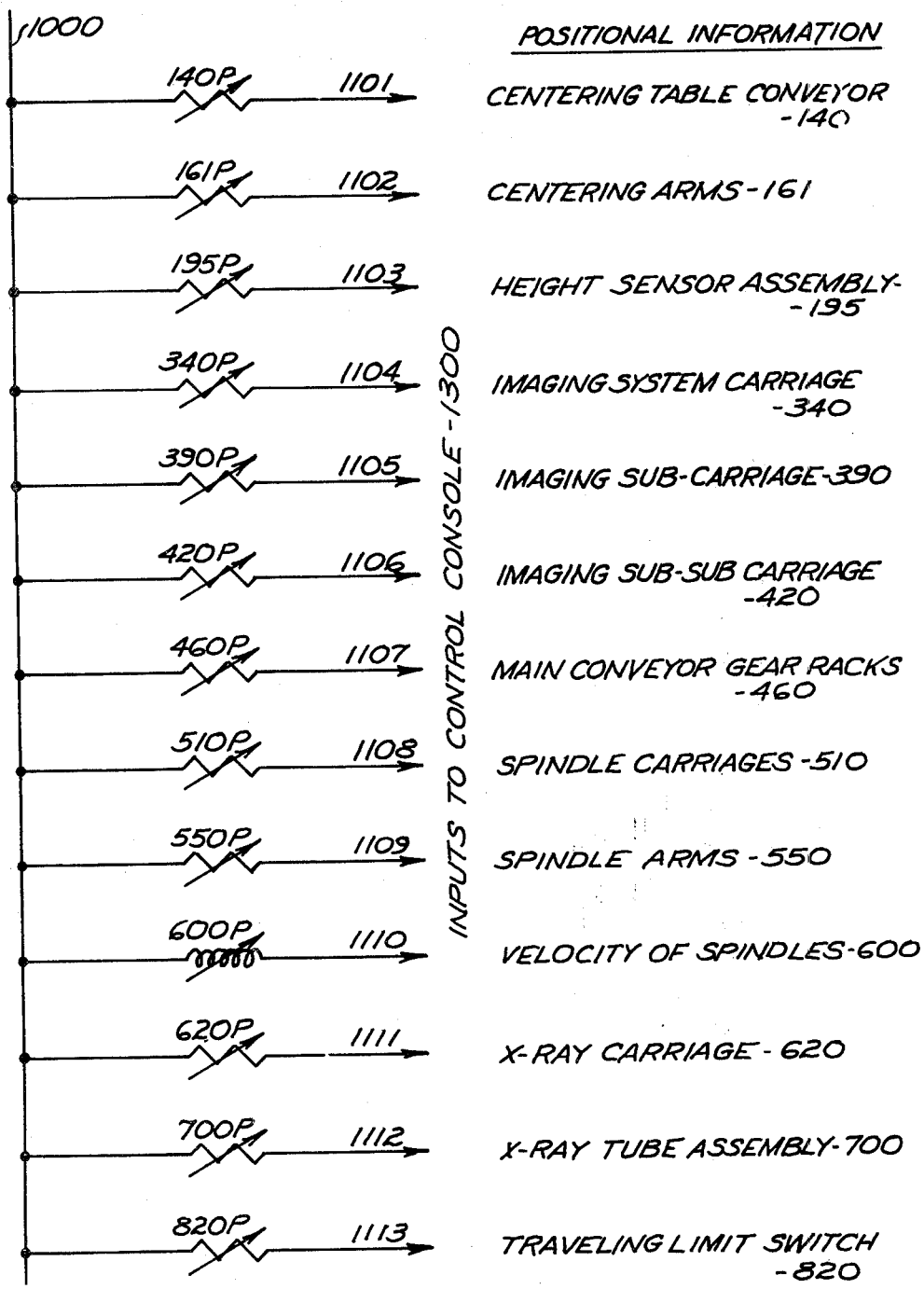
FIG. 24 is a schematic electrical diagram tabulating the several inputs to the control console from potentiometers and a tachometer.

Referring to FIG. 24, the outputs from the several described potentiometers and tachometer are shown schematically as forming inputs to the control sonsole 1300. Each of the potentiometers and tachometer is shown as selectively forming a variable resistance connection with the line conductor 1000. There are a total of 13 of these inputs, numbered 1101–1113.

Figure 25A:
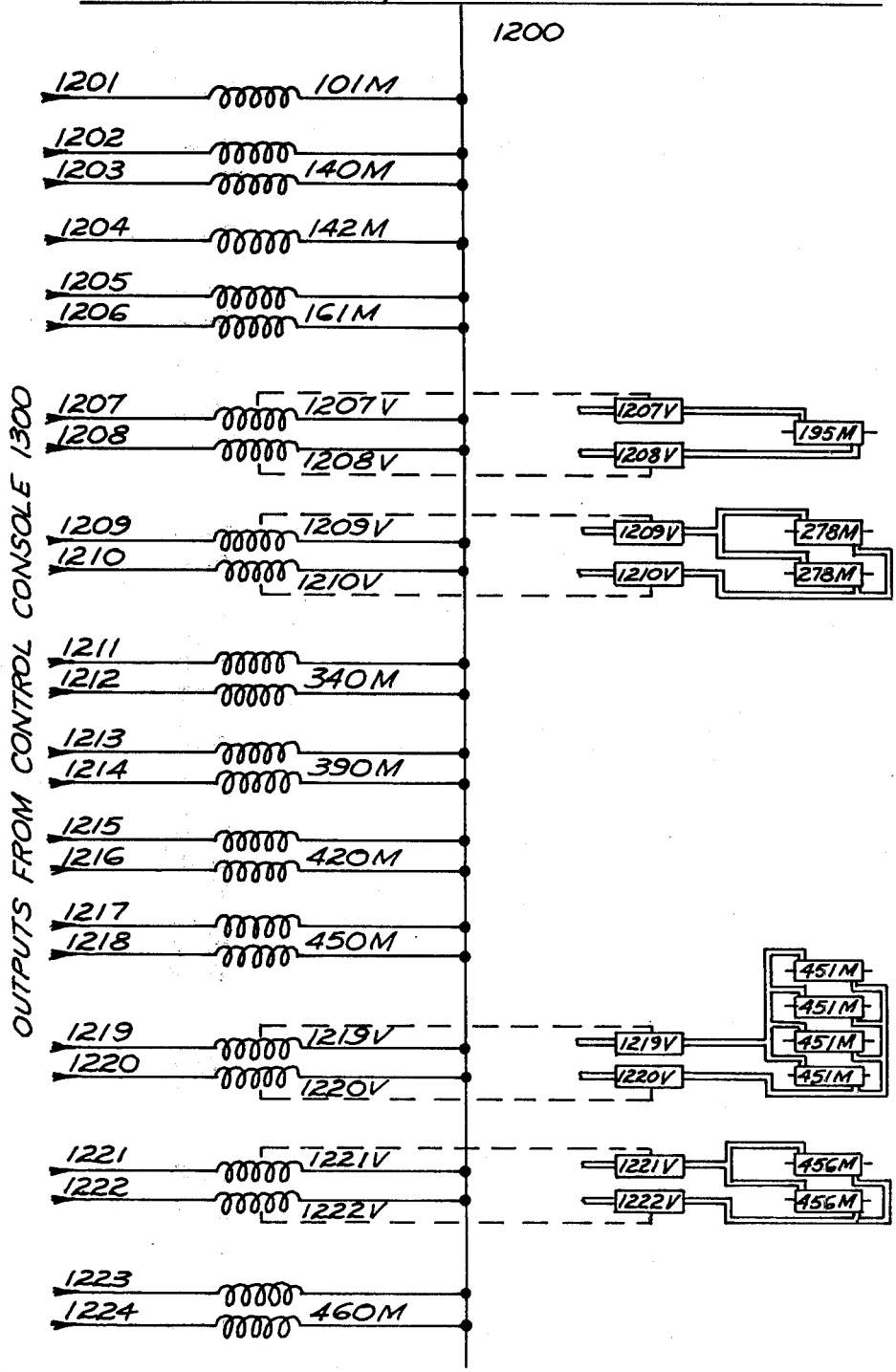
FIGS. 25A, 25B are schematic electrical diagrams tabulating the several outputs from the control console to motors, solenoid operated valves, and a pressure regulator.
Figure 25B:
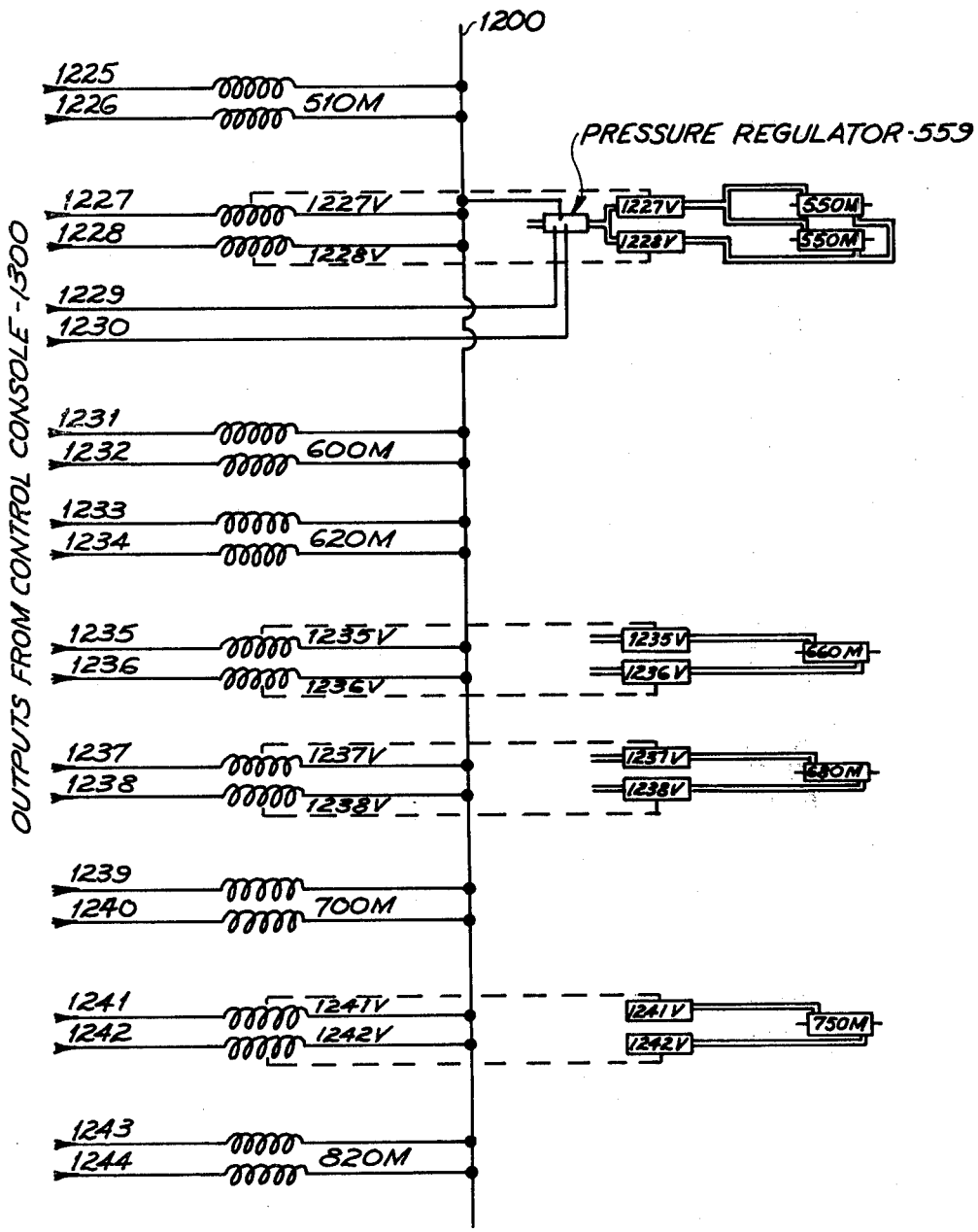

Referring to FIGS. 25A, 25B, the inputs to the several described electric motors, to several solenoid valves which operate the described pneumatic motors and to the pressure regulator are shown schematically as forming outputs from the control console 1300. Each of the shown windings or motors, solenoids and pressure regulator has one conductor connected to a line conductor 1200. The other sides of these windings are connected to a total of 44 console outputs, numbered 1201–1244.

The outputs 1201 connects to the motor 101M. The outputs 1202, 1203 connect to forward and reverse windings of the motor 140M. The output 1204 connects to the motor 142M. The outputs 1205, 1206 connect to forward and reverse windings of the motor 161M.

The outputs 1207, 1208 connect to the windings of two solenoid valves 1207V, 1208V for selectively supplying pressurized air to opposite ends of the pneumatic motor 195M.

The outputs 1209, 1210 connect to the windings of two solenoid valves 1209V, 1210V for selectively supplying pressurized air to opposite ends of the pneumatic motors 278M.

The outputs 1211, 1212; 1213, 1214; 1215, 1216; and 1217, 1218; connect to forward reverse windings of the motors 340M; 390M; 420M; and 450M, respectively.

The outputs 1219, 1220 connect to the windings of two solenoid valves 1219V, 1220V for selectively supplying pressurized air to opposite ends of the pneumatic motors 451M.

The outputs 1221, 1222 connect to the windings of two solenoid valves 1221V, 1222V for selectively supplying pressurized air to opposite ends of the pneumatic motors 456M.

The outputs 1223, 1224 and 1225, 1226 connect to forward and reverse windings of the motors 460M and 510M.

The outputs 1227, 1228 connect to the windings of two solenoid valves 1227V, 1228V for selectively supplying pressurized air to opposite ends of the pneumatic motors 550M.

The outputs 1229, 1230 connect to high and low pressure windings of the pressure regulator 559 for selectively supplying the valves 1227V, 1228V with high or low pressure air.

The outputs 1231, 1232; 1233, 1234; 1239, 1240; and 1243, 1244 connect to forward and reverse windings of the motors 600M; 620M; 700M; and 820M, respectively.

The outputs 1235, 1236; 1237, 1238; and 1241, 1242 connect to the windings of solenoid valves 1235V, 1236V; 1237V, 1238V; and 1241V, 1242V for selectively supplying pressurized air to opposite ends of the pneumatic motors 660M; 680M; and 750M.

The Control Console 1300

Figure 2:
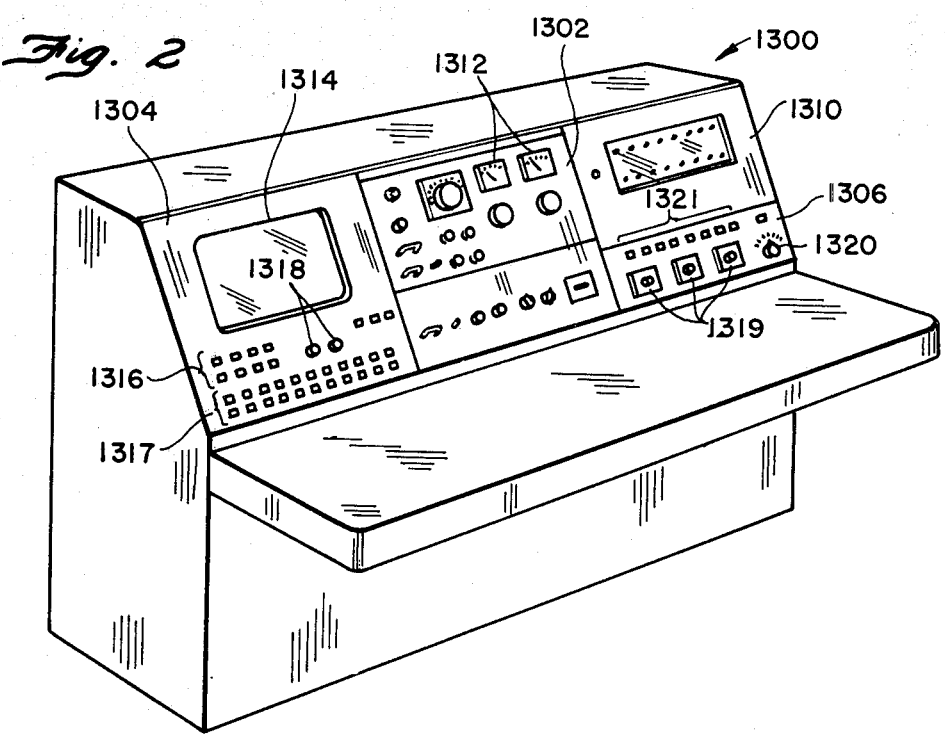
FIG. 2 is a perspective view of the control console of the apparatus shown in FIG. 1.

Referring to FIG. 2, the console 1300 includes a power control panel 1302, an inspection control panel 1304, and a fault indicator panel 1306. The console 1300 are preferably houses an automatic control apparatus for the tire inspector apparatus, as will be explained below.

The power control panel 1302 includes switches and circuit breakers connected for governing the safe operation of the electrical components of the tire inspector apparatus. The power control panel 1302 also includes metered controls 1312 for adjusting the current and voltage supplied to the X-ray tube carried in the housing 702.

The inspection control panel 1304 includes a television screen 1314. The television screen 1314 is connected to the X-ray imaging unit 440 for projecting an image of a tire being inspected onto the television screen 1314 for viewing by an operator.

The inspection control panel 1304 also has functional control elements, including a series of control buttons 1316 connected for manually controlling the scanning functions of the tire inspection apparatus, and for selecting its mode of operation, as will be explained below. It also includes a series of buttons 1317 connected for manually controlling various drive functions of the tire inspection apparatus 100 and the belt conveyors 101, 102.

The inspection control panel 1304 also includes speed controls 1318 for controlling the speed of movement of the X-ray imaging unit 440 and of the tire rotation spindles 600.

The fault indication panel 1306 includes three dials 1319 connected for manually adjusting the tire inspection apparatus to accommodate tires having a prescribed inside diameter, outside diameter, and height. It also includes a bead-spread adjuster 1320. A fault indicator display including eight lights 1321 is provided for indicating malfunctions in the tire inspector apparatus.

The Control System 1325

The control apparatus for the tire inspector apparatus preferably includes a computer 1310, which is mounted in the console 1300. The computer 1310 monitors all functions of the tire inspector apparatus 100 and actuates the control system to drive the tire inspector components in a predetermined manner to perform tire inspection.

Figure 26:
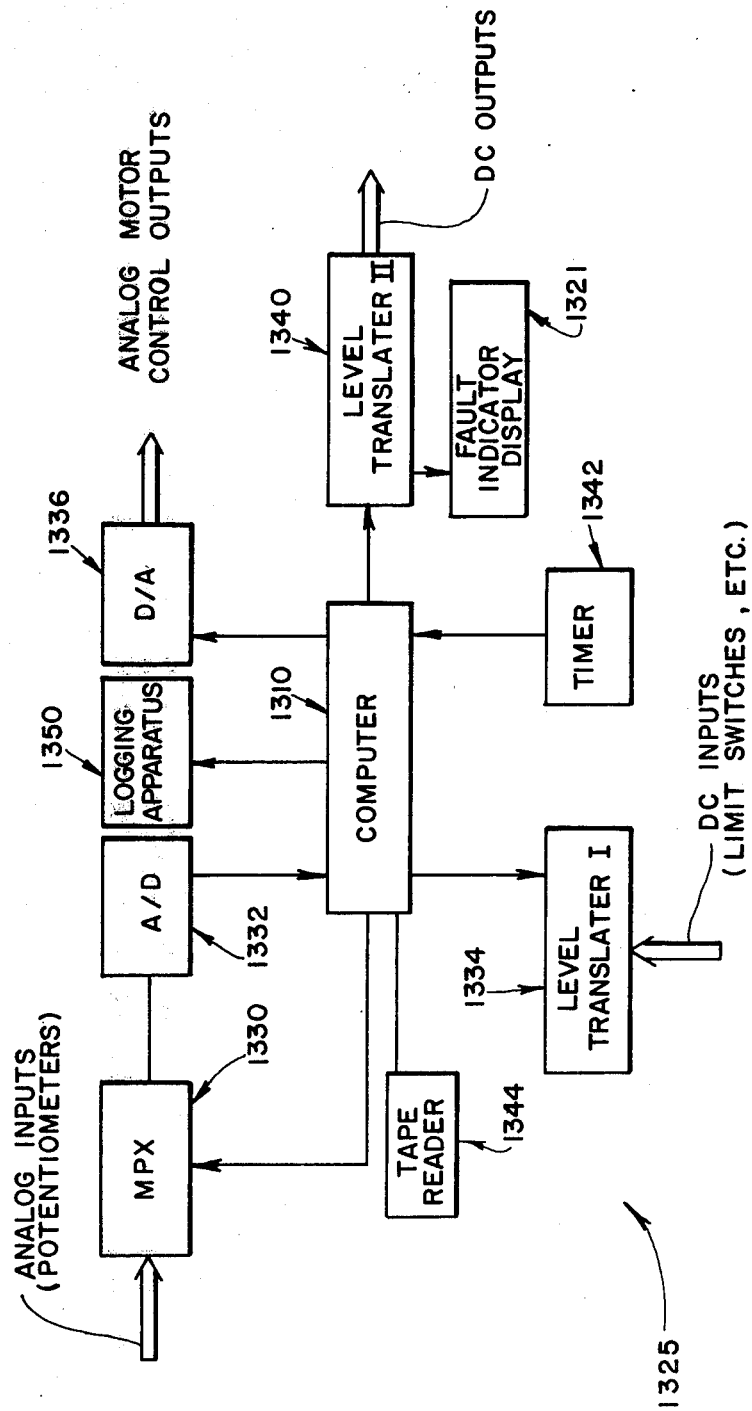
FIG. 26 is a schematic block diagram of the several components of the computer of the control system; and, FIGS. 27A-27E present a schedule of the preferred sequence of operation the tire inspector apparatus.

The control system housed within the console 1300 is shown in block form in FIG. 26. The control system 1325 receives inputs 1001–1040 and 1101–1113 from the several described sensing elements connected to various components of the tire inspector apparatus 100. The sensor inputs indicate conditions associated with the components to which they are connected. The control system 1325 processes the sensor inputs and generates outputs 1201–1244 which actuate the various drive mechanisms of the tire inspector in accordance with the sensed conditions. Other outputs produced by the control apparatus actuate the fault indication display lamps 1321 to indicate certain malfunctions which may occur during an inspection cycle.

The control apparatus, as shown in FIG. 26 includes input conditioning circuitry and output conditioning circuitry. Interposed between the input and the output conditioning circuitry is the computer 1310. The computer 1310 operates upon the input signals 1001–1040 and 1101–1113 according to its program, and generates signals which actuate the output conditioning circuitry to produce the outputs 1201–1244 controlling the tire inspector.

The input conditioning circuitry includes a multiplexer 1330 and an analog to digital converter 1332. The multiplexer receives the analog inputs in parallel and directs them serially to the analog to digital converter. The analog to digital converter produces and directs digital signals representing the analog inputs to the computer. The DC inputs from the limit switches and photocells are directed in parallel to a level translator 1334. The level translator alters the level of the DC inputs to enhance their detectability and presents these signals to the computer.

The output conditioning circuitry includes an analog to digital converter 1336 and a level translator 1340. The analog to digital converter is connected to the computer to receive digital outputs representing motor control signals. The digital to analog converter converts these digital outputs to analog form. These analog motor control outputs are then applied in parallel respectively to the various motors of the tire inspection apparatus to control them according to the computer program and the condition of the input signals. The level translator receives output signals from the computer representing DC outputs which are utilized in operation of the tire inspection apparatus. The level translator alters the level of these outputs to render them suitable for presentation to the various elements of the tire inspection apparatus.

The multiplexer 1330 and analog to digital converter 1332 of the input conditioning circuitry is a Computer Products Model 7460 High Level Analog Input System. The level translator 1334 is a pair of Texas Instruments No. 966495-32 Input Data Modules, in parallel, with optically coupled isolation.

The digital to analog converter 1336 in the output conditioning circuitry is a Computer Products Model 7430 Digital Output Analog System. The level translator 1340 is a Texas Instruments No. 217380-32 Output Data Module.

The computer 1310 is a Texas Instruments Model 960A, with a battery pack to render its read-write memory nonvolatile, and a communication register unit output line expander kit. Timing for the computer is established by a Timer 1342. The timer 1342 is a Texas Instruments No. 214114 Interval Timer connected to the computer.

A tape reader 1344 is connected to the computer 1310 for inputting the program to the computer. The program for the computer 1310 is written on punched paper tape in a known fashion. The tape reader 1344 is suitably a Remex Model RR-6300BAX/66X High Speed Paper Tape Reader.

The fault indicator display lamps 1321 are connected to the computer 1310 to receive signals which indicate the existence and nature of malfunctions in the tire inspection apparatus 100. The malfunction indicative signals are generated when a predetermined circumstance or combination of circumstances exist with respect to the tire inspection apparatus which are dangerous, and/or potentially destructive to the machinery. The computer 1310 produces malfunction indicative signals in response to the input signals 1001–1040 and 1101–1113 received by the computer by the sensing devices. The program input to the computer by the tape reader 1344 determines the prerequisites for production of such malfunction indicative signals, and the nature of those signals.

The fault indicator display lamps 1321 are illuminated in patterns according to a code which enables identification of the nature of the detected malfunction from the pattern.

Alternately, the fault indication display can be a print-out device connected to the computer. In such an embodiment, the program input to the computer by way of the tape reader conditions the computer to produce signals which actuate the print-out device to write out directly legible diagnostic messages to the operator indicating the nature of the malfunctions.

Preferably, a logging apparatus 1350 may be connected to the computer 1310. The logging apparatus 1350 is useful in maintaining a permanent record of the history of the tire inspection operations performed by the tire inspection apparatus. It is also useful in transmitting data relating to tire inspections to remote locations for recording and/or immediate observation. Such logging apparatus suitably includes peripheral devices such as a printer machine, data modems, and magnetic tape transport, the selection of which is withint the level of ordinary skill.

The mechanical functions of the tire inspection apparatus 100 are all capable of actuation independently of each other. Moreover, the control apparatus drives and monitors all functions and combinations of functions simultaneously. Therefore, the sequence of operations and functions is fully controllable by the program input to the control apparatus, within the mechanical limitations of the tire inspection apparatus. The operation can also be completely automatic.

The sequence of operations of the tire inspection apparatus is determined according to the nature of the particular program input to the computer. It is therefore not necessary to make mechanical alterations to the apparatus to alter the mode of its operation. The only down time required to alter the operational sequence is that which is necessary to change the program, i.e., to remove one paper tape from the tape reader and substitute another.

Due to the nonvolatile nature of the computer memory, a power down, power failure or deliberate interruption of the automatic execution of tire inspections will now upset the operation of the tire inspection apparatus. Upon return of power, ot termination of the program interruption, the system resumes its automatic operation at the same point at which operation ceased due to the power cut-off or interruption.

Operation

The control apparatus 1325 operates the tire inspection apparatus 100 in accordance with an automatic mode as determined by the computer program. A flow chart setting forth the operative functions of a suitable automatic operating mode of the tire inspection apparatus is shown in FIGS. 27A–27E. The flow chart also describes the functional commands of a suitable program for executing the automatic mode.

To initiate operation of the inspection apparatus 100, a punched paper tape representing a program is placed in the high speed tape reader 1344. The program is run through the tape reader 1344 to input it to the computer 1310 thereby enabling the computer 1310 to operate the tire inspection apparatus 100 in accordance with the program.

The automatic mode proceeds in accord with the following steps:

(1) The tire is delivered to the roller conveyor 140;

(2) The arm assemblies 161 and width sensor bar 210 to measure and center the tire;

(3) The image unit 440, spindles 600, and their associated components are prepared for entry of the tire to the shielded enclosure 275;

(4) The tire is delivered to the enclosure 275.

(5) The imaging unit 440 and X-ray tube assembly 700 moves to an inspection position and the spindles 600 engage the tire;

(6) The imaging unit 440, X-ray tube assembly 700 and spindles 600 cooperate to produce images of the inspected regions of the tire;

(7) The spindles 600 disengage the tire and the imaging unit 440 and X-ray tube assembly 700 withdraw;

(8) The tire is discharged from the enclosure 275 and a subsequent tire is admitted.

The first general operation of the automatic mode is to deliver tires to be inspected one by one onto the centering table roller conveyor 140 for dimensional measurement and centering. Referring to FIG. 27A, the first step in executing the program is for the control apparatus to generate a motor control signal to actuate the motor 101M to move a tire along the belt conveyor 101 until it interrupts the light beam incident on the photocell $101P_1$. The control apparatus does this by monitoring the output of the photocell $101P_1$, and generates a motor control signal actuating the motor 101M in response to the beam being incident on that photocell. The actuation of the motor 101M continues at least until the conveyor 101 delivers a tire to a point at which it interrupts the beam incident upon the photocell $101P_1$.

If the following preconditions are fulfilled, the control apparatus 1325 continues the actuation of the motor 101M to move the tire onto the centering table 120, and actuates the motor 142M to advance the tire on the centering table:

(1) The photocells $142P_1$ and $142P_2$ to produce signals indicating that the centering table 120 is clear of objects;

(2) The potentiometer 161P produces a signal to the control apparatus indicating that the arm assemblies 161 are open to at least a predetermined extent to receive a tire between them;

(3) The potentiometer 195P produces a signal to the control apparatus indicating that the width sensor bar 210 is raised to a predetermined extent to receive a tire;

(4) The limit switches $190S_1$ and $190S_2$ do not indicate contact by the arm assemblies 161 with an object;

(5) The limit switch 195S produces a signal indicating the width sensor bar is not engaging an object;

If any of these preconditions are not fulfilled, the control apparatus, upon the advance of a tire to the photocell 101P, deactuates the motor 101M and will not actuate the motor 142M until all the preconditions are satisfied.

If these preconditions are met, the tire is moved along the centering table roller conveyor 140 until it interrupts the light beam on one of the photocells $142P_1$ and $142P_2$. Such an interruption indicates to the control apparatus 1325 that the tire has arrived at a predetermined point called a "centering station" on the centering table conveyor 140. When a tire is in the centering station the arm assemblies 161 and width sensor bar 210 can engage the tire to measure and center it. At this point, the control apparatus produces a motor control signal to deactuate the motor 142M to stop the rotation of the centering table conveyor rolls 142.

Assuming that the preconditions are satisfied, and the tire is advanced onto the roller conveyor 140, the control system 1325 actuates the motor 101M to continue running and to advance a subsequent tire along the belt conveyor 101. The belt conveyor 101 continues to run until the photocell $101P_1$ detects the arrival of the subsequent tire at the end of the belt conveyor 101. The control apparatus 1325 then produces a motor control signal deactuating the motor 101M.

The motor 101M remains deactuated until later in the automatic mode, at which time it is reactuated, as will be explained below.

When the tire has arrived at the centering station the control apparatus 1325 produces control signals to first move the centering arms 161 inwardly to measure the outside diameter and to center the tire. The arm assemblies 161 are moved inwardly toward the tire in response to the interruption by the tire of the light beam of the photocells $142P_1$, $142P_2$. The control apparatus does this by producing a motor control signal actuating the motor 161M to move the arm assemblies 161 toward the tire. When both arm assemblies 161 contact the tire, the switches $190S_1$ and $190S_2$ provide DC output signals to the control apparatus, in response to which the control apparatus generates a motor control signal which stops the motor 161M. The potentiometer 161P is then producing an analog signal respresentative of the outside diameter of the tire, which signal is transmitted to the control apparatus and its value stored for later use.

The simultaneous inward motion of the arms 161 also centers the tire on the roller conveyor 140. This is needed to assure that the tire, when later moved into the enclosure 275, will move along a feed path to position its central axis for proper engagement by the spindles.

Upon actuation of the switches $190S_1$ and $190S_2$, the control apparatus also actuates the motor 161M to move the arms 161 away from each other.

The control apparatus then produces a signal actuating the motor 190M to move the width sensor bar downwardly. The width sensor bar continues to move downwardly until it contacts the tire sidewall. At that point, the switch 195S produces a signal to the control apparatus indicating such contact. In response to the signal from the switch 195S, the control apparatus examines and stores a signal respresenting the signal produced by the potentiometer 195P, which represents the width of the tire after the switch 195S senses tire contact, the control apparatus actuates the pneumatic motor 195M to move the width sensor bar upwardly to the upper limit of its range of travel.

When the arm assemblies 161 move apart to a predetermined degree, as indicated by the analog signal of the potentiometer 161P, the control apparatus actuates the motor 278M to open the doors 278 of the shielded enclosure 275. The control system also actuates the motor 161M to stop the arms 161 after reaching the predetermined separation.

The control apparatus then moves the imaging unit 440 laterally outwardly to clear both the measured outside diameter of the tire and the width of the main conveyor 450. The lateral position of the imaging unit 440 is monitored by the analog signals produced by the potentiometers 340P and 420P, respectively. In response, the control system produces motor control signals to actuate the motors 340M and 420M to move the imaging system carriage 340 and imaging system sub-sub-carriage 420 outwardly until the imaging unit 440 is laterally outside the measured tire outside diameter and the main conveyor frame 451.

The control system actuates the pressure regulator 559 to set the spindle pressure as a predetermined function of the measured tire width and outside diameter. This function establishes the proper spindle pressure according to the size, and therefore the weight, of the tire.

The control apparatus actuates the motor 820M to move the traveling positoning switch assembly 820 to a position for engaging the tire when the tire has moved into the enclosure. The position is selected such that it is appropriate for engagement of the tire by the spindles, and for subsequent inspection.

The X-ray tube sub-carriage 660 is then moved laterally if needed to locate the X-ray tube assembly 700 within the maximum expected inside diameter of the tire when positioned for engagement by the spindles, at the point established by the positioning switch assembly.

The control apparatus generates a signal representing the maximum inside tire diameter expected, as a predetermined function of the sensed tire width and outside diameter. The control apparatus monitors the lateral position of the X-ray carriage by a signal produced by the potentiometer 620P. The control system, in response to comparison to these values, produces a motor control signal to actuate the motor 620M to move the X-ray carriage 620 to locate the tube inside the maximum expected inside diameter of the tire.

The control apparatus 1325 compares the position of the imaging system sub-carriage, as indicated by the signal generated by the potentiometer 390P, with the value of that signal generated with the sub-carriage located in the central plane of the tire in its inspection position. In response to this comparison, the control apparatus produces a motor control signal to actuate the motor 390M to move the image system sub-carriage to locate the imaging system at 0° with respect to the central plane of the tire to be inspected.

The control apparatus 1325 also senses the angle of emission of X-radiation from the X-ray tube assembly 700 by the analog signal produced by the potentiometer 700P. The control apparatus compares that signal with the corresponding value when the X-ray emission angle is at zero degrees, (horizontal) and products a motor control analog signal to actuate the motor to pivot the X-ray tube to the zero degree position.

When the control system has sensed the imaging system 440 at the 0° position, it produces motor control signals to actuate the motor 460M and the motor 140M to move the main conveyor gear racks 460 and pivot the left end of the centering table roller conveyor 140 to assume a matching elevation which is a predetermined function of the tire width sensed. The predetermined height is a function of the width of the tire, such that the mid-plane of each tire will enter the shielded enclosure at one predetermined level. Also, the motor 510M is actuated to cause the spindle carriages 510 to separate vertically. The purpose of this step is to position the centering table 120 and the main conveyor 450 such that the tire moves smoothly onto the main conveyor from the centering table. The purpose is also to simultaneously position the main conveyor to place the incoming tire at an elevation appropriate for mounting the tire on the spindles 600 for subsequent inspection.

The tire inspection apparatus then advances the tire into the enclosure 275 for inspection.

The control apparatus senses whether the doors 278 are unobstructed as indicated by DC signals from the photocells $278P_1$ and $278P_2$. If the doors 278 are unobstructed, the control apparatus, in response to fulfillment of the following additional preconditions, produces analog motor control signals to actuate the motors 142M and 452M to move the tire from the roller conveyor 140 to the main conveyor:

(1) The positioning switch assembly 820 is appropriately positioned as a function of tire outside diameter;

(2) Imaging system X-ray tube emission angle is set at 0° to the central plane of the tire;
(3) The main conveyor 450 and center table conveyor 120 are positioned at a level to receive the tire as specified above;
(4) The spindles 600 are separated, as indicated by the potentiometer 510P, by an amount which is a function of tire width, to clear the tire.

The control apparatus halts the tire when it has progressed along the main conveyor 450 to a predetermined position. The predetermined position is chosen as a position at which the tire is located for mounting on the spindles 600 with its central axis along a predetermined line in the inspection station.

The positioning switch assembly 820 provides signals to the control apparatus causing it to stop the tire at the predetermined location. Those signals are generated in response to DC signals produced by the positioning switch assembly 820.

The positioning switch assembly 820 depends from above the main conveyor and engages the tire as it moves along the main conveyor. When the positioning switch assembly 820 engages the tire, the arms 831-833 pivot until the limit switch $452S_1$ is actuated. This takes place when the tire reaches a location approaching the predetermined location. The limit switch $452S_1$ produces a signal to the control apparatus, in response to which the control apparatus reduces the speed of the main conveyor 450, by a change in the signal actuating the motor 452M.

When the tire has advanced at this slower speed to the predetermined location called the "inspection station", the arms 831-833 have pivoted to a position where the limit switch $452S_2$ is actuated. The limit switch produces a signal to the control apparatus, in response to which the control apparatus produces a motor control signal deactuating the motor 452M, stopping the tire at the predetermined position.

In response to the positioning switch assembly 820 indicating the advancement of the tire to the inspection station, the control apparatus then generates a motor control signal to actuate the motor 278M to close the doors of the shielded enclosure 275. When the doors 278 are closed, a motor control signal is produced to actuate the motor 750M to uncover the X-ray tube.

The control apparatus 1325 then produces a signal to actuate the motor 820M to move the positioning switch assembly to a removed position about five inches forwardly of the leading edge of the tire, as sensed by the potentiometer 820P.

Upon closure of the doors 278, any subsequent tire located at the end of the belt conveyor 101 is advanced onto the centering table 120 for centering and measurement. The control apparatus, in response to the signals from the switch $278S_2$, actuates the motors 101M and 142M to move the waiting subsequent tire onto the centering table. The subsequent tire is then centered and its outside diameter measured by the arm assemblies 161. Its width is sensed by the width sensor assembly 195.

Meanwhile, the tire inspector apparatus moves the spindle carriages 510 to insert the spindles 600 into the annulus of the tire which is to be inspected. This procedure is described in FIG. 27B of the flow chart.

The control apparatus 1325 then produces a motor control signal which actuates the pneumatic motors 550M to move the spindle arms 550 outwardly to engage the tire beads with the predetermined amount of spindle pressure established by the setting of the pressure regulator 559. The potentiometer 550P connected to the spindle arms 550 produces an analog signal indicating the degree of extension of the spindles 600 when the extension stops, and consequently indicates the inside diameter of the tire. This signal is also directed to the control apparatus for storage and later use.

The control apparatus then generates motor control signals to actuate the motors 451M to lower the conveyor frame 451 a distance of about one and one-half inches as indicated by the limit switch $451S_2$. The control apparatus also generates a motor control signal to actuate the motor 456M to lower the main conveyor movable frames 456 to their lowermost position, as indicated by conditions of the limit switches $456S_2$ and $456S_1$.

The potentiometer 510P produces an analog signal to the control apparatus which indicates the degree of separation of the upper and lower spindle carriages 710.

The motor 510M controls the degree of separation of the spindle carriages 510. The control apparatus generates a motor control signal which actuates the motor 510M to separate the spindle carriages to axially spread the beads of the tire supported on the spindles. The degree of desired bead separation is determined by the control system as a function of the tire width as sensed by the control apparatus, and of the operator setting on the beadspread multiplier switch 1320. The degree of beadspread is monitored by the potentiometer 510P.

The tire inspector apparatus 100 then maneuvers the X-ray tube assembly 700 and imaging unit 440 to effect inspection of the tire.

The potentiometer 620P is connected to the X-ray carriage 620 and generates an analog input signal to the control apparatus 1325 indicating the position of the X-ray carriage. The control apparatus actuates the motor 620M to move the X-ray carriage to position the X-ray tube housing 701 over the tire annulus, within the inside diameter of the tire.

The control apparatus also generates an analog motor control signal which actuates the motor 340M to move the imaging system carriage 340 to a point at which the center of radius of the C-arms is at that point where the X-ray tube focal point will be positioned for scanning.

The X-ray tube focal point is initially positioned as a function of the inside diameter of the tire. As will be more fully explained below, when a relatively large tire is to be inspected, the X-ray tube is preferably initially positioned for scanning with its focal point approximately on a cylinder defined by the inner edges of the tire beads. When a small tire is to be inspected, the initial focal point position is at a predetermined point slightly inside that cylinder.

The initial tube focal point location is thus determined by the control system as a function of the analog signals from the potentiometer 550P. The control system generates the analog signal to actuate the motor 620M to move the X-ray tube carriage 620 to properly locate the tube focal point at the preferred initial position in response to this analog input.

Preparatory manipulation of the tube for inspection proceeds. If the control apparatus senses, by way of the limit switch $750S_2$, that the X-ray tube is fully uncovered, the control apparatus produces a motor control signal which actuates the motor 680M to move the X-ray sub-subcarriage 680 to lower the tube.

After the X-ray tube housing assembly 700 is lowered into the tire annulus, the control apparatus under certain conditions generates a motor control signal to actuate the motor 660M to move the X-ray subcarriage 660 to geometrically offset the X-ray tube housing assembly by 1½ inches. The direction of this offset is parallel to the tire feed path. The offsetting motion moves the focal point of the X-ray tube to a position along a line perpendicular to the feed path and extending through the central axis of the tire at the inspection station. This offsetting motion is performed only in instances in which the tire has an inside diameter of 13 inches or more.

FIGS. 21A through 21C illustrate the operation of the X-ray subcarriage 660 in providing for the geometric offset. The size of the X-ray housing assembly 700 is such that it can barely be admitted to the annulus of a tire with a 10-inch inside diameter, which is the inside diameter of the smallest inspectable tire. The position which the X-ray tube housing assembly 700 must assume to permit its entry into a 10-inch inside diameter tire causes the tube focal point to be displaced from the central axis of the tire relative to the tire feed path.

If the tire inside diameter is sufficiently large, typically about 13 inches or longer, the housing assembly 700 is offset by the X-ray subcarriage 660 to place the tube focal point along the line perpendicular to the feed path and extending through the central axis of the tire.

If the tire inside diameter is smaller than 13 inches, the inside diameter of the tire will not accommodate the 1½ inch offset movement of the housing assembly 700. Such movement would cause the housing assembly 700 to collide with the tire beads. In such instances, the offset motion is not performed to avoid damage to the housing assembly 700.

It is desirable to position the focal point of the X-ray tube between the tire beads on a cylinder defined by the beads. For this purpose, the X-ray carriage 620 (partially illustrated in FIG. 21A by the elements 627, 628) is moved, after offset, to position the focal point on this cylinder. It is possible to position the focal point precisely on this cylinder only in the case of tires having an inside diameter large enough to accommodate geometric offset. The motion of the X-ray tube focal point in the case of such a large tire is shown by the arrows in FIG. 21C. The horizontal arrow illustrates movement of the focal point during the offsetting step. The vertical arrow pointing downwardly illustrates the further movement of the X-ray tube focal point outwardly until it reaches the cylinder defined by the tire beads.

The motion of the focal point in the instance of small tires (inside diameter less than 13 inches) is shown in FIG. 21B. In this case, there is no geometric offset, and the focal point is not moved to the line through the tire center axis. The only motion permitted for the focal point in this instance is motion imparted by the X-ray carriage 620 toward the tire beads.

The actual scanning of the tire is then enabled if the control apparatus 1325 determines that each of the following conditions is fulfilled:

1. The potentiometer 820P indicates that the positioning switch assembly 820 is in its removed position, five inches forward the tire;
2. The X-ray tube assembly 700 is lowered, and offset, if possible as indicated by the input signals to the control system generated by the limit switches 680S$_2$ and 660S$_2$, respectively;
3. The C-arms 380, 381 are positioned with their centers of radius along a line through the focal point of the X-ray tube, as indicated by the analog input signals to the control apparatus from the potentiometers 340P and 620P; and
4. The main conveyor frame 451 and the movable frames 456 are lowered, as indicated by the DC input signals to the control apparatus from the limit switches 460S$_2$, 460S$_1$, 456S$_2$ and 456S$_1$, respectively.
5. The imaging unit is located on the C-arms 380, 381 to 0° with respect to the central plane of the tire, as indicated by the analog output from the potentiometer 390P.

The control apparatus then establishes a "limited scheduled interrupt" scanning mode, which turns over to the operator for a time a number of manual tire inspection scanning functions. The operator can control these functions manually by depressing the various scanning function buttons 1316.

The functions of scanning which are turned over to manual operation by the operator are the following:

1. Actuation of the motor 510M to control the spindle carriages 510 to adjust the beadspread of the tire;
2. Actuation of the motor 600M to rotate the tire in either direction by rotation of the spindles; the speed of this rotation can be controlled by the setting of the switch 1326a.
3. Actuation of the motors 340M, 390M, 420M, and 440M to control the position and magnification of the imaging unit 440 to manipulate the imaging unit to form an image of the X-rays passing through the tire at any of a range of positions about the tire. Motion of the imaging system sub-carriage 390 is speed controlled, by the setting of the switch 1326b.
4. Actuation of the motors 620M, 660M, 680M, and 820M to control the X-ray tube pivot, and motion of the X-ray carriage 620, sub-carriage 660, and sub-sub-carriage 680, to direct X-rays to desired portions of the rotating tire to facilitate inspection of the entire tube, or of any selected part of it.

The control apparatus 1325, during the "limited scheduled interrupt" scanning mode, synchronizes some of the movements of the X-ray tube and of the imaging unit. The control apparatus senses the pivotal position of the X-ray housing 701 by the analog signal from the potentiometer 700P, and produces a motor control signal to the motor 390M to move the imaging unit sub-carriage to move the imaging unit along the C-arms 380, 381 to maintain its screen in the path of the X-rays emitted by the tube.

The control apparatus also maintains the imaging carriage C-arms with their centers of radius along a line through the X-ray tube focal point. This is done by sensing the position of the X-ray carriage as represented by the analog signal from the potentiometer 620P, and the C-arm position from the potentiometer 340P. The control system causes the image system carriage to move the C-arms 380, 381 in response to changes in position of the X-ray carriage 620 indicated by the signal from the potentiometer 620P. This feature maintains the magnification of the imaging system constant notwithstanding movement of the X-ray tube.

As more fully explained below, the control apparatus 1325 protects the apparatus and operator by refusing to respond to scanning button commands which would execute potentially dangerous or destructive movements.

X-rays emitted from the X-ray tube pass through portions of the tire and are received by the imaging unit. The imaging unit converts the pattern of received X-radiation to video formatted electrical signals representing an image of the tire portions, through which the X-rays have passed. These electrical signals are directed to the television receiver 1314, on the console 1300. The television receiver converts the signals to a visual image of the tire portions showing certain features of internal tire construction, which may be viewed by the operator at the console.

When the scanning of the tire has been completed to the satisfaction of the operator, the operator can depress a scanning function button on the inspection control panel 1304 which indicates the completion of scanning, and produces an automatic mode resumption signal to the control apparatus. The depression of this button actuates the control apparatus 1325 to resume automatic operation of the tire inspector apparatus. This subsequent automatic operation includes discharging the inspected tire from the shielded enclosure 275 and admitting a subsequent tire to the shielded enclosure for inspection.

When the operator depresses the automatic mode resumption button indicating the completion of inspection of the tire, the control apparatus 1325 stops all motion of the tire inspector apparatus 100. It does this by way of the analog motor control output signals.

The control apparatus then produces analog motor control signals (FIG. 26) to actuate the motors 340M and 420M to move the image system carriage 340 and image unit 440, respectively, to clear the tire outside diameter and the main conveyor.

As explained above, the subsequent tire is received on the centering table roller conveyor during inspection of the first tire, where the subsequent tire is centered and measured.

The motor 660M is actuated to move the X-ray sub-carriage to straighten offset which may have been assumed by the X-ray tube assembly 700 during inspection of the first tire. The control apparatus then produces a motor control signal to actuate the motor 620M to move the X-ray carriage 340 to place the X-ray tube assembly 700 housing to clear both the inside diameter of the first tire and the maximum expected inside diameter of the subsequent tire, as determined by measurement of the outside diameter and width of the subsequent tire.

The control apparatus then produces analog motor control signals to actuate the motors 700M and 390M to pivot the X-ray tube housing 701 to 0° with respect to the central plane of the first tire, and cause the image system sub-carriage 390 to move the imaging unit also to 0°. The control apparatus also generates a motor control signal to actuate the motor 510M to move the spindle carriages toward each other to further insert the spindle 600 to reduce the beadspread of the first tire to 3.5 inches, which insertion is not enough to damage the X-ray tube assembly 700.

Provided that the analog input signal from the potentiometer 620P indicates that the X-ray tube is within the first tire inside diameter, that the potentiometer 700P indicates the X-ray tube housing 701 is pivoted to 0° and that the potentiometer 390P indicates the image assembly 440 is positioned at 0° with respect to the central plane of the tire, the control apparatus 1325 generates a motor control signal which actuates the motor 680M to move the X-ray sub-sub-carriage 680 to raise the X-ray tube assembly 700 out of the first tire.

When the limit switch 680S₂ indicates that the tube is fully raised, the control apparatus generates analog motor control signals to actuate the motors 340M and 420M to move the image system carriage 340 and image system sub-sub-carriage 420 to position the image system assembly to clear the outside diameters of both the first and subsequent tires (sensed by the signal from the potentiometer 161P to the control apparatus), and the main conveyor.

The control apparatus then produces a motor control signal to actuate the motor 510M to momentarily insert the spindles 600 to their least separated position. This operation is performed provided that the signal generated by the potentiometer 620P produces an analog input to the control apparatus indicating that the X-ray tube is positioned to clear the inside diameter of the first tire.

The control apparatus also produces an analog motor control output signal to actuate the motors 451M and 456M to raise the main conveyor frame 451 and the movable frames 456, respectively, to the levels at which they were set to admit the first tire. This level, as explained above, is a function of the width of the first tire. The control apparatus also generates a motor control signal which actuates the motor 820M to close the shield over the X-ray tube.

The control apparatus then produces a motor control signal which actuates the motor 278M to open the doors 278 of the shielded enclosure 275.

The control apparatus then produces a motor control signal to actuate the motor 550M to move the spindle arms 550 to fully retract the spindles, provided:

1. The spindles are moved to their least separated position, as indicated by the analog input to the control system from the potentiometer 510P;

2. The X-ray tube is fully raised, as indicated by the DC input to the control apparatus from actuation of the limit switch 680S₁;

3. The movable frame 456 is in its uppermost position, as indicated by the DC inputs to the control apparatus from the limit switches 456S₁ and 456S₂;

4. The main conveyor frame 451 is fully raised as indicated by the signal to the control apparatus from the limit switch 451S₁.

The control apparatus then generates an analog signal directed to the pressure regulator 559 to establish the spindle pressure from the subsequent tire, determined in accordance with the measured outside diameter of the subsequent tire. The control system also generates a motor control signal which actuates the motor 510M to remove the spindle carriages to their most separated positions, as indicated by the potentiometer 510P.

If the width of the first tire exceeds that of the subsequent tire by more than a predetermined amount, a first procedure is followed to remove the first tire from the enclosure before admitting the subsequent tire. If the width of the first tire does not exceed that of the subsequent tire by the predetermined amount, a second procedure is followed.

The first procedure is necessary when the first tire is substantially wider than the subsequent tire. The main conveyor is elevated during admission of each tire to put the mid-plane of each tire at a predetermined level. This level is one which enables the mounting of the tire on the spindles for inspection.

If the first tire has substantially greater width than the subsequent tire, the mproper main conveyor level for the subsequent tire is inappropriate for admission of the subsequent tire. The larger tire, if exited at the level set for the smaller tire, will run afoul of the doors 278 of the shielded enclosure 275 or other parts of the tire inspector apparatus.

The first procedure, as described in FIG. 27D, includes the generation of a motor control signal to actuate the motor 450M to drive the main conveyor 450 to move the first tire out of the shielded enclosure and onto the belt conveyor 102, which carries it away for further attention. This operation is enabled contingent upon indicating that the doors to the shielded enclosure are open.

If there is no subsequent tire on the centering table, the control apparatus 1325 actuates the motor 278M to close the door 278 to the enclosure after exit of the first tire, as indicated by the signal produced to the control apparatus by the photocell 278P$_2$.

If, however, a subsequent tire is located on the centering table 120, the control apparatus then produces motor control signals to actuate the motors 460M and 140M to reposition the main conveyor 450 and the centering table 120 at the proper level for admitting the subsequent tire as determined by the width measurement of the subsequent tire. The control apparatus also generates a motor control signal to actuate the motor 550M to retract the spindles to assure they are in fact already retracted. The control apparatus then actuates the motor to position the position switch assembly 820 to stop the progress of the subsequent tire along the main conveyor 450 at a point to enable its engagement with the spindles 600.

The control apparatus then generates motor control signals to actuate the motors 452M and 142M to drive the main conveyor and the centering table roller conveyor to move the subsequent tire from the centering table 120 into the shielded enclosure 275 on the main conveyor.

The operation of the tire inspection apparatus 100 then returns to the point indicated as "K" in portion of the flow chart of FIG. 27B, and proceeds therefrom in the fashion as explained above.

A second procedure for exiting the first tire is executed if the first tire width does not exceed that of the subsequent tire by the predetermined amount, so that the main conveyor 450 may be positioned to simultaneously exit the first tire and admit the subsequent tire.

In the second procedure, the control apparatus 1325 generates motor control signals to actuate the motors 450M and 142M to drive the main conveyor and the centering table roller conveyor to simultaneously exit the first tire and enter the subsequent tire, if the following preconditions are met:

1. The switches 278S$_1$ indicate that the doors are open;
2. The potentiometer 820P indicates that the positioning switch assembly 820 is positioned as a function of the outside diameter of the subsequent tire;
3. The potentiometer 510P indicates the spindles 600 are separated to clear the subsequent tire;
4. The potentiometers 340P and 420P indicate that the image system carriage 340 and sub-sub-carriage 420 are respectively positioned to enable the image unit to clear the outside diameters of the first and subsequent tires and the outer boundary of the main conveyor.

The control apparatus 1325 then generates motor control signals to actuate the motors 460M and 140M to move the main conveyor 450 and centering table roller conveyor, 140, respectively, to a position which, determined in accordance with the measured width of the subsequent tire, positions the subsequent tire at a level for engaging the spindles for subsequent inspection. The procedure then resumes at point "L" on FIG. 27B of the described flow chart.

Interrupt Mode

The machine operator, by depressing a button on the inspection control panel 1304, can suspend the automatic mode of operation of the apparatus 100, as described above, and go instead to a manual or "interrupt" mode of operation. In the interrupt mode, the operator may actuate the apparatus 100 manually to perform a number of functions, by depressing appropriate buttons 1320 on the panel 1304.

The operator can initiate operation in accordance with the interrupt mode by pressing the interrupt button 1304a on the inspection control panel 1304 either while the tire is being scanned, or at a point in the program during which the tire is not being scanned.

If the interrupt mode is initiated during a period in which the tire is not being scanned, the control apparatus enables the operator to actuate several of the components of the apparatus 100 according to a first interrupt procedure. The permitted functions are directed to (1) moving the tire inspector components to prepare for entry of a tire, and (2) entering and engaging the tire for inspection.

According to the interrupt procedure the operator can manually actuate the control apparatus to perform the following preparatory functions:

1. Produce a motor control signal which actuates the motor 620M to move the X-ray carriage 620 to move the tube assembly 700 laterally with respect to the tire feed path;

2. Produce motor actuation signals to actuate the motors 340M and 420M to move the imaging unit carriage 340 and sub-sub-carriage 420 outwardly, respectively, away from the main frame;

3. Produce a motor control signal to actuate the motor 390M to move the imaging system sub-carriage to move the imaging unit along the C-arms 380, 381;

4. Produce a motor control signal to actuate the motor 660M to move the X-ray sub-carriage 660 in a direction to eliminate the offset of the X-ray tube by moving the tube parallel to the direction of tire feed movement along the main conveyor;

5. Produce a motor control signal to actuate the motor 680M to move the X-ray sub-sub-carriage 680 to raise the X-ray tube assembly 700 toward its fully raised position;

6. Produce a motor control signal which actuates the motor 550M to move the spindle arms 550 to retract the spindles to their fully retracted positions;

7. Produce a motor control signal which actuates the motor 510M to separate the upper and lower spindle carriages.

Having initiated the interrupt mode at a time when the tire is not being scanned, the control apparatus 1325 permits the operator to perform the above functions (1–7) in the order designated, but in no other order. To execute any of these functions, all the preceding functions must have already been performed, either in the interrupt mode, or previously during automatic operation. The operator cannot reverse the sequence of the above steps.

If the seven preparatory functions are executed by the operator in the interrupt mode, or by the inspector apparatus in the automatic mode, a number of other functions are then enabled, in interrupt mode. These include the manual initiation of motor control signals by the control apparatus 1325 to perform the following functions, relating to entry and engagement of the tire for inspection:

8. Actuating the motor 142M to operate the centering table roller conveyor, 140, or to stop such operation;
9. Actuating the motor 161M to operate the centering arms 161 in either direction;
10. Actuating the motor 190M to move the tire width sensor bar in an upward or downward direction;
11. Actuating the motor 456M to move the movable frames 456 in an upward direction only;
12. Actuating the motor 460M to change the height of the main conveyor gear racks;
13. Actuating the motor 140M to pivot the centering table roller conveyor 140 up or down;
14. Actuating the motor 452M to operate or stop the driving of the rollers of the main conveyor 450;
15. Actuating the motor 451M to move the main conveyor frame 451 in an upward direction;
16. Actuating the motor 750M to move the X-ray tube shield 750 to cover the tube;
17. Actuating the motor 278M to open and close the doors 278, opening being permitted only if the X-ray tube is covered.

Once the enclosure is prepared to receive a tire and a tire is subsequently entered manually in the interrupt mode, the operator may then manually execute several additional scanning preparatory steps. These scanning preparatory steps comprise causing the control apparatus to generate motor control signals which:

1. Actuate the motor 510M to move the spindle carriages to move the upper and lower spindles to within a predetermined distance of one another;
2. Actuate the motor 550M to extend the spindles;
3. Actuate the motor 460M to move the main conveyor 450 downwardly;
4. Actuate the motor 456M to move the movable frames 456 downwardly;
5. Actuate the motor 750M to move the X-ray tube shield to uncover the tube;
6. Actuate the motor 680M to move the X-ray sub-sub-carriage 680 to lower the X-ray tube.

The scanning preparatory steps 1-6 can only be performed in the order indicated. This is dictated by the program of the control apparatus.

Each of the scanning preparatory steps 1-6 has a reciprocal step. For example, step 1 for moving the spindles together has a reciprocal step of separating the spindles. Step 2 of extending the spindles has a reciprocal step of retracting the spindles, and so on. The operator, upon reaching an intermediate point in the performance of the scanning preparatory steps, rather than electing to complete the series of scanning preparatory steps, may proceed in another manner. He may perform the reciprocal of each of the scanning preparatory steps he has completed, in the reverse order in which the corresponding scanning preparatory steps were performed. For example, if the operator has proceeded through the first four steps, wherein the spindles are moved together, the main conveyor dropped, and the movable frames 456 lowered, he may proceed in reverse order with the reciprocal steps. That is, the operator may then raise the movable frames 456, raise the main conveyor, retract the spindles, and separate the spindles.

If the operator initiates the interrupt mode while the tire is being scanned in accordance with the automatic mode, then the operator thereby acquires control over the scanning functions of the apparatus 100 as explained above in connection with the automatic mode. That is, the operator can manipulate the X-ray tube carriage 620, sub-carriage 660 and sub-sub-carriage 680, along with the imaging system carriage 340, sub-carriage 390 and sub-sub-carriage 420; he can control the speed and direction of rotation of the tire by the spindles 600, and the degree of insertion of the spindles, in order to vary the beadspread as desired for effective inspection.

The operator, while proceeding in the interrupt mode, may return the apparatus 100 to automatic mode. This, however, is permitted only (1) during the time when a tire is actually engaged on the spindles, and (2) immediately upon exiting a tire.

There are two basic types of motors in the apparatus 100. One type is the pneumatic motor, and the other is the drive motor assembly.

The pneumatic motors exert forces tending to move their associated components between two positions. As such, the motor control signals to these motors need be only DC signals produced by the control apparatus. Each motor tends to move toward one position for one state of its DC motor control signal, and assumes the other in response to the motor control signal having another state.

The drive motors can assume any of a range of positions between two limiting positions. The rotative position assumed by the drive motor depends on the value of an analog motor control drive signal directed to that motor from the control apparatus and the time during which it is applied. Each drive motor associated with a potentiometer causes that potentiometer to produce and direct to the control apparatus an analog signal indicating the instantaneous positional state assumed by the drive motor and its associated component. Each of the drive motors is speed controllable as a function of the value of its analog motor control signal produced by the control apparatus.

The control apparatus 1325, in the course of causing the tire inspection apparatus to execute its above described functions, generates analog signals operative for as long as needed to move the movable components to commanded positions determined by the control apparatus.

The control system 1325 provides for automatic slow down of the movable components driven along paths of travel by drive motors associated with potentiometers. The slowing of each component occurs when the component approaches to within a predetermined distance of:

(1) an extreme of its travel path, or
(2) its commanded position.

The control apparatus determines this approach by the analog signals from the potentiometers associated with the respective components. When the control system detects through a potentiometer that a movable component approaches its extreme travel limit or commanded position within a predetermined distance, the control system reduces the drive voltage produced by the analog motor control signal, slowing down the component.

Malfunction Diagnosis

The control apparatus of the tire inspector apparatus 100 senses the occurrence of malfunctions of its components. The apparatus 100 indicates the occurrence of these malfunctions on the malfunction indication display 1306 on the control console 1300.

The malfunction indication display 1306 preferably includes a series of eight lamps connected to the control apparatus. The control apparatus, upon sensing the occurrence of a malfunction generates output signals which light one or more of the lamps. The lamps are lighted in accordance with a code, which identifies the nature of the malfunction.

Whenever a malfunction is detected, the control apparatus produces signals which deactuate all the components of the tire inspection apparatus, and turn over actuation of the apparatus 100 to the interrupt mode, described above.

Preferably, the control apparatus actuates the lamps to light in a unique pattern according to a hexidecimal code to identify the nature of each different malfunction sensed by the control apparatus. In the preferred embodiment, there are 105 different malfunctions which are identified by the coded pattern of lighting of the malfunction display lamps.

These malfunctions are listed below in tabular form in Table I. Table I has four columns. The data in column I indicates each malfunction which can be indicated, in conventional decimal form. The data in column II indicates each type of malfunction in hexidecimal form.

The data in column III of Table I represents the pattern of lighting of the eight malfunction display lamps associated with each type of malfunction. In column III, a "O" represents an unlighted lamp in the position on the malfunction indication display 1306 corresponding to the position of the "O" in column III. The letter "L" represents the lighting of the malfunction display lamp located in the position on the malfunction display corresponding to the position of the "L" in column III.

TABLE I

| I | II | III | IV |
|---|----|-----|----|
| 0 | 00 | 0000 0000 | No malfunction display lamps are lighted when the tire inspector apparatus 100 is operating without malfunction. |
| 1 | 01 | 0000 000L | The photocells 141P1 and 141P2 direct signals to the control apparatus following actuation of the motors 142M and 101M, indicating either that an obstruction is on the entering table 120 or that the photocells 142P1 and 142P2 are not both operating properly. |
| 2 | 02 | 0000 00L0 | The photocells 161P1 and 161P2 are dark, after the photocells 142P1 and 142P2 are dark, indicating the presence of an obstruction on the centering table 120, malfunction of the centering table roller conveyor 140, or of the belt conveyor 101, or that the photocells 161P1 and 161P2 are not both operating properly. |
| 3 | 03 | 0000 00LL | The potentiometer 195P has failed to indicate, after actuation of the motor 190M, that the width sensor bar 210 has retracted to a predetermined location. |
| 4 | 04 | 0000 0L00 | Either of the switches 161S1 and 161S2 is actuated, producing a signal to the control apparatus indicating that the arm assemblies 161 have moved beyond their permitted range of travel. |
| 5 | 05 | 0000 0L0L | The photocells 142P1 and 142P2 fail to indicate the positioning of a tire on the centering table within a predetermined time following the indication by the photocell 101P1 that a tire has cleared the belt conveyor 101. This could indicate failure of the conveyor 101, the centering table conveyor 140, or malfunction of any of the photocells 101P1, 142P1, and 142P2. |

TABLE I-continued

| I | II | III | IV |
|---|----|-----|----|
| 6 | 06 | 0000 0LL0 | The photocell 101P1 remains dark after one of the photocells 142P1 and 142P2 becomes dark. |
| 7 | 07 | 0000 0LLL | The photocells 161P1 and 161P2 directly signal to the control apparatus indicating that at least one of them remains dark for a predetermined time after actuation of the motor 142M. This indicates malfunction of the roller conveyor 140, or of either of the photocells 161P1 and 161P2. |
| 8 | 08 | 0000 L000 | The switch 190S1 and 190S2 produce a signal to the control apparatus indicating that they remain in contact with an object for greater than a predetermined length of time, or are malfunctioning. |
| 9 | 09 | 0000 L00L | The switch 161S1, indicates that the assemblies 161 have moved to their inner extremities without contacting a tire, indicating the tire has an outside diameter too small for the apparatus 100 to handle. |
| 10 | 0A | 0000 L0L0 | The photocells 161P1 and 161P2 produce a signal to the control apparatus indicating that one of them remains dark following the centering of a tire and contact of the switches 190S1 and 190S2. This indicates that an excessively large object is on the centering table 120, or more than one tire is present on the centering table. |
| 11 | 0B | 0000 L0LL | The switch 195S1 produces a signal to the control apparatus indicating that it is in contact with an object before lowering, or is malfunctioning. |
| 12 | 0C | 0000 LL00 | The potentiometer 195P and the switch 195S1 produce signals to the control apparatus indicating that the width sensor bar 210 is not moving and is not in contact with an object, following the actuation of a motor 190M to move the width sensor bar downwardly. This condition indicates that the switch 195S1 is defective, or that the mechanism for moving the width sensor bar has failed. |
| 13 | 0D | 0000 LL0L | The potentiometer 195P and the switch 195S1 produce signals to the control apparatus indicating that the width sensor bar has not retracted upwardly a predetermined distance within a predetermined time after the switch 195S1 terminates contact with a tire. |
| 14 | 0E | 0000 LLL0 | One of the switches 278S2 produces a signal to the control apparatus indicating that the doors of the shielded enclosure are not closed at a time in the operational sequence when they should be, or that one of the switches 278S2 is malfunctioning. |
| 15 | 0F | 0000 LLLL | One of the switches 278S1 produces a signal to the control apparatus indicating that it is made at a time in the operational sequence when the doors should be closed, indicating a malfunction of one of the switches 278S1. |
| 16 | 10 | 000L 0000 | The photosensor 278P1 produces a signal to the control apparatus indicating that it is still receiving light, notwithstanding that one of the switches 278S2 indicates that the front door is closed. |
| 17 | 11 | 000L 000L | The photosensor 278P2 produces a signal to the control apparatus indicating that it is receiving light notwithstanding that one of the switches 278S2 indicates that the rear door to the shielded enclosure is closed. |
| 18 | 12 | 000L 00L0 | The switch 680S1 fails to produce a signal to the control apparatus indicating that the X-ray sub-sub-carriage has moved the X-ray tube assembly 700 up at a time in the operational sequence when it should be up. |

TABLE I-continued

| I | II | III | IV |
|---|---|---|---|
| 19 | 13 | 000L 00LL | The switch 680S$_2$ produces a signal indicating that it remains made at a time in the operational sequence when the tube assembly 700 should be raised, indicating a malfunction of the switch 680S$_2$. |
| 20 | 14 | 000L 0L00 | The switch 451S$_1$ fails to produce a signal indicating that the frame 451 is raised at a time in the operational sequence when the frame 451 should be raised. |
| 21 | 15 | 000L 0L0L | The switch 451S$_2$ produces a signal to the control apparatus indicating that it is made at a time in the operational sequence when the frame 451 should be raised indicating a malfunction of the switch 451S$_2$. |
| 22 | 16 | 000L 0LL0 | The switch 660S$_1$ fails to produce a signal to the control apparatus indicating that the X-ray sub-carriage has moved the X-ray tube assembly 700 to a non-offset position at a time in the operational sequence when the X-ray tube assembly should not be offset. |
| 23 | 17 | 000L 0LLL | The switch 660S$_2$ produces a signal to the control apparatus indicating that it is made at a time in the operational sequence when the X-ray tube should not be offset, indicating a malfunction in the switch 660S$_2$. |
| 24 | 18 | 000L L000 | One of the switches 340S$_1$ and 340S$_2$ produces a signal to the control apparatus indicating that the imaging system carriage 340 has moved to an extreme position of its range of travel. |
| 25 | 19 | 000L L00L | One of the switches 390S$_1$ and 390S$_2$ produces a signal to the control apparatus indicating that the imaging system sub-carriage 390 has reached an extreme position of its path of travel. |
| 26 | 1A | 000L L0L0 | One of the switches 420S$_1$ and 420S$_2$ produces a signal to the control apparatus indicating that the imaging system sub-sub-carriage 420 has reached an extreme of its path of travel. |
| 27 | 1B | 000L L0LL | One of the switches 440S$_1$, 440S$_2$, and 440S$_3$ and the photocell 440P$_1$ produce a signal indicating to the control apparatus that the imaging unit 440 has or is about to contact another object. |
| 28 | 1C | 000L LL00 | One of the switches 820S$_1$ and 820S$_2$ produces a signal to the control apparatus indicating that the positioning switch assembly 820 has reached an extreme of its path of travel. |
| 29 | 1D | 000L LL0L | One of the switches 460S$_1$ and 460S$_2$ produces a signal to the control apparatus indicating that the gear racks 460 have reached an extreme of their path of travel. |
| 30 | 1E | 000L LLL0 | One of the switches 140S$_1$ and 140S$_2$ produces a signal to the control apparatus indicating that the centering table roller conveyor 140 has reached an extreme in its path of travel. |
| 31 | 1F | 000L LLLL | One of the switches 456S$_1$ fails to produce a signal to the control apparatus indicating that the movable frame 456 is raised at a time in the operational sequence when the movable frame 456 should be raised. |
| 32 | 20 | 00L0 0000 | One of the switches 456S$_2$ produces a signal to the control apparatus indicating that it is made at a time in the operational sequence when the movable frame 456 should be raised, indicating a malfunction of one of the switches 456S$_2$. |
| 33 | 21 | 00L0 000L | The switch 750S$_1$ fails to produce a signal to the control apparatus indicating that the X-ray tube shield is covering the X-ray tube at a time in the operational sequence when the X-ray tube should be covered. |
| 34 | 22 | 00L0 00L0 | The switch 750S$_2$ produces a signal to the control apparatus indicating that it is made at a time in the operational sequence when the X-ray tube should be covered, indicating a malfunction of the switch 750S$_2$. |
| 35 | 23 | 00L0 00LL | One or more of the photocells 600P$_1$ produces a signal to the control apparatus indicating that it is not receiving light just before the doors 278 open to admit the tire, indicating a malfunctioning photocell 600P$_1$, or an object in the enclosure. |
| 36 | 24 | 00L0 0L00 | The switch 550S$_2$ produces a signal to the control apparatus indicating that it is made at a time in the operational sequence when the spindles should be retracted, indicating a malfunction in the switch 550S$_2$. |
| 37 | 25 | 00L0 0L0L | The switch 550S$_1$ fails to produce a signal to the control apparatus indicating that the spindles are retracted at a time in the operational sequence when the spindles should be retracted. |
| 38 | 26 | 00L0 0LL0 | One of the switches 278S$_1$ fails to indicate that the shielded enclosure doors are open within a predetermined time following the actuation of the motor 278M to open the doors. |
| 39 | 27 | 00L0 0LLL | One of the switches 278S$_2$ indicates that it is made at a time in the operational sequence when the doors should be open, indicating a malfunction in one of the switches 278S$_2$. |
| 40 | 28 | 00L0 L000 | The photocell 278P$_1$ produces a signal to the control apparatus indicating it is not receiving light during a time in which the switches 278S$_1$ indicate that the shielded enclosure doors are open. This indicates an obstruction in the front door, or failure of the photocell 278P$_1$. |
| 41 | 29 | 00L0 L00L | The photocell 278P$_2$ indicates to the control apparatus that it is not receiving light at a time when the switches 278S$_1$ indicate that the shielded enclosure doors are open. This indicates failure of the photocell 278P$_2$, or an obstruction in the rear door. |
| 42 | 2A | 00L0 L0L0 | The switch 452S$_1$ on the positioning switch assembly produces a signal to the control apparatus indicating that it is made prior to entry of the tire to the enclosure. |
| 43 | 2B | 00L0 L0LL | The switch 452S$_2$ of the positioning switch assembly 820 produces a signal to the control apparatus indicating that it is made prior to tire entry to the enclosure. |
| 44 | 2C | 00L0 LL00 | The switch 452S$_1$ fails to produce a signal to the control apparatus within a predetermined time following actuation of the main conveyor 450 to move the tire to engage the limit switch assembly. |
| 45 | 2D | 00L0 LL0L | The switch 452S$_1$ fails to produce a signal to the control apparatus, before making of the switch 452S$_2$. |
| 46 | 2E | 00L0 LLL0 | The switch 452S$_2$ fails to produce a signal to the control apparatus within a predetermined time of the actuation of the switch 452S$_1$. |
| 47 | 2F | 00L0 LLLL | At least one of the photocells 600P$_1$ produces a signal to the control apparatus indicating that it is receiving light during the entire period of tire entry into the enclosure. |
| 48 | 30 | 00LL 0000 | The photocell 278P$_1$ produces a signal to the control apparatus indicating that it fails to receive light for longer than a predetermined period of time during which the switches 278S$_1$ indicate that the shielded enclosure doors 278 are open. |

TABLE I-continued

| I | II | III | IV |
|---|---|---|---|
| | | | This indicates an obstruction at the front door. |
| 49 | 31 | 00LL 000L | The photocell 278P$_2$ produces a signal to the control apparatus indicating that it fails to receive light for longer than a predetermined period of time during which the switches 278S$_1$ indicate that the shielded enclosure doors 278 are open. This indicates an obstruction at the rear door. |
| 50 | 32 | 00LL 00L0 | The switch 278S$_2$ fails to produce a signal to the control apparatus indicating the closure of the doors within a predetermined time following the actuation of the motor 278M to close the doors 278. |
| 51 | 33 | 00LL 00LL | The switch 750S$_1$ produces a signal to the control apparatus indicating that it is made at a time in the operational sequence when the X-ray tube should be uncovered, indicating a malfunction of the switch 750S$_1$. |
| 52 | 34 | 00LL 0L00 | The switch 750S$_2$ fails to produce a signal to the control apparatus, indicating that the X-ray tube shield has uncovered the X-ray tube within a predetermined time following actuation of the motor 750M. |
| 53 | 35 | 00LL 0L0L | The switch 452S$_1$ produces a signal to the control apparatus indicating the engagement of the positioning switch assembly 820 with a tire after the positioning switch assembly should have backed away from the tire. |
| 54 | 36 | 00LL 0LL0 | The switch 452S$_2$ produces a signal to the control apparatus indicating the engagement of the positioning switch assembly with a tire at a time in the operational sequence after the positioning switch assembly should have backed away from the tire. |
| 55 | 37 | 00LL 0LLL | The photocells 600P$_1$ fail to produce signals to the control apparatus indicating that the tire is centered under the spindles. |
| 56 | 38 | 00LL L000 | The switch 550S$_1$ produces a signal to the control apparatus indicating that the spindles are retracted for a predetermined period of time following the actuation of the motor 550m to extend the spindles. |
| 57 | 39 | 00LL L00L | The switch 456S$_2$ fails to produce a signal to the control apparatus indicating that the movable frame 456 has reached its lower position within a predetermined time following the production of a signal to the control apparatus by the switch 456S$_1$ indicating that the movable frame 456 has moved from its raised position. |
| 58 | 3A | 00LL L0L0 | The switch 456S$_1$ produces a signal indicating that it is made at a time in the operational sequence when the movable frame should be in its lowered position, indicating a malfunction in the switch 456S$_1$. |
| 59 | 3B | 00LL L0LL | The switch 451S$_2$ fails to produce a signal to the control apparatus indicating that the frame 451 has reached its lower position, for a predetermined time following the indication by the switch 451S$_1$ to the control apparatus that the frame 451 has left its lowered position. |
| 60 | 3C | 00LL LL00 | The switch 451S$_1$ produces a signal indicating that it is made at a time in the operational sequence when the frame 451 should be in its lowered position, indicating a malfunction of the switch 451S$_1$. |
| 61 | 3D | 00LL LL0L | The switch 680S$_2$ fails to produce a signal to the control apparatus indicating that the X-ray sub-sub-carriage 680 has lowered the X-ray tube assembly 700 within a predetermined time following the indication by the switch 680S$_1$ to the control apparatus that the X-ray tube assembly has moved from its raised position. |
| 62 | 3E | 00LL LLL0 | The switch 680S$_1$ produces a signal to the control apparatus indicating that it is made at a time in the operational sequence when the X-ray tube assembly 700 should be in a lowered position, indicating a malfunction in the switch 680S$_1$. |
| 63 | 3F | 00LL LLLL | The switch 660S$_1$ fails to produce a signal to the control apparatus indicating that the X-ray sub-carriage has offset the X-ray tube assembly 700 within a predetermined amount of time following the indicating by the switch 660S$_2$ to the control apparatus that the X-ray tube assembly has been moved from its nonoffset position. |
| 64 | 40 | 0L00 0000 | The switch 660S$_2$ produces a signal to the control apparatus indicating that it is made at a time in the operational sequence when the X-ray tube assembly should be offset, indicating a malfunction of the switch 660S$_2$. |
| 65 | 41 | 0L00 000L | The switch 660S$_2$ fails to produce a signal indicating that the X-ray sub-carriage 620 has moved the X-ray tube assembly 700 to its nonoffset position for a predetermined amount of time following an indication by the switch 660S$_1$ that the X-ray tube has been moved from its offset position. |
| 66 | 42 | 0L00 00L0 | The switch 680S$_1$ fails to produce a signal to the control apparatus indicating that the X-ray sub-sub-carriage 680 has raised the X-ray tube assembly 700 within a predetermined period following the indication by the switch 680S$_2$ that the X-ray tube has been raised from a lowered position. |
| 67 | 43 | 0L00 00LL | The switch 750S$_1$ fails to produce a signal to the control apparatus indicating that the X-ray tube shield 750 has been moved to its covered position within a predetermined time following the indication by the switch 750S$_2$ to the control apparatus that the tube shield has been moved from its uncovered position. |
| 68 | 44 | 0L00 0L00 | The switch 451S$_1$ fails to produce a signal indicating to the control apparatus that the frame 451 has been raised to its upper position within a predetermined time following the production of a signal to the control apparatus by the switch 451S$_2$ indicating that the frame 451 has been raised from its lowered position. |
| 69 | 45 | 0L00 0L0L | The switch 456S$_1$ fails to produce a signal to the control apparatus indicating that the movable frame 456 has reached its raised position within a predetermined time after the switch 456S$_2$ has indicated to the control apparatus that the movable frame 456 has begun to be raised from its lowered position. |
| 70 | 46 | 0L00 0LL0 | The switch 550S$_1$ fails to produce a signal to the control apparatus indicating that the spindles have retracted within a predetermined time after the actuation of the motor 550M to retract the spindles. |
| 71 | 47 | 0L00 0LLL | The photocell 278P$_2$ fails to indicate to the control apparatus that the tire has interrupted the light beam falling on the photocell within a predetermined time following the actuation of the motor 450M to exit the tire through the exit door. |
| 72 | 48 | 0L00 L000 | The photocell 278P$_2$ produces a signal to the control apparatus indicating that the light incident on the photocell 278P$_2$ has been interrupted for more than a predetermined time, during actuation of the main conveyor 450M, indicating that the tire |

TABLE I-continued

| I | II | III | IV |
|---|---|---|---|
| | | | is moving out too slowly. |
| 73 | 49 | 0L00 L00L | The photocell 278P₂ produces a signal to the control apparatus indicating that a tire is exiting, notwithstanding that neither switches 820S₁ nor 821S₂ have been previously actuated by the tire's engagement with the positioning switch assembly 820. |
| 74 | 4A | 0L00 L0L0 | The photocell 278P₂ produces a signal to the control apparatus indicating that the tire has exited while one of the switches 820S₁ and 820S₂ produce a signal indicating engagement of the positioning switch assembly 820 by a tire. |
| 75 | 4B | 0L00 L0LL | The control apparatus detects a power failure in the control apparatus, via a connection from the power control panel 1302. |
| 76 | 4C | 0L00 LL00 | The control apparatus detects a memory parity error in the memory of the computer which requires service. This is detected by a connection to a built-in terminal on the computer 1310. |
| 77 | 4D | 0L00 LL0L | The control apparatus detects an unrecognized code in input to the control apparatus, via a built-in terminal on the computer 1310. |
| 78 | 4E | 0L00 LLL0 | The control apparatus detects a memory violation in the computer, which requires service, via a built-in terminal on the computer 1310. |
| 79 | 4F | 0L00 LLLL | One of the switches 440S₁, 440S₂, 440S₃ or the photocell 440P₁ produces a signal to the control apparatus indicating that the imaging unit is about to collide with another object. |
| 80 | 50 | 0L0L 0000 | Operator in manual mode must exit the tire in the machine because tire not in position to resume auto mode. |
| 81 | 51 | 0L0L 000L | X-ray carriage 620 is operating too slowly, or in wrong direction, as indicated by the potentiometer 620P. |
| 82 | 52 | 0L0L 00L0 | The potentiometer 620P produces a signal to the control apparatus indicating that the X-ray carriage has moved beyond its computer controlled travel limit. |
| 83 | 53 | 0L0L 00LL | Spindle insert/remove drive 510M is operating in wrong direction, or too slowly, as detected by the signal from the potentiometer 510P. |
| 84 | 54 | 0L0L 0L00 | The potentiometer 510P produces a signal to the control apparatus indicating that the spindle carriages have moved beyond their computer control travel limit. |
| 85 | 55 | 0L0L 0L0L | The image system subcarriage 390 is operating too slowly or in the wrong direction, as sensed by the potentiometer 390P. |
| 86 | 56 | 0L0L 0LL0 | The potentiometer 390P produces a signal to the control apparatus indicating that the imaging system subcarriage has traveled beyond its computer controlled permitted travel limit. |
| 87 | 57 | 0L0L 0LLL | Imaging system sub-subcarriage 420 is operating too slowly or in the wrong direction, as sensed by the potentiometer 420P. |
| 88 | 58 | 0L0L L000 | The potentiometer 420P produces a signal to the control apparatus indicating that the imaging system sub-subcarriage has moved beyond its computer controlled permitted travel limit. |
| 89 | 59 | 0L0L L00L | Tire centering drive 161M is operating too slowly or in the wrong direction, as sensed by the potentiometer 161P. |
| 90 | 5A | 0L0L L0L0 | The potentiometer 161P produces a signal to the control apparatus indicating that the drive of the arm assemblies 161 is beyond its computer controlled permitted travel limit. |
| 91 | 5B | 0L0L L0LL | The centering table drive 140M is operating too slowly, or in the wrong direction, as sensed by the potentiometer 140P. |
| 92 | 5C | 0L0L LL00 | The potentiometer 140P produces a signal to the control apparatus indicating that the centering table 120 has been raised or lowered beyond its computer controlled permitted travel limit. |
| 93 | 5D | 0L0L LL0L | Main conveyor gear rack drive 460M is operating too slowly, or in the wrong direction, as sensed by the potentiometer 460P. |
| 94 | 5E | 0L0L LLL0 | The potentiometer 460P produces a signal to the control apparatus indicating that the gear racks 460 of the main conveyor have been raised or lowered beyond their computer controlled travel limit. |
| 95 | 5F | 0L0L LLLL | The imaging system carriage drive 340M is operating too slowly, or in the wrong direction, as sensed by the potentiometer 340P. |
| 96 | 60 | 0LL0 0000 | The potentiometer 340P produces a signal to the control apparatus indicating that the imaging system carriage 340 has moved outside its computer controlled travel limit. |
| 97 | 61 | 0LL0 000L | X-ray tube pivoting drive 700M is operating too slowly or in the wrong direction as sensed by the potentiometer 700P. |
| 98 | 62 | 0LL0 00L0 | The potentiometer 700P produces a signal to the control apparatus indicating that the X-ray tube housing assembly has pivoted beyond its permitted computer controlled limits of rotation. |
| 99 | 63 | 0LL0 00LL | The positioning switch positioning drive 820M is operating too slowly or in the wrong direction, as sensed by the potentiometer 820P. |
| 100 | 64 | 0LL0 0L00 | The potentiometer 820P produces a signal to the control apparatus indicating that the positioning switch assembly 820 has moved beyond its computer controlled permitted travel limit. |
| 101 | 65 | 0LL0 0L0L | The potentiometer 195P produces a signal to the control apparatus indicating that the height sensor bar 210 has moved beyond its computer controlled permitted travel limit. |
| 102 | 66 | 0LL0 0LL0 | The potentiometer 510P produces a signal to the control apparatus indicating that the spindles are inserted or removed beyond their computer controlled permitted travel limit. |
| 103 | 67 | 0LL0 0LLL | The control apparatus detects the occurrence of a malfunction in the digital to analog converter 1336, requiring service. |
| 104 | 68 | 0LL0 L000 | The control apparatus, through a connection thereto, detects a malfunction in the analog to digital converter 1332, requiring service. |
| 105 | 69 | 0LL0 L00L | The measurements of tire outside diameter and which indicate that the apparatus 100 would have to drive one of its components past its limited path to handle the tire. |

Although the invention has been described in its preferred form with a certain degree of particularity, it is understood that the present disclosure of the preferred form has been made only by way of example and numerous changes in the details of construction and the combination and arrangement of parts may be resorted to without departing from the spirit and the scope of the invention as hereinafter claimed.

We claim:

1. In a tire inspection apparatus of the type having drive means for delivering and positioning a tire at an inspection station, an inspection apparatus having a movable penetrative emanation source for emitting penetrative emanation along a path, and a movable penetrative emanation detector, first and second motive structures for moving said source and detector, the improvement of a positioning system comprising:
(a) sensing means for producing signals indicating the positions of said source and said detector;
(b) positioning means connected between said sensing apparatus and said first and second motive structures and being responsive to said position indicating signals to compare the relative positions of said source and detector to produce output signals to said first and second motive structures to effect the maintenance of a substantially constant spatial relation between said source and said detector.

2. The system of claim 1, further comprising:
(a) structure supporting said detector for movement along an arcuate travel path;
(b) structure supporting said source for pivotal movement about an axis perpendicular to the plane containing said arcuate path;
(c) said positioning means being responsive to the pivoting of said source relative to move said detector along said arcuate path to maintain said detector substantially in the path of penetrative emanation from said source.

3. The system of claim 2, wherein:
(a) said source and said detector are independently supported for movement along parallel paths; and
(b) said positioning means includes means for actuating one of said motive structures to move one of said detector and source in response to movement of the other to maintain a predetermined distance between said source and said detector.

4. The system of claim 3, wherein said predetermined distance is that distance at which the center of said arcuate path is located substantially at the emission point of said source.

5. The system of claim 1, wherein:
(a) said source and said detector are independently supported for movement along parallel paths toward and away from each other; and,
(b) said positioning means includes means for actuating one of said motive structures to move one of said detector and said source in response to movement of the other in said same direction to maintain predetermined distance between said source and said detector.

6. A method of cooperatively positioning a penetrative emanation source and a penetrative emanation detector for a tire inspection apparatus, said source and detector being independently movable and connected to first and second motive structures, respectively, said method comprising the steps of:
(a) sensing the relative positions of said source and said detector;
(b) comparing the relative positions of said source and said detector; and,
(c) actuating said motive structures in response to said comparison to effect the maintenance of a substantially constant spatial relation between said source and said detector, notwithstanding the movement of one of said source and said detector.

7. The method of claim 6, wherein said detector is movable along an arcuate travel path and said source is pivotally movable about an axis perpendicular to a plane containing said arcuate travel path, and said actuating step includes maintaining a constant relative rotational orientation between said detector and said source.

8. The method of claim 6, wherein said source and said detector are independently movable along parallel paths, and said actuating step includes maintaining a predetermined spacing between said source and said detector with respect to movement along said parallel paths.

* * * * *